(12) United States Patent
Griffin et al.

(10) Patent No.: US 10,407,488 B2
(45) Date of Patent: Sep. 10, 2019

(54) THERAPY FOR TREATMENT OR PREVENTION OF CONDITIONS ASSOCIATED WITH BLEEDING OR HYPOCOAGULATION

(71) Applicants: THE REGENTS OF THE UNIVERSITY OF CALIFORNIA, Oakland, CA (US); THE SCRIPPS RESEARCH INSTITUTE, La Jolla, CA (US)

(72) Inventors: John H. Griffin, Del Mar, CA (US); Laurent Mosnier, San Diego, CA (US); Annette Von Drygalski, La Jolla, CA (US); Andrew Gale, San Diego, CA (US)

(73) Assignees: THE REGENTS OF THE UNIVERSITY OF CALIFORNIA, Oakland, CA (US); THE SCRIPPS RESEARCH INSTITUTE, La Jolla, CA (US)

( * ) Notice: Subject to any disclaimer, the term of this patent is extended or adjusted under 35 U.S.C. 154(b) by 0 days.

(21) Appl. No.: 15/034,385

(22) PCT Filed: Nov. 4, 2014

(86) PCT No.: PCT/US2014/063898
§ 371 (c)(1),
(2) Date: Sep. 30, 2016

(87) PCT Pub. No.: WO2015/066700
PCT Pub. Date: May 7, 2015

(65) Prior Publication Data
US 2016/0289299 A1 Oct. 6, 2016

Related U.S. Application Data

(60) Provisional application No. 61/899,544, filed on Nov. 4, 2013, provisional application No. 61/944,915, filed on Feb. 26, 2014.

(51) Int. Cl.
*A61K 38/36* (2006.01)
*C07K 14/745* (2006.01)
*A61K 38/48* (2006.01)
*A61K 45/06* (2006.01)

(52) U.S. Cl.
CPC ............ *C07K 14/745* (2013.01); *A61K 38/36* (2013.01); *A61K 38/4846* (2013.01); *A61K 45/06* (2013.01); *C12Y 304/21021* (2013.01)

(58) Field of Classification Search
None
See application file for complete search history.

(56) References Cited

U.S. PATENT DOCUMENTS

| 5,698,677 A | 12/1997 | Eibl et al. |
| 2003/0125256 A1 | 7/2003 | Rojkjaer |
| 2007/0276128 A1 | 11/2007 | Griffin et al. |
| 2010/0144620 A1 | 6/2010 | Van Den Nieuwenhof et al. |

FOREIGN PATENT DOCUMENTS

| WO | 2009/079690 | 7/2009 |
| WO | 2010/149172 | 12/2010 |

OTHER PUBLICATIONS

Yang, T.L., et al, The Structure and Function of Murine Factor V and its Inactivation by Protein C, Blood, vol. 91, No. 12, 1998, 4593-4599 (Year: 1998).*
UniProtKB—P12259 (FA5_Human), pp. 1-17 (Year: 2018).*
von Drygalski A, et al. "An engineered factor Va prevents bleeding induced by anticoagulant wt activated protein C," PLoS One. Aug. 15, 2014;9(8):e104304. 10 pages.
Moll, S. "The 4th New Oral Anticoagulant (Edoxaban): New Publication," Clot Connect: Patient Education Blog, Sep. 2, 2013. 1 page.
(Continued)

*Primary Examiner* — Thomas S Heard
(74) *Attorney, Agent, or Firm* — Robin L. Teskin; LeClairRyan PLLC

(57) ABSTRACT

The present application generally relates to methods to prevent or treat bleeding and/or hypocoagulation in an individual in need thereof, and compositions for use in such methods. The methods comprise administration of FVa, preferably an APC resistant FVa (such as $^{super}$FVa), alone or in combination with FVIIa, preferably rhFVIIa (such as NovoSeven® or another FVIIa having enhanced activity or half-life). When administered in combination, FVa and FVIIa elicit a synergistic benefit when used to treat or prevent bleeding or hypocoagulation in subjects in need thereof, e.g., subjects with a genetic disorder such as hemophilia or an acquired bleeding disorder or other condition associated with bleeding or hypocoagulation such as hemorrhagic stroke or shock, trauma, surgery or dysmenorrhea or individuals who produce inhibitory antibodies against procoagulants such as FVIII or FIX or who have been administered an overdose of an anticoagulant drug such as a direct Xa or direct thrombin inhibitor or a Novel Oral Anti-Coagulant (NOAC) or demonstrate unexplained bleeding. Also, the invention relates to the use of a $^{super}$FVa alone or in combination with FVIIa or other procoagulant or prohemostatic agent to prevent, treat or reverse APC-associated bleeding, e.g., as the result of APC overproduction (such as through serious injury and/or hemorrhagic shock) or APC or other anticoagulant therapy, e.g., in the treatment of inflammatory disorders or sepsis disease.

Figure 1:
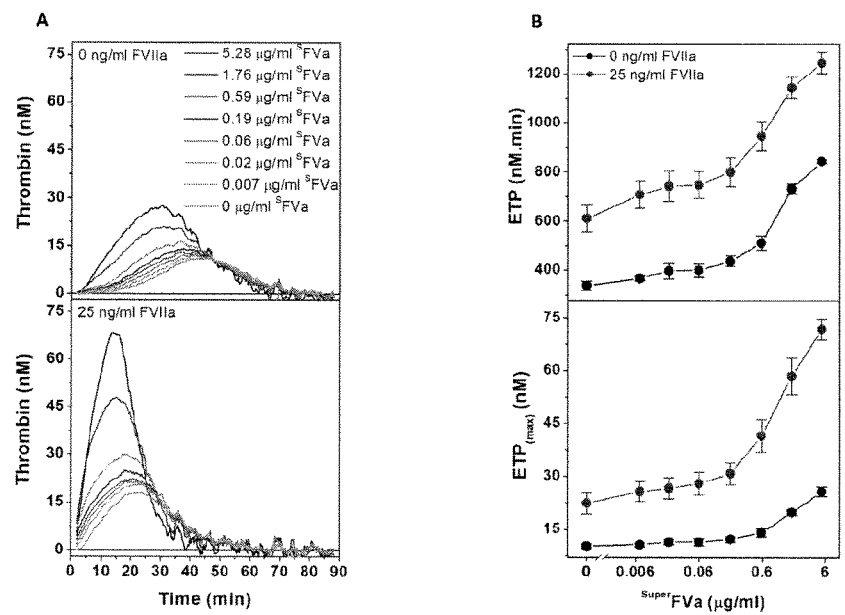

20 Claims, 34 Drawing Sheets
Specification includes a Sequence Listing.

(56) References Cited

OTHER PUBLICATIONS

Gale AJ, et al. "Interdomain engineered disulfide bond permitting elucidation of mechanisms of inactivation of coagulation factor Va by activated protein C," Protein Sci. Sep. 2002;11(9):2091-101. 11 pages.
Sarangi PP, et al. "ctivated protein C action in inflammation," Br J Haematol. Mar. 2010;148(6):817-33. 27 pages.

* cited by examiner

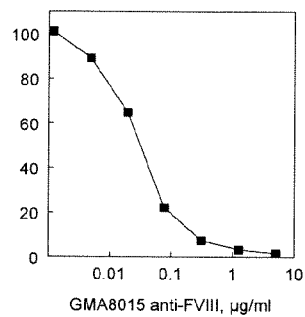
Figure 6. Bethesda titer of GMA8015 anti-FVIII. FVIII inhibitory activity was measured according to a modified Nijmegen Bethesda assay according to the protocol described in Barrow and Lollar, JTH, 2006. 50% FVIII activity was remaining at 0.031 ug/ml of GMA8015. This results in 32,300 BU/mg of GMA8015.

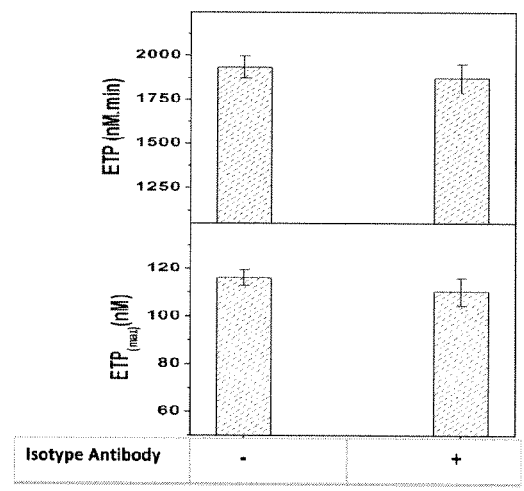

Figure 7: Thrombin generation in normal human plasma with and without isotype antibody. Thrombin generation was determined in pooled normal human as endogenous thrombin potential (ETP) in normal pooled human plasma in the the presence or absence of 1.25 µg/ml isotype antibody, expressed as area under the curve (top panle) and peak height (bottom panel). Error bars represent standard error of the mean (n≥3).

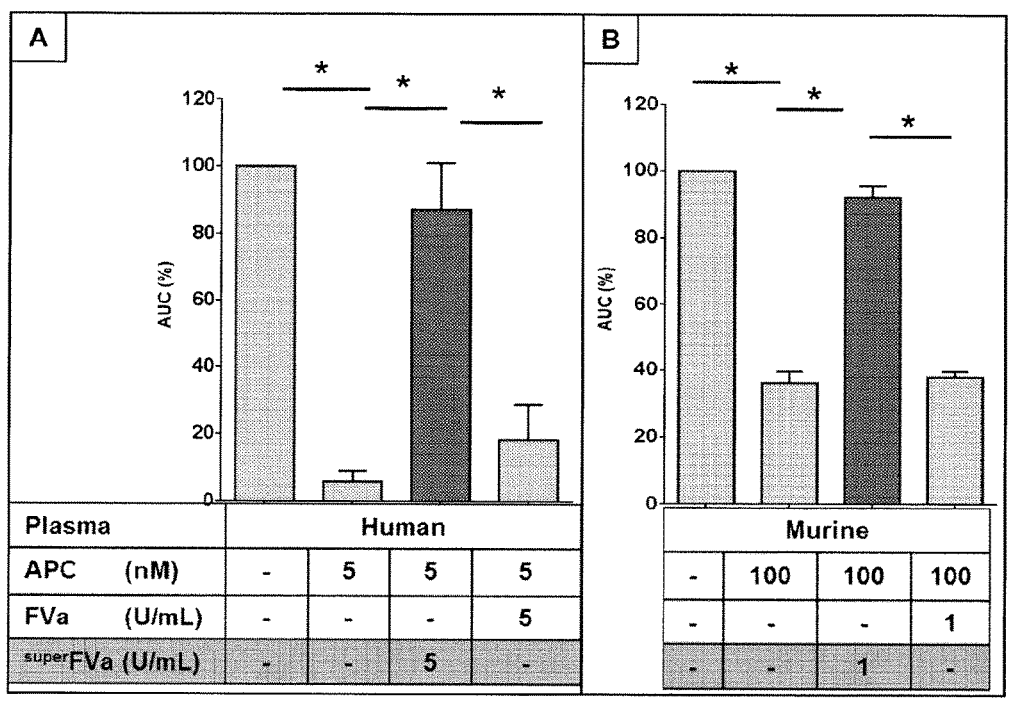
Figure 8. Thrombin generation was determined in A) normal human plasma, and B) murine Balb/c plasma supplemented with rhFVa or rh$^{super}$FVa in the presence of rhAPC. Thrombin generation was expressed as area under curve (AUC) (n=4-6). Error bars represent standard error of the mean. * denotes statistical significance (all p-values < 0.001).

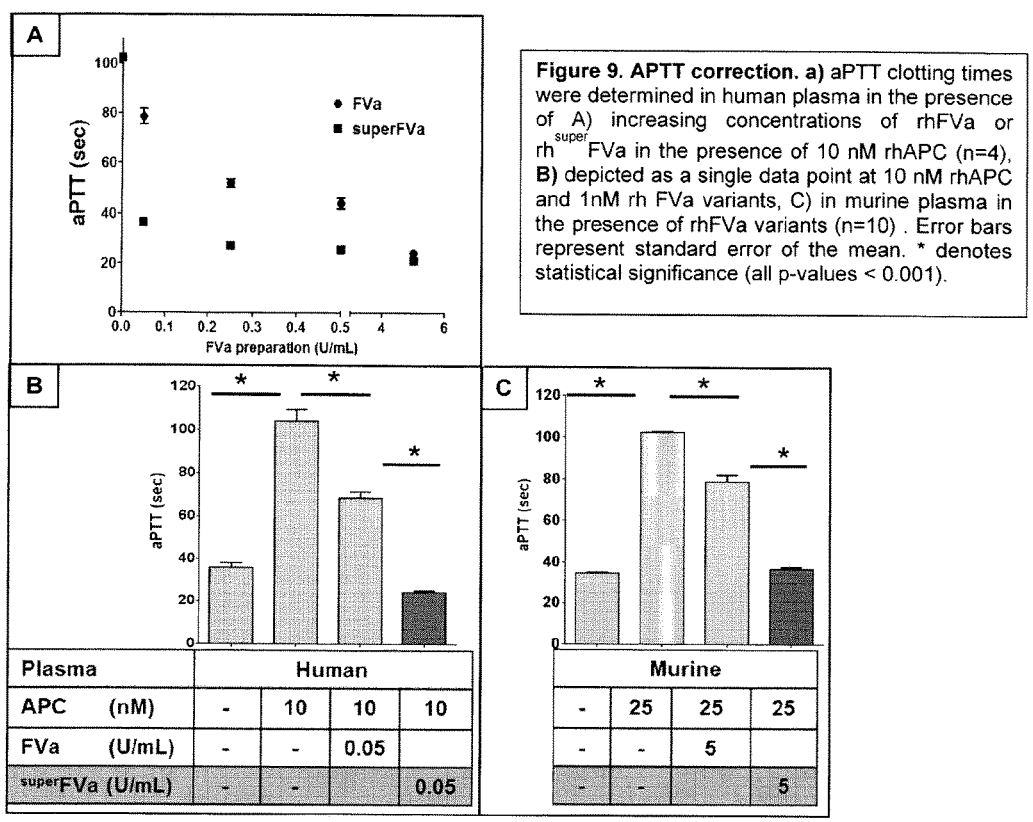

Figure 9. APTT correction. a) aPTT clotting times were determined in human plasma in the presence of A) increasing concentrations of rhFVa or rh$^{super}$FVa in the presence of 10 nM rhAPC (n=4), B) depicted as a single data point at 10 nM rhAPC and 1nM rh FVa variants, C) in murine plasma in the presence of rhFVa variants (n=10). Error bars represent standard error of the mean. * denotes statistical significance (all p-values < 0.001).

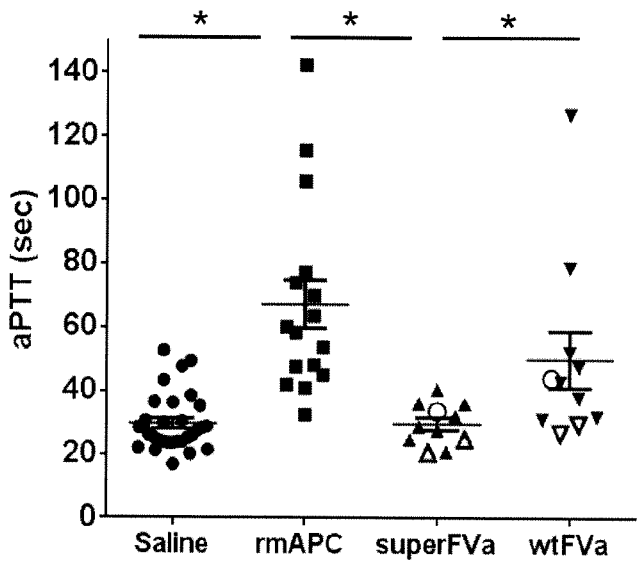

Figure 10. APTT correction with FVa variants after intravenous injection of recombinant murine APC into Balb/c mice. Mice were injected intravenously with saline or rmAPC (0.5 mg/kg). Two minutes later blood was collected retroorbitally and whole blood aPTT was determined immediately. In two groups of mice that were injected with APC whole blood was spiked ex vivo with either $^{super}$FVa or wt FVa (open triangles 1 U/mL, open circles 0.5 U/mL, closed triangles 0.05 U/mL) to determine the extent of aPTT correction with both variants. Error bars represent standard error of the mean. * denotes statistical significance (all p-values < 0.001).

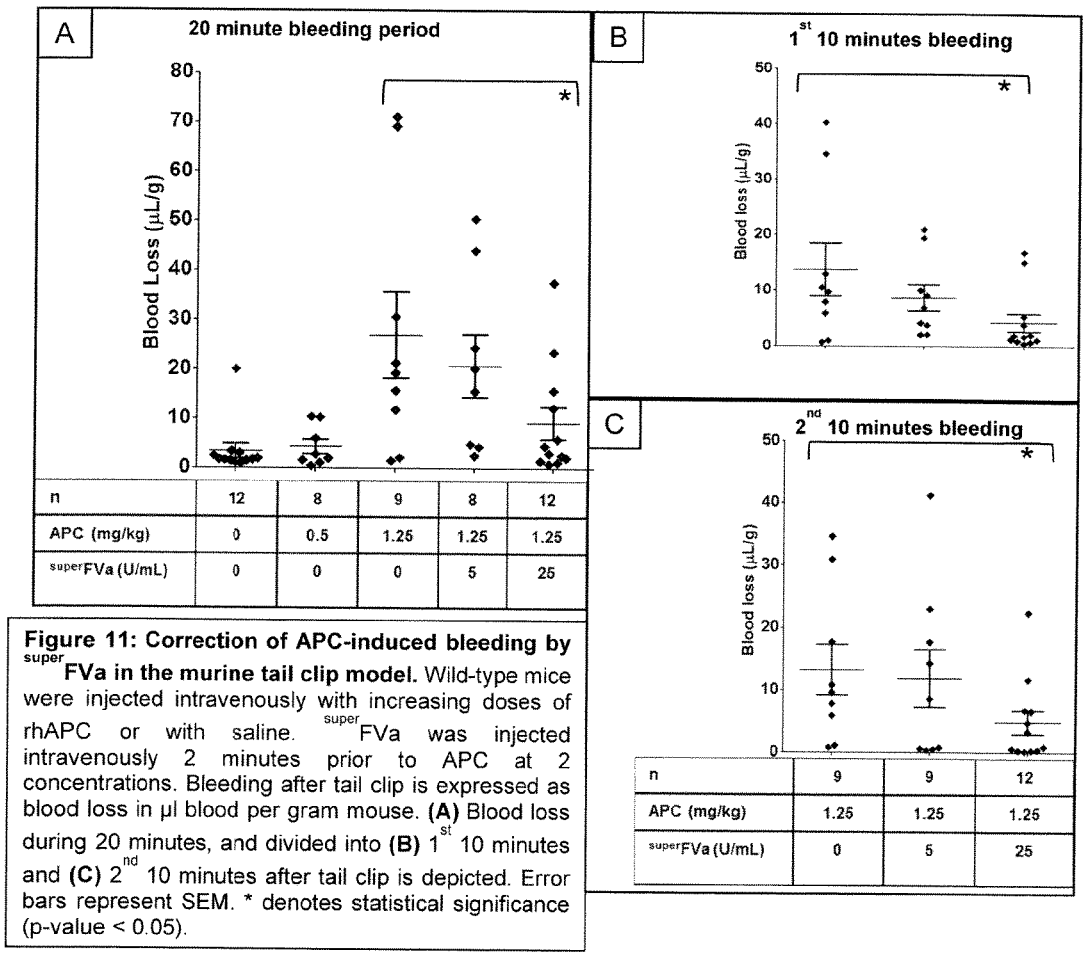

Figure 11: Correction of APC-induced bleeding by superFVa in the murine tail clip model. Wild-type mice were injected intravenously with increasing doses of rhAPC or with saline. superFVa was injected intravenously 2 minutes prior to APC at 2 concentrations. Bleeding after tail clip is expressed as blood loss in μl blood per gram mouse. (A) Blood loss during 20 minutes, and divided into (B) 1st 10 minutes and (C) 2nd 10 minutes after tail clip is depicted. Error bars represent SEM. * denotes statistical significance (p-value < 0.05).

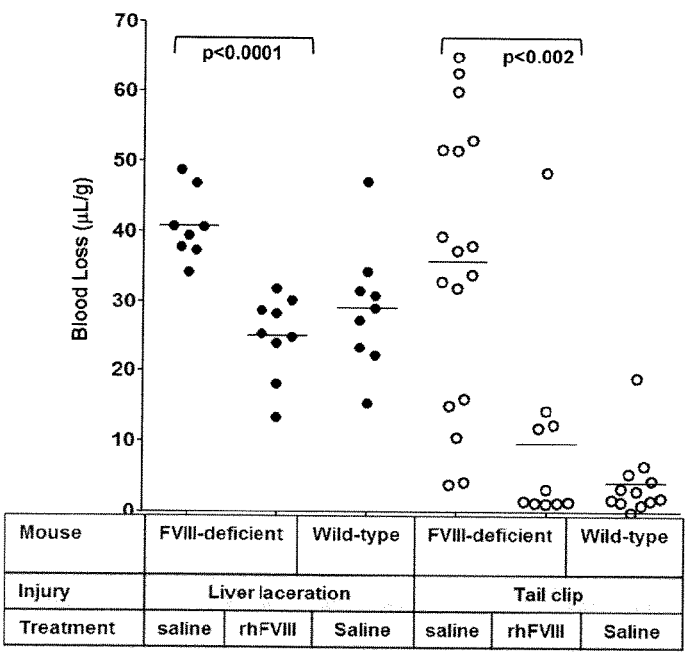

Figure 12: Direct comparison of bleeding patterns following tail clip and liver laceration. FVIII-deficient mice were injected intravenously with saline (200 µL) or rhFVIII (50 U/kg; 200 µL) and subjected to tail clip or liver laceration. Wild-type Balb/c mice were injected with saline for baseline values. Blood loss in all groups of mice during 20 minutes was determined in both models.

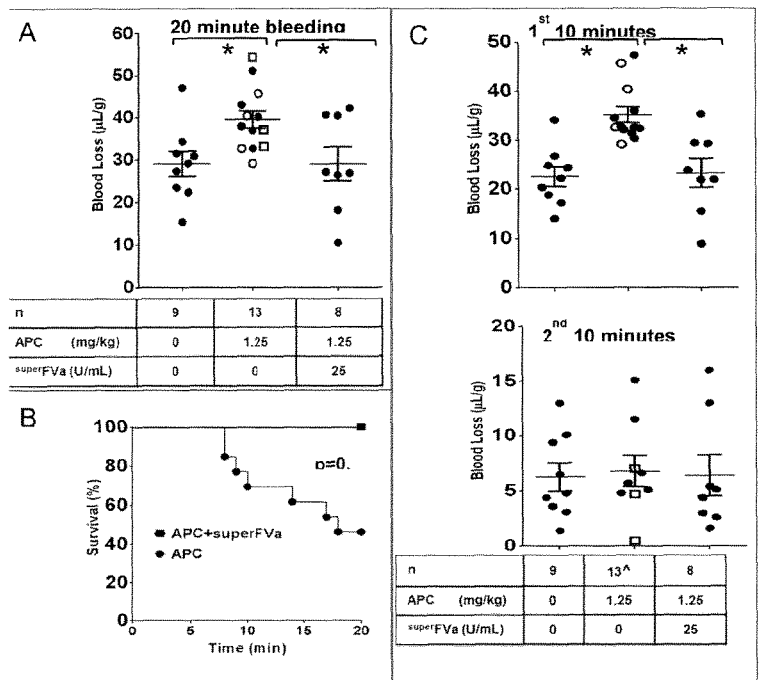

Figure 13: Correction of APC-induced bleeding by $^{super}$FVa after liver laceration. Mice were injected intravenously with saline or plasma derived human APC at 1.25 mg/kg. $^{super}$FVa was injected intravenously 2 minutes prior to APC at 3.5 mg/kg. Bleeding after liver laceration is expressed as blood loss in μl blood per gram mouse. (A) Blood loss and (B) survival during 20 minutes. (C) Blood loss divided into $1^{st}$ 10 minutes (top panel) and $2^{nd}$ 10 minutes (bottom panel) after injury. Error bars represent SEM. * denotes statistical significance (p-value < 0.01). ^Four of 13 mice injected with APC died during the $1^{st}$ 10 minutes after injury (open circles). Three more mice died during the $2^{nd}$ 10 minutes, respectively (open rectangles) and are therefore excluded from bottom panel. Error bars represent standard error of the mean. * denotes statistical significance (all p-values ≤ 0.01).

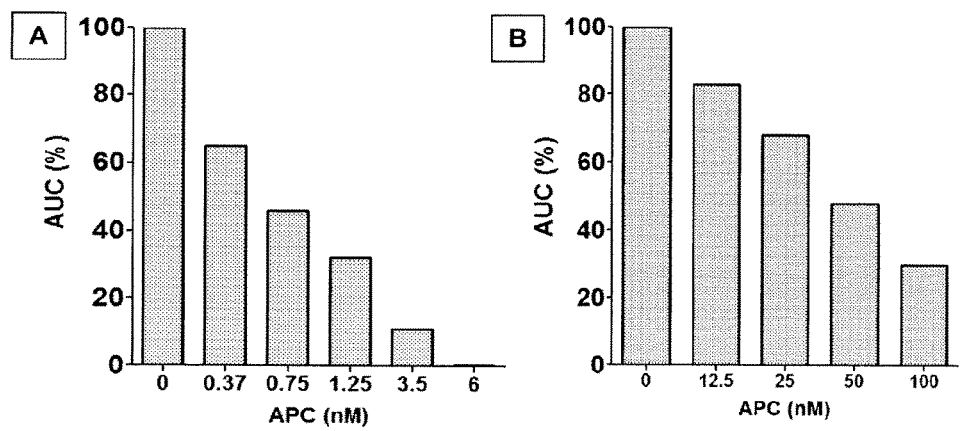
Figure 14. Suppression of thrombin generation by rhAPC plasma – dose response. Thrombin generation was determined in A) normal human plasma and B) mouse plasma in the presence of increasing of rhAPC. Thrombin generation was expressed as area under curve AUC.

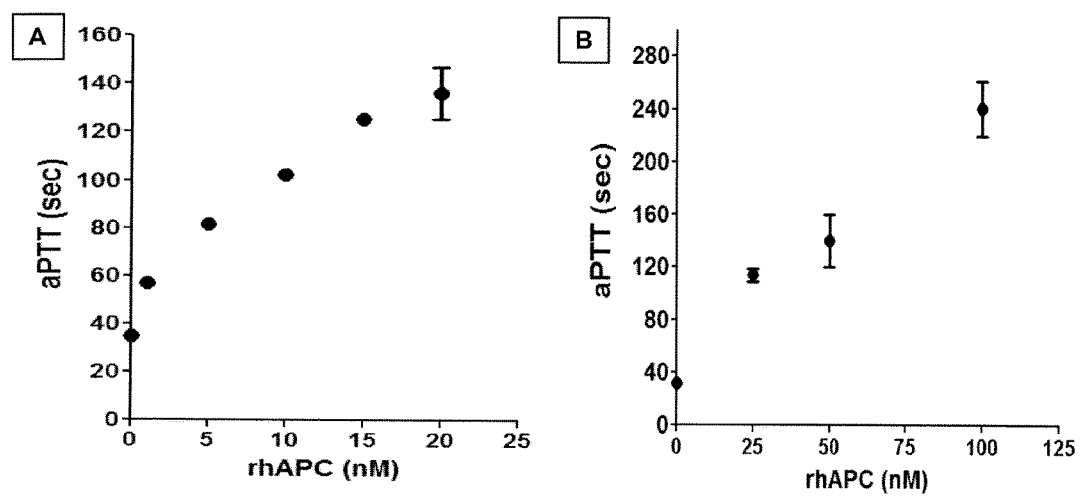
Figure 15. APTT. Prolongation of aPTT clotting times in plasma by rhAPC – dose response. APTT was determined in A) normal human plasma and B) murine plasma after supplementation with increasing concentrations of rhAPC (n=2-5). Error bars represent standard error of the mean.

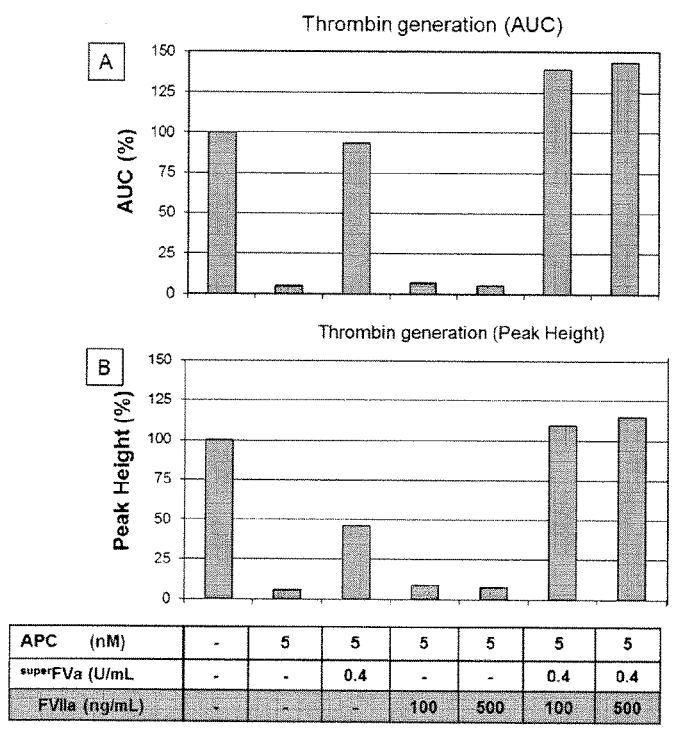

Figure 16. Rescue of APC-induced reduction of thrombin generation in human plasma. Thrombin generation was determined in normal human plasma as A) Area Under the Curve (AUC) and B) Peak Height in the presence of rhAPC. For rescue of thrombin generation superFVa and rhFVIIa were applied either alone or in combination.

Results: rhFVIIa alone at increasing concentrations had no effects on thrombin generation, while superFVa corrected thrombin generation to levels to those of normal human plasma.

Adding trace amounts of rhFVIIa (100 ng/mL) to superFVa increased thrombin generation by approximately 50% avove normal human plasma.

This experiment provides proof-of-principle that the combination of rhFVIIa with superFVa synergistically increased thrombin generation suppressed by APC in human plasma.

Remark: A dose finding study to determine lowest optimal concentration ranges of superFVa in combination with rhFVIIa to correct thrombin generation to normal was not yet done in the interest of time.

Figure 17 Effect of anti-FVIII antibody (inhibitor) on the clot lysis time of normal human plasma
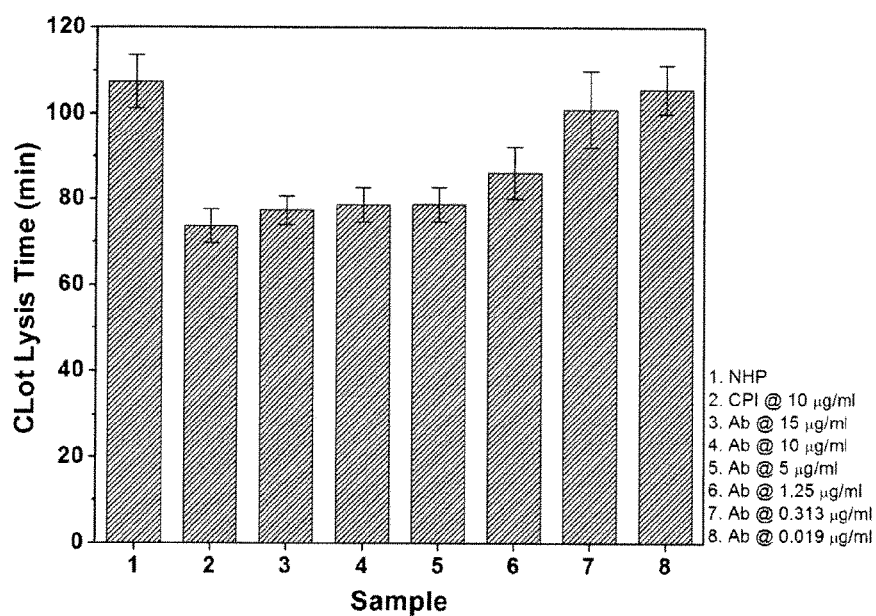

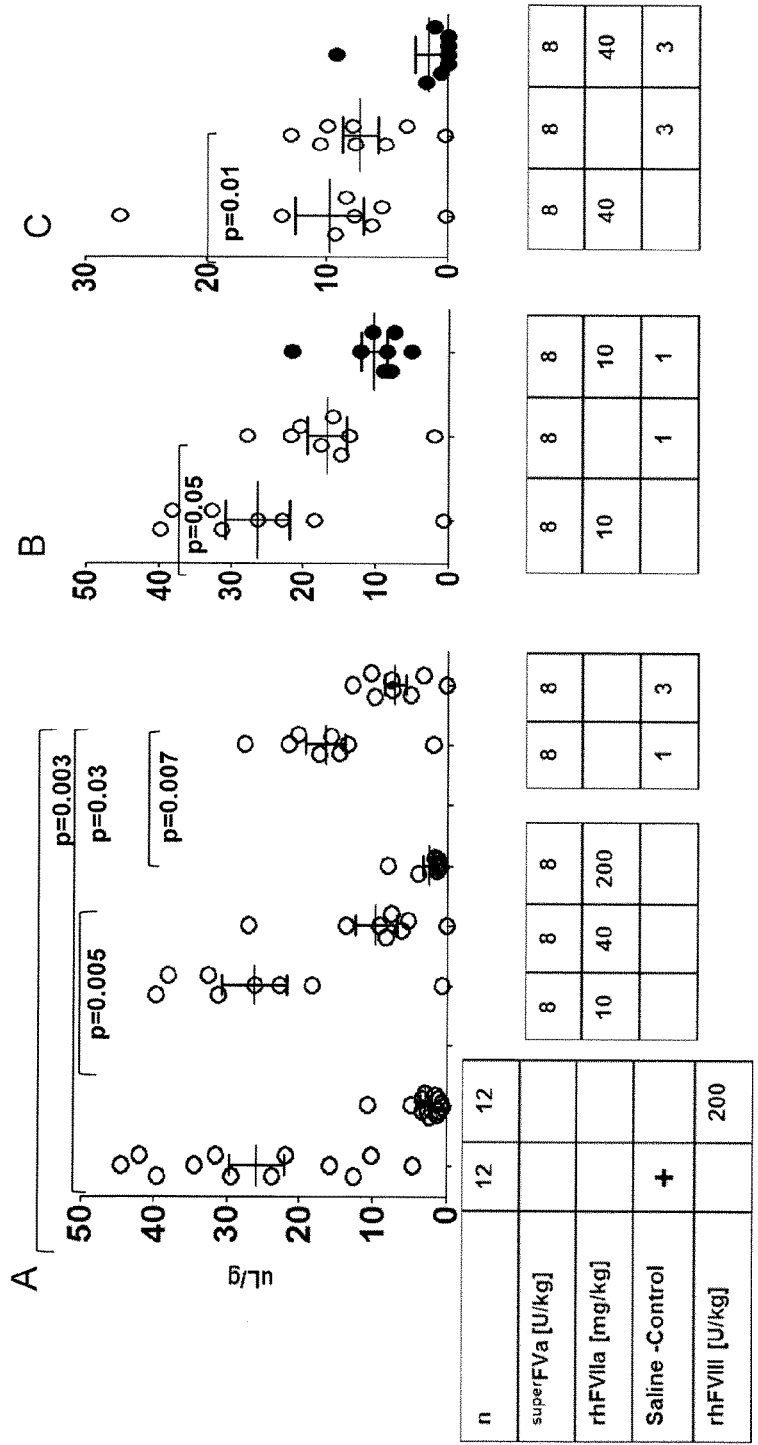

Figure 25.

Bleed correction following injection of rhFVIIa combined with $^{super}$FVa is similar to bleed correction with FVIII. FVIII-deficient mice were injected intravenously with saline, rhFVIII, increasing doses of $^{super}$FVa, rhFVIIa, or rhFVIIa in combination with $^{super}$FVa (1 Unit = activity of 20 nM wild-type FVa in the prothrombinase assay). Bleeding was determined during 20 minutes after tail clip and expressed as blood loss in μl blood per gram mouse. Error bars represent SEM. Blood loss in mice injected A) with saline, rhFVIII and with increasing doses of $^{super}$FVa or rhFVIIa, B) with low dose or C) medium dose of $^{super}$FVa or rhFVIIa alone and in combination.

Figure 31

[A]

| NHP with anti-FVIII Antibody | | | | |
|---|---|---|---|---|
| | superFVa (nM) | | rhFVIIa (nM) | |
| | 0 | 0.37 | 0 | 0.37 |
| rhFVIIa (nM) | 40 | 0.04 | - | - |
| superFVa (nM) | - | - | 3.33 | 0.37 |

Figure 33
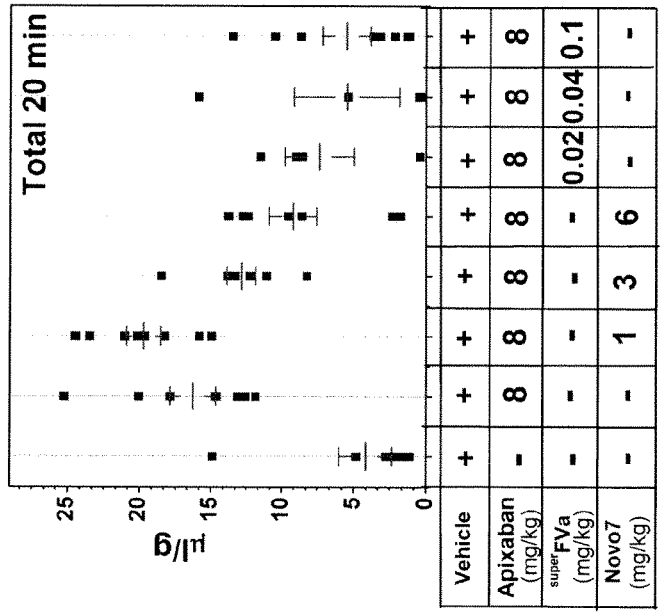
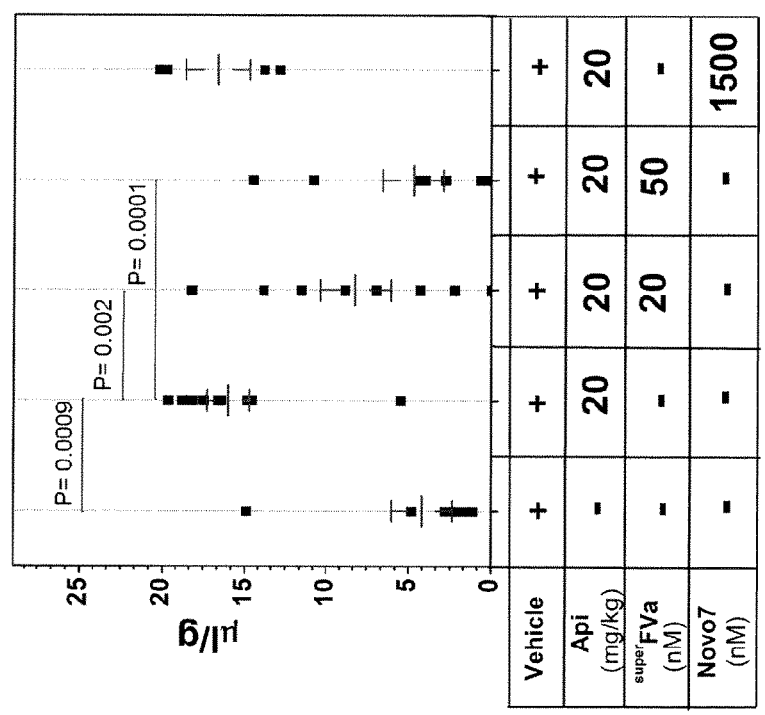

THERAPY FOR TREATMENT OR PREVENTION OF CONDITIONS ASSOCIATED WITH BLEEDING OR HYPOCOAGULATION

RELATED APPLICATIONS

This application is a 371 National Stage of International Application No. PCT/US2014/063898, filed Nov. 4,2014, which claims priority to U.S. Provisional Application No. 61/899,544, filed on Nov. 4, 2013, and U.S. Provisional Application No. 61/944,915, filed on Feb. 26, 2014, the contents of all of which are incorporated by reference herein in their entireties.

GOVERNMENT RIGHTS IN THE INVENTION

This invention was made with government support under NIH grant HL021544 and HL104165 awarded by the National Institutes of Health (NIH). The government has certain rights in the invention.

The sequence listing file named "41112o1001.txt," having a size of 34,530 bytes and created May 4, 2016, is hereby incorporated by reference in its entirety.

FIELD OF THE INVENTION

The present application generally relates to methods and compositions for use in such methods, for preventing or treating bleeding and/or hypocoagulation in an individual in need thereof by administering a therapeutically effective amount of Factor Va (FVa), preferably an activated Protein C (APC) resistant FVa, e.g., $^{super}$FVa, alone or in combination with Factor VIIa (FVIIa), preferably a recombinant FVIIa, more preferably rhFVIIa, e.g. (NovoSeven®), or another variant of recombinant FVIIa, e.g., one exhibiting improved half-life or increased activity; or another procoagulant or pro-hemostatic agent, wherein the combination preferably elicits a synergistic effect on thrombin generation relative to the FVa or FVIIa or other procoagulant or pro-hemostatic agent when administered alone to a subject in need thereof. Also, the invention relates to the use of FVa, preferably an APC resistant FVa, alone or in combination with a FVIIa, such as NovoSeven® or another variant thereof, e.g., one possessing improved half-life or activity, or another procoagulant or pro-hemostatic agent to treat or prevent bleeding due to excessive APC generation or administration.

BACKGROUND

Bleeding disorders, and particularly congenital or acquired deficiencies in coagulation factors, are typically treated by factor replacement. Bleeding disorders can be congenital or acquired. Coagulation disorders include hemophilia, a recessive X-linked disorder involving a deficiency of coagulation factor VIII (hemophilia A) or factor IX (hemophilia B), and von Willebrand's disease, a rare bleeding disorder involving a severe deficiency of von Willebrand factor. Hemophilia C is a milder form of hemophilia caused by a deficiency in factor XI. It is usually asymptomatic, but factor replacement therapy may be required during surgery.

Acquired coagulation disorders can be caused by inhibitory antibodies (often called "inhibitors") against blood coagulation factors, such as Factor VIII (FVIII), von Willebrand factor, Factors (F) IX, V, XI, XII and XIII; such inhibitors can arise against exogenously infused FVIII or FIX, or in the setting of autoimmunity.

Acquired coagulation disorders may also arise in individuals without a previous history of bleeding as a result of a disease process. For example, acquired coagulation disorders may be caused by hemostatic disorders such acute trauma, administration of anticoagulants, infection, or liver disease (optionally one associated with decreased synthesis of coagulation factors), all of which are associated with decreased synthesis of coagulation factors. For example, acquired coagulation disorders may be due to disease or genetic mutations associated with increased levels of soluble thrombomodulin and fragments thereof (see Langdown J, Luddington R J, Huntington J A, Baglin T P, A hereditary bleeding disorder resulting from a premature stop codon in thrombomodulin (p.Cys537Stop). Blood. 2014 Sep. 18; 124 (12):1951-6. doi: 10.1182/blood-2014-02-557538), the disclosure of which is incorporated herein by reference in its entirety).

Trauma is the leading cause of death in people younger than 45 years, with hemorrhage accounting for nearly half of these deaths within several hours (see Cothren C C, et al. Worl J Surg 2007; 31:1507-1511, the disclosure of which is expressly incorporated by reference herein). Traumatic bleeding and coagulopathy are mediated by undue activation of Protein C (PC), which in turn degrades activated (a) FV, an important clotting factor molecule (see Daniel Frith and Karim Bohi; Curr Opin Crit Care 2012, 18:631-636; and Chesebro B B, et al. 2009; Shock; 32: 659-665, the disclosures of which are expressly incorporated by reference herein). Outside of massive blood component transfusion, there is no efficacious clotting factor replacement available.

Increased risk of bleeding is also observed in patients receiving therapy with a variety of anticoagulants and there is a general unmet need for prohemostatic agents that reduce bleeding risk. Specifically, there is no effective treatment available against bleeding caused by the novel anticoagulants (NOACs) that directly inhibit Factor Xa (FXa) or thrombin [1, 2]. NOACs are increasingly prescribed for treatment and prevention of venous thromboembolism as well as prevention of strokes in the setting of atrial fibrillation, and are expected to supersede warfarin in the near future. This is because NOACs demonstrated at least equal efficacy compared to warfarin without the need of frequent patient monitoring and dose adjustments according to prothrombin times as is necessary for warfarin [3-8]. However, as with warfarin, major or clinically relevant bleeding is a consequence of treatment with NOACs, and both cause bleeding at a rate of ~5%/year with a fatality rate of ~5-15% [3-8]. For warfarin-induced bleeding the administration of plasma products or prothrombin complex concentrates (PCCs) is effective to achieve hemostasis [9, 10], but there are no antidotes against NOAC-induced bleeding available at current. Interventions with plasma products or PCCs in patients with NOAC-related bleeding are generally perceived as ineffective. Data are limited to in vitro studies, animal models and healthy human volunteers where plasma products or PCCs demonstrated only partial and inconsistent correction of in vitro hemostasis parameters as well as poor or no bleed reduction in animal models [2]. Moreover, intervention with rhFVIIa (NovoSeven®), approved for bleed control in patients with hemophilia and inhibitors and often used off-label for traumatic or surgical bleeding [11, 12], seems ineffective for NOAC- and warfarin-induced bleeding. Only minor corrections of in vitro hemostasis parameters were achieved with rhFVIIa (NovoSeven®) in healthy volunteers exposed to NOACs [13], and no effects on hemostasis were present in patients treated with warfarin undergoing skin biopsies [14].

Therefore, risk of bleeding and adequate prevention or control of bleeding episodes remains a major concern for these classes of drugs. The lack of clinical options to reverse bleeding associated with NOACs has spurred investigations into novel specific antidotes. As such, the reversal properties of thrombin double mutant, W215A/E217A, that shortens direct thrombin inhibitor-associated aPTT prolongation [15] and the dabigatran-specific humanized monoclonal antibody fragment aDabi-Fab were recently reported [16]. A catalytically inactive FXa that retains the ability to bind direct FXa inhibitors is in clinical development in healthy volunteers [17].

Moreover, there is currently no effective and/or approved treatment for bleeding as a common side effect of NOACs. Neither plasma products, rhFVIIa nor prothrombin complex concentrates have demonstrated clinical efficacy to rescue bleeding, but are frequently used in desperate situations absent any other treatments available.

There is also no effective treatment for other severe bleeding situations such as in hemorrhagic stroke or shock, serious injury, or perisurgically Hemophilia is characterized by either a deficiency of FVIII or FIX, known as Hemophilia A or B, respectively. Severe hemophilia manifests with spontaneous joint, muscle and intracranial bleeding, while bleeding in mild or moderate hemophilia usually only occurs with hemostatic challenge such as trauma or surgery. Prior to the 1960s, hemophiliacs usually died as infants. With the advent of safe clotting factor preparations the median life span is now comparable to the general population (1), and the growing number of aging hemophiliacs has unmasked a new need to optimize strategies of clotting factor replacement therapies to decrease comorbidities inherent to bleeding such as burden of hemophilic arthropathy.

Conventional therapy for hemophilia A and FVIII inhibitor patients is accomplished by therapeutics like recombinant FVIII or procoagulant bypassing agents, for example FEIBA or recombinant FVIIa. Although effective, development of inhibitory antibodies which render the therapy ineffective is a common occurrence. Also, FVIIa and FEIBA as therapeutics for the treatment of FVIII inhibitor patients have quite short half-lives and so require frequent intravenous administration.

In fact, approximately 30% of hemophiliacs develop neutralizing inhibitory antibodies against exogenously administered FVIII (2), which is the most devastating complication of therapy since it leaves patients unresponsive to FVIII- or FIX-treatment. Immune tolerance induction (ITI) to eradicate inhibitors can take up to 2 years (median of 6 months) and is successful in only approximately 70% of cases (3). During this time and, life-long thereafter if ITI was not successful, patients are vulnerable to fatal bleeding, and are at high risk of developing debilitating arthropathy with poor quality of life (4).

FVIIa-based clotting factor preparations were developed to treat patients with inhibitors by rescuing bleeding through bypassing the need for intrinsic FVIIIa-, FIXa-, and FXIa-mediated thrombin amplification at the site of injury. At supraphysiological levels FVIIa accelerates thrombin generation based on direct activation of FX via tissue factor (TF)-dependent pathways or independently of TF on the surface of platelets (5, 6).

Unfortunately, treatment with FVIIa-based bypassing agents remains suboptimal and in clinical reality often unsuccessful (4, 7, 8). This makes new treatment strategies to provide more sustained thrombin formation highly desirable and have inspired investigations of several new clotting agents. These include novel FVIIa variants with increased catalytic activity and half-life (9-11), engineered FIX-molecules with enhanced ability to bind and activate FX (12), and engineered zymogen-like FX variants that become active upon engaging FVa in the prothrombinase complex (13, 14). A research group including the present inventors recently proposed "FVa activity augmentation" as another attractive alternative bypassing strategy. FVa is an important cofactor in the prothrombinase complex and enhances the rate of thrombin generation approximately 10,000-fold (15), but is also rapidly inactivated by Activated Protein C (APC) (16). Since $^{super}$FVa is APC-inactivation resistant due to mutations of all three APC cleavage sites at Arg506, Arg306 and Arg679 and at glycosylation site Ser2183, the interdomain disulfide bond (His609Cys-Glu1691Cys) connecting the A2 and A3 domains (A2-SS-A3) and elimination of the glycosylation site at Asn2181 due to mutation of Ser2183Ala (16), it is an ideal molecule for "FVa activity augmentation". This molecule demonstrated superior procoagulant properties in FVIII-deficient plasma when compared to other FVa variants and was able to control bleeding in a mouse model of Hemophilia A (von Drygalski A, et al. JTH 2014; 12:363-372), as well as in a mouse model of acquired Hemophilia A, where anti-FVIII antibodies are injected into wild-type mice to cause bleeding. Effects of $^{super}$FVa were enhanced when combined with rhFVIIa.

The present invention addresses these needs and provides novel therapy and therapeutic regimens for treating conditions associated with bleeding.

SUMMARY OF THE INVENTION

There is a need for improved therapeutics and treatment regimens for treating bleeding disorders, which are safe, convenient and effective. Also, there is a need for therapies and therapeutic compositions which effectively treat or prevent APC-associated bleeding, e.g., as the result of overexpression or hyperactivation of APC or the administration of anticoagulants such as APC. The present invention provides such an improved therapeutic regimen for alleviating such problems as well as novel compositions for use therein.

As discussed infra, the inventors hypothesized that $^{super}$FVa, an engineered FVa-variant that potently normalizes hemostasis in hemophilia, fits the criteria for a prohemostatic biologic and may be beneficial for bleeding associated with serious injury or treatment of NOACs. $^{super}$FVa has enhanced specific activity compared to wild type FVa due to an engineered disulfide bond (Cys609-Cys1691) between the A2 and A3 domains (FV (A2-SS-A3)) and, its biological activity is augmented by mutations of the Activated Protein C (APC) cleavage sites (Arg506/306/679Gln) and the elimination of the glycosylation site at Asn2181 due to mutation of Ser2183Ala. As a result of these modifications, $^{super}$FVa was found to be highly resistant to APC inactivation with superior hemostatic properties in hemophilic plasma compared to other FVa variants and efficiently prevented bleeding in a hemophilic mouse model (von Drygalski A, et al., Improved hemostasis in hemophilia by means of an engineered factor Va mutant. J Thromb Haemost; 2014; 12:363-372). Moreover, in hemophilia plasma with inhibitors $^{super}$FVa surprisingly exhibited synergistic effects in combination with rhFVIIa on thrombin generation and prolongation of clot lysis (Bhat V. and von Drygalski A, et al; unpublished data). $^{super}$FVa was also efficient to restore hemostasis parameters of human APC-treated plasma while rhFVIIa or PCCs would not, and could abrogate APC-induced bleeding and death following tail clip or liver laceration in wild-type mice (von Drygalski A, et al; An engineered FVa prevents bleeding induced by anticoagulant wild-type Activated Protein C. PLOS One; 2014 Aug. 15; 9(8):e104304 (doi: 10.1371/journal.pone.0104304. eCollection 2014)). As discussed herein, $^{super}$FVa has demonstrated superior hemostatic properties in human plasma spiked with NOACs as well as significant bleed reduction in mice treated with NOACs. Moreover, as provided herein, the prohemostatic properties of $^{super}$FVa were enhanced when combined with, e.g., PCCs or rhFVIIa or FIXa or FXa.

Based on these observations, the inventors concluded that $^{super}$FVa, as an engineered FVa-variant that potently normalizes hemostasis in hemophilia and in APC-induced bleeding, potentially would fit the criteria for a prohemostatic biologic that could improve bleeding induced by NOACs, such as FXa inhibitors. Therefore, in one aspect, the present invention provides a therapy for preventing or treating a bleeding related condition associated with, induced by or mediated by a novel oral anticoagulant drug (NOAC), comprising the use of $^{super}$FVa or other APC-resistant FVa alone or in combination with the NOAC.

Additionally, based thereon, the invention in part relates to the use of FVa, preferably an APC resistant FVa, alone or in combination with a FVIIa, such as NovoSeven® or another variant thereof, e.g., one possessing improved half-life or activity to treat or prevent bleeding due to excessive APC generation or APC or anticoagulant administration or synthetic small molecules and biologics.

Also, the invention relates to the administration of $^{super}$FVa alone or in association with FVIIa to reverse or inhibit APC-associated bleeding, e.g., in individuals with inflammatory disorders, sepsis disease, wound healing, and/or disease due to exposure to nuclear radiation.

It is an object of the present invention to provide a novel therapeutic regimen for treating subjects in need of enhanced blood coagulation, e.g., those with genetic and acquired bleeding disorders; or hemophilia with inhibitors; or a hemostatic disorder; or unexplained bleeding, which comprises the use of FVa alone or in combination with FVIIa. Preferably, the FVa contains one or more natural (e.g., Leiden, Cambridge, or Hong Kong mutations) or genetically engineered mutations that render it resistant to APC (more resistant to APC than an otherwise identical FVa polypeptide lacking the mutations). The natural mutations preferably are at one or both of amino acid positions 306 and 506, preferably Arg306Gln and Arg506Gln. The genetically engineered mutations preferably occur at positions position 306, 506, 679, 1491, 1691, 1736 and 2183 and render the FVa resistant to APC cleavage.

More preferably, the FVa is a "$^{super}$FVa" that has specific mutations that render the FVa particularly APC resistant, i.e., one or all of the mutations R306Q, R506Q, H609C, R679Q, Deletion 810-1489, G1491P, E1691C, M1736V, and S2183A, with or without the formation of an intramolecular interdomain disulfide bridge between C609 and C1691. Most preferably, $^{super}$FVa has mutations at R306Q, R506Q, H609C, and R679Q and/or mutations at G1491P, E1691C, M1736V, and S2183A, with or without the formation of an intramolecular interdomain disulfide bridge between C609 and C1691, and deletion of amino acids 810-1489 (relative to wt FVa).

Also, preferably, the FVIIa is rhFVIIa (NovoSeven®) or another variant of FVIIa, preferably one having enhanced half-life and/or activity, e.g., as a result of mutagenesis and/or attachment to moieties known to enhance half-life such as water soluble polymers including polyethylene glycol. The subject combination and therapeutic regimen using such combination has been found to elicit a synergistic effect on clotting, i.e., coagulation, relative to presently available treatment regimens for treating bleeding or hypocoagulation disorders such as hemophilia by synergistically promoting the generation of thrombin.

More specifically, it is an object of the invention to provide methods of promoting blood coagulation or the reduction or prevention of bleeding in an individual in need thereof comprising the administration of an effective amount of FVa with or without FVIIa. Preferably, the relative dosage amounts will elicit a synergistic effect on clotting or coagulation by synergistically promoting the generation of thrombin. (Exemplary contemplated dosing schedules for the treatment of exemplary indications wherein the subject combination will be of use in treating or preventing hypocoagulation or bleeding are set forth infra).

It is another object of the invention to provide methods of promoting blood coagulation in an individual in need thereof consisting of the administration of an effective amount FVa alone or in combination with FVIIa, i.e., wherein the only blood coagulation promoting agents administered are FVa, preferably a $^{super}$FVa or other protease resistant FVa, and FVIIa.

It is another object of the invention to provide methods of promoting blood coagulation in an individual in need thereof comprising the administration of FVa, preferably a $^{super}$FVa (mutated to be highly APC resistant) alone or with rhFVIIa (NovoSeven®) which in association synergistically promote thrombin generation, or in combination with other FVIIa and optionally in association with another active agent or procoagulant or pro-hemostatic agent, e.g., FXI, FXII, prekallikrein, high molecular weight kininogen (HMWK), FV, FVII, FVIII, FVIIJa, FIX, FX, FXIII, FH, fresh frozen plasma, and von Willebrand factor or activated forms of the factors listed above or a non-anticoagulant sulfated polysaccharide (NASP) such as pentosan polysulfate (PPS), fucoidan, N-acetyl-heparin (NAH), N-acetyl-de-O-sulfated-heparin (NA-de-o-SH), de-N-sulfated-heparin (De-NSH), de-N-sulfated-acetylated-heparin (De-NSAH), periodate-oxidized heparin (POH), chemically sulfated laminarin (CSL), chemically sulfated alginic acid (CSAA), chemically sulfated pectin (CSP), dextran sulfate (DXS) and heparin-derived oligosaccharides (HDO).

It is another object of the invention to provide methods of preventing bleeding or promoting blood coagulation in an individual in need thereof comprising the administration of an effective amount of FVa alone or in combination with FVIIa, preferably $^{super}$FVa and rhFVIIa, wherein the FVa alone or in combination with FVIIa is administered by a means selected from orally, via injection (subcutaneously, intravenously or intramuscularly), by infusion, by inhalation, or locally.

It is another specific object of the invention to provide methods of promoting blood coagulation in an individual who has a genetic disorder associated with abnormal bleeding. In one embodiment, the invention provides methods of promoting blood coagulation in an individual who has a genetic disorder associated with bleeding, e.g., hemophilia or more specifically hemophilia A, hemophilia B, and von Willebrand's disease.

It is another object of the invention to provide methods of promoting blood coagulation in an individual in need thereof, e.g., one who has a genetic coagulation disorder, e.g., in which blood coagulation factors (such as FV, FVIII, prothrombin, thrombomodulin, Protein C and Protein S, antithrombin, homocysteine, or lipoprotein(a)), are absent, present at lower than normal levels or present at normal levels with impaired function due to a genetic mutation or polymorphism; or an acquired coagulation disorder, e.g., one which confers autoimmunity against blood coagulation factors, such as FVIII, von Willebrand factor, factors IX, V, XI, XII and XIII; or hemophilia with inhibitors; or a hemostatic disorder such as caused by liver disease, optionally one associated with decreased synthesis of coagulation factors; dysmenorrhea; or unexplained bleeding.

It is another specific object of the invention to provide methods of preventing bleeding or promoting blood coagulation in an individual in need thereof, wherein the individual has or is at risk of bleeding as the result of trauma, surgery, dental procedure or another invasive procedure, or exhibits unexplained bleeding. The treated subject may have or is at risk of developing APC-associated or APC-induced or APC-mediated bleeding due to, e.g., hemorrhagic stroke or shock, trauma, surgery or dysmenorrhea.

It is another object of the invention to provide methods of promoting blood coagulation in an individual in need thereof comprising the administration of a synergistically effective amount of FVa and FVIIa, wherein said FVa and FVIIa are contained in the same composition or different compositions and are administered together or separately, at the same or different times and in either order. Typically, administration is effected at the same time or proximate so as to achieve the desired synergistic effect on coagulation and thrombin generation. For synergy, dosing will be dependent on the in vivo half-life ($T_{1/2}$) for FVIIa and the particular FVa used in the treatment method, preferably a $^{super}$FVa according to the invention. The $T_{1/2}$ for $^{super}$FVa or another FVa, e.g., a FVa variant, e.g., one possessing enhanced stability, or half-life may be determined by known methods. The $T_{1/2}$ for FVIIa is ~2.5 hr. Based on this $T_{1/2}$ and based on its anticipated $T_{1/2}$, $^{super}$FVa preferably will be dosed within $4 \times T_{1/2}$ of FVIIa, preferably within $1 \times T_{1/2}$ of FVIIa, i.e., administration from about every 10 hours to about 2.5 hours.

It is a specific object of the invention to provide methods of promoting blood coagulation in an individual in need thereof comprising the administration of an effective amount of FVa alone or in combination with FVIIa. The FVa is preferably resistant to APC degradation, e.g., the FVa contains one or more naturally occurring or genetically engineered mutations that render the FVa more resistant to APC than an otherwise identical FVa polypeptide lacking said one or more mutations. Even more preferably, the FVa is a $^{super}$FVa comprising one or all of the mutations Arg306Gln, Arg506Gln and Arg679Gln and/or the introduction of cysteine residues at position 609 and/or 1691 (with and without an intramolecular interdomain disulfide bridge inserted between those cysteine residues) and/or the mutant comprises one or more natural mutations (e.g., Leiden mutation) that render the FVa APC resistant, e.g., substitution mutation at position 506, preferably Arg506Gln and/or the FVa mutant comprises a mutation at one or more sites selected from position 306 (e.g., the Cambridge substitution Arg306Thr, the Hong Kong substitution Arg306Gly or, preferably, Arg306Gln), 506, 679, and 1736 that render the FVa resistant to APC cleavage and/or elimination of the glycosylation site at Asn2181 due to mutation of Ser2183Ala mutation. Most preferably, the $^{super}$FVa comprises a sequence at least 90% identical, at least 95% identical or identical to SEQ ID NO:4 and including an intramolecular interdomain disulphide bridge between cysteine residues at position 609 and 1691.

Also, the FVIIa may be wild-type or a variant hFVIIa such as NovoSeven® or another FVIIa variant possessing enhanced activity and/or half-life as a result of mutagenesis and/or the attachment of moieties that increase in vivo half-life or activity such as water soluble polymers such as polyethylene glycols and the like. Preferably, FVIIa comprises a sequence at least 90% identical, at least 95% identical or identical to SEQ ID NO:2.

It is another object of the invention to provide compositions for use in the subject therapeutic regimens for promoting blood coagulation in an individual in need thereof, i.e., a composition for administration to a patient having or at risk of developing abnormal bleeding or hypocoagulation which composition comprises a prophylactically or therapeutically effective amount of FVa with or without FVIIa. Preferably, when the said FVa and FVIIa are administered in combination, they elicit a synergistic effect on the treatment or prevention of bleeding and/or enhanced coagulation by synergistically promoting the generation of thrombin. In a particular embodiment, the compositions, when administered to an individual in need thereof, are capable of eliciting a synergistic effect on coagulation or the prevention of bleeding by synergistically promoting the generation of thrombin or restoring resistance of the clot or increasing the clot lysis time or by restoring the activation of Thrombin Activatable Fibrinolysis Inhibitor (TAFI).

In preferred embodiments, the FVa in the composition is one which is resistant to APC degradation, e.g., it contains one or more natural or genetically engineered mutations that render the FVa more resistant to APC than an otherwise identical FVa polypeptide lacking said one or more mutations. Preferably, the FVa is a $^{super}$FVa comprising one or all of the mutations Arg306Gln, Arg506Gln and Arg679Gln and/or is mutated to include cysteine residues at position 609 and/or 1691, with and without an intramolecular interdomain disulfide bridge inserted between the two cysteine resides, and/or contains one or more natural mutations (e.g., Leiden mutation) that render the FVa APC resistant, e.g., Leiden mutation is at the amino acid position numbered 506 (in the mature protein), preferably Arg506Gln, and/or it comprises a mutation at one or more sites selected from position 306, 506, 679, and 1736 that render the FVa resistant to APC cleavage and/or the FVa contains a mutation that alters glycosylation, such as a Ser2183Ala mutation. Most preferably, the $^{super}$FVa comprises a sequence at least 90% identical, at least 95% identical or identical to SEQ ID NO:4 and including an intramolecular interdomain disulphide bridge between cysteine residues at position 609 and 1691.

Again, the FVIIa preferably comprises rhFVIIa, e.g., wild-type or a variant possessing improved activity and/or half-life such as (NovoSeven® or another variant. Preferably, FVIIa comprises a sequence at least 90% identical, at least 95% identical or identical to SEQ ID NO:2. In preferred embodiments these compositions are adopted for administration by a route selected from orally, via injection (e.g., subcutaneously, intravenously or intramuscularly), by infusion, or locally.

It is a specific object of the invention to provide a combination therapy for treating a bleeding related condition comprising the combined use of $^{super}$FVa or other APC-resistant FVa and at least one of recombinant FVIIa, recombinant FIXa, recombinant FXa, a prothrombin complex concentrate, or a combination thereof in order to synergistically improve thrombin generation or hemostasis potential.

It is another specific object of the invention to prevent and/or reduce bleeding induced by the use of novel oral anticoagulant drugs (NOACs) recently developed for treatment and prevention of thrombotic disorders and stroke, such as direct Xa inhibitors such as Rivaroxaban and Apixaban and Edoxaban, or a combination thereof, as well as direct thrombin inhibitors such as Dabigatran, and optionally further including the use of Kcentra™, in combination with $^{super}$FVa.

In a related aspect, the invention provides $^{super}$FVa or other APC-resistant FVa variants alone or as a co-therapeutic with recombinant FVIIa or other pro-hemostatic agents (e.g., 3-factor PCC, 4-factor PCC, activated PCC, FEIBA, fresh frozen plasma, FVa, FIXa, FXa) to provide an antidote for bleeding due to a subclinical dose, clinical dose and/or overdose of NOAC.

In addition, the invention provides the use of $^{super}$FVa alone or in combination with other therapeutics (e.g., recombinant FVIIa or other pro-hemostatic agents (e.g., 3-factor PCC, 4-factor PCC, activated PCC, FEIBA, fresh frozen plasma, FVa, FIXa, FXa) to prevent or treat bleeding in other indications such as hemorrhagic stroke or shock, trauma or surgery, including prophylaxis for surgery in patients that have been treated with NOACs (e.g., direct Factor Xa inhibitor and/or thrombin inhibitor).

It is another object of the invention to provide synergistic combinations and uses thereof comprising FVIIa; FX and FXa; FIX and FIXa; prothrombinase complex concentrate (PCC); 3-factor PCC; 4-factor PCC; activated PCC; Factor eight bypassing activity (FEIBA); fresh frozen plasma; and FV or FVa with $^{super}$FVa or other FVa variants in order to provide improved efficacy over the agents alone in the treatment and prevention of bleeding episodes and bleeding related conditions.

It is another object to demonstrate the synergism of rhFVIIa or prothrombin complex concentrates and $^{super}$FVa in plasma containing NOACs.

It is yet another object of the invention to provide an isolated nucleic acid molecule encoding an activated form of FV comprising SEQ ID NO:4; a host cell comprising the isolated nucleic acid, e.g., SEQ ID NO:4; and methods for recombinant production of an activated form of FV, comprising culturing the host cell comprising the isolated nucleic acid under conditions suitable for FV production and optionally isolating and purifying said activated form of FV.

DETAILED DESCRIPTION OF THE FIGURES

FIGS. 1A and B contains an experiment showing the synergistic effects of FVIIa and $^{super}$FVa in FVIII-deficient plasma. Thrombin generation was determined as ETP and peak height in FVIII-deficient plasma supplemented with increasing concentrations of $^{super}$FVa in the absence or presence of a fixed concentration of rhFVIIa (NovoSeven®, 25 ng/mL). (A) Representative example of ETP at increasing concentrations of $^{super}$FVa in the absence (top panel) or presence of rhFVIIa (bottom panel). (B) ETP (top panel) and peak height (bottom panel) achieved with increasing concentrations of $^{super}$FVa in the absence (black curve) or presence of rhFVIIa (red curve). Endogenous Thrombin Potential; ETP. $^{Super}$FVa; SFVa. Error bars represent standard error of the mean (n≥5).

FIGS. 2A and B contain the results of an experiment that shows the synergistic effect of FVIIa and $^{super}$FVa in FVIII-deficient plasma. Thrombin generation was determined as ETP and peak height in FVIII-deficient plasma supplemented with increasing concentrations of rhFVIIa (NovoSeven®) in the absence or presence of a fixed concentration of $^{super}$FVa (0.59 µg/ml). (A) Representative example of ETP at increasing concentrations of rhFVIIa in the absence (top panel) or presence of $^{super}$FVa (bottom panel). (B) ETP (top panel) and peak height (bottom panel) achieved with increasing concentrations of rhFVIIa in the absence (black curve) or presence of $^{super}$FVa (red curve). Endogenous Thrombin Potential; ETP, $^{Super}$FVa; SFVa. Error bars represent standard error of the mean (n≥5).

FIGS. 3A and B contain the results of an experiment that shows the synergistic effect of FVIIa and $^{super}$FVa in Normal Human Plasma (NHP) with anti-FVIII antibody (inhibitor). Thrombin generation was determined as ETP (top panels) and peak height (bottom panels) in normal human plasma supplemented with 1.25 µg/ml anti-human FVIII-antibody. (A) Thrombin generation with increasing concentrations of $^{super}$FVa in the absence (black curve) or presence of a fixed dose of rhFVIIa (NovoSeven®, 25 ng/ml) (red curve) concentration. (B) Thrombin generation with increasing concentrations of rhFVIIa in the absence (black curve) or presence of a fixed dose of $^{super}$FVa (red curve) concentration. Endogenous Thrombin Potential; ETP. $^{Super}$FVa; SFVa. Error bars represent standard error of the mean (n≥5).

FIGS. 4A and B contain the results of an experiment that shows the synergistic effect of FVIIa and $^{super}$FVa in plasma of patients with congenital FVIII-deficiency and high titer anti-FVIII antibodies (inhibitors). Thrombin generation was determined as ETP (top panel) and peak height (bottom panel) in (A) plasma samples with inhibitors from 2 patients seen at the UCSD Hemophilia Treatment Center or (B) commercial plasma samples with inhibitors from 3 different patients. ETP was determined at 2 different concentrations of $^{super}$FVa or rhFVIIa, or combinations thereof. Inhibitor titers are expressed in BU. Pooled NHP served as control. Endogenous Thrombin Potential; ETP. Normal Human Plasma; NHP. BU; Bethesda Unit. Error bars represent standard error of the mean (n≥3).

FIGS. 5A and 5B contains the results of an experiment that shows the synergistic effect of $^{super}$FVa in the plasma of a patient with congenital FVIII-deficiency and high titer anti-FVIII antibodies treated with rhFVIIa (NovoSeven®) for acute joint bleeding. Plasma samples were obtained just before (open circles) and 5 minutes post infusion of rhFVIIa at 90 µg/kg (open squares) from 2 patients with BU-titers of 64 U/mL (Patient A) and 32 U/ml (Patient B), respectively. Thrombin generation was determined as ETP (top panel) or peak height (bottom panel) with increasing concentrations of $^{super}$FVa added to plasma samples ex vivo. Endogenous Thrombin Potential; ETP. BU; Bethesda Unit. Error bars represent standard error of the mean (n≥3).

FIG. 6 contains a Bethesda titer of GMA8015 anti-FVIII. FVIII inhibitory activity was measured according to a modified Nijmegen Bethesda assay according to the protocol described in Barrow and Lollar, J T H, 2006. 50% FVIII activity was remaining at 0.031 µg/ml of GMA8015. This results in 32,300 BU/mg of GMA8015.

FIG. 7 shows thrombin generation in normal human plasma with and without isotype antibody. Thrombin generation was determined in pooled normal human as endogenous thrombin potential (ETP) in normal pooled human plasma in the presence or absence of 1.25 µg/ml isotype antibody, expressed as area under the curve (top panel) and peak height (bottom panel). Error bars represent standard error of the mean (n≥3).

FIGS. 8A and 8B contain the results of experiments determining thrombin generation. In the experiments in Panel A and B this was respectively determined in A) using normal human plasma and B) using murine Balb/c plasma supplemented with rhFVa or rh$^{super}$FVa in the presence of rhAPC. Thrombin generation was expressed as area under curve (AUC) (n=4-6). Error bars represent standard error of the mean. * denotes statistical significance (all p-values <0.001).

FIG. 9A-C show aPTT correction. In the experiments in Panel A) aPTT clotting times were determined in human plasma in the presence of a) increasing concentrations of rhFVa or rh$^{super}$FVa in the presence of 10 nM rhAPC (n=4), and in Panel B) aPTT clotting times are depicted as a single data point at 10 nM rhAPC and 1 nM rh FVa variants, and in Panel C) aPTT clotting times were detected in murine plasma in the presence of rhFVa variants (n=10). Error bars represent standard error of the mean. * denotes statistical significance (all p-values <0.001).

FIG. 10 shows aPTT correction with FVa variants after intravenous injection of recombinant murine APC into Balb/C mice. Mice were injected intravenously with saline or rmAPC (0.5 mg/kg). Two minutes later blood was collected retroorbitally and whole blood APTT was determined immediately. In two groups of mice that were injected with APC whole blood was spiked ex vivo with either $^{super}$FVa or wt FVa (open triangles 1 U/mL, open circles 0.5 U/mL, closed triangles 0.05 U/mL) to determine the extent of APTT correction with both variants. Error bars represent standard error of the mean. * denotes statistical significance (all p-values <0.001).

FIG. 11A-C contains the results of experiments showing the correction of APC-induced bleeding by $^{super}$FVa in the murine tail clip model. Wild-type mice were injected intravenously with increasing doses of rhAPC or with saline. $^{super}$FVa was injected intravenously 2 minutes prior to APC at 2 concentrations. Bleeding after tail clip is expressed as blood loss in µl blood per gram mouse. Panel (A) shows blood loss during 20 minutes, and divided into (B) 1st 10 minutes and (C) 2nd 10 minutes after tail clip is depicted. Error bars represent SEM. * denotes statistical significance (p-value <0.05).

FIG. 12 contains the results of experiments showing the direct comparison of bleeding patterns following tail clip and liver laceration. FVIII-deficient mice were injected intravenously with saline (200 µL) or rhFVIII (50 U/kg; 200 µL) and subjected to tail clip or liver laceration. Wild-type Balb/c mice were injected with saline for baseline values. Blood loss in all groups of mice during 20 minutes was determined in both models.

FIG. 13A-C shows the results of experiments demonstrating the correction of APC-induced bleeding by the administration of $^{super}$FVa after liver laceration. Mice were injected intravenously with saline or plasma derived human APC at 1.25 mg/kg. $^{super}$FVa was injected intravenously 2 minutes prior to APC at 3.5 mg/kg. Bleeding after liver laceration is expressed as blood loss in µl blood per gram mouse. (A) Blood loss and (B) survival during 20 minutes. (C) Blood loss divided into $1^{st}$ 10 minutes (top panel) and $2^{nd}$ 10 minutes (bottom panel) after injury. Error bars represent SEM. * denotes statistical significance (p-value <0.01). ˆFour of 13 mice injected with APC died during the $1^{st}$ 10 minutes after injury (open circles). Three more mice died during the $2^{nd}$ 10 minutes, respectively (open rectangles) and are therefore excluded from bottom panel. Error bars represent standard error of the mean. * denotes statistical significance (all p-values ≤0.01).

FIGS. 14A and B contain the results of experiments showing suppression of thrombin generation by rhAPC plasma and the dose response. Thrombin generation was determined in A) normal human plasma and B) mouse plasma in the presence of increasing of rhAPC. Thrombin generation was expressed as area under curve AUC.

FIGS. 15A and 15B contain the results of experiments showing aPTT. Prolongation of aPTT clotting times in plasma by rhAPC and the dose response. aPTT was determined in A) normal human plasma and B) murine plasma after supplementation with increasing concentrations of rhAPC (n=2-5). Error bars represent standard error of the mean.

FIGS. 16A and 16B show the rescue of APC-induced reduction of thrombin generation in human plasma. Thrombin generation was determined in normal human plasma as A) Area Under the Curve (AUC) and B) Peak Height in the presence of rhAPC. For rescue of thrombin generation $^{super}$FVa and rhFVIIa were applied either alone or in combination.

FIG. 17 contains the results of a clot lysis assay performed to study the effect of anti-FVIII antibody on normal human plasma. Titration of anti-FVIII antibody showed that more than 5 µg/ml antibody was sufficient to decrease the clot lysis time to the level of TAFIa inhibitor (CPI) control.

FIGS. 18A and 18B contains the results of a clot lysis assay wherein 10 µg/ml antibody concentration was used to assess the effect of rhFVIIa and $^{super}$FVa individually and in combination on clot lysis of normal human plasma including an inhibitor against FVIII. As shown therein the rhFVIIa and $^{super}$FVa individually showed an enhancement of clot lysis time in normal human plasma incubated with 10 µg/ml of anti-FVIII antibody at higher concentration of 2 µg/ml and ~2-5 µg/ml, respectively.

FIGS. 19A and B contains the results of a clot lysis assay wherein rhFVIIa and $^{super}$FVa were used in combination. As shown therein, clot lysis time was observed to enhance to the level of normal plasma at a decreased concentration of rhFVIIa by two orders of magnitude and in $^{super}$FVa by more than an order of magnitude demonstrating a synergistic effect of both rhFVIIa and $^{super}$FVa on correcting the clot lysis time of normal human plasma (NHP) with inhibitors against FVIII.

FIGS. 20A and 20B show the synergistic effect of $^{super}$FVa and FVIIa in NHP treated with Rivaroxaban. Thrombin generation was determined as ETP and peak height in NHP in the presence of 200 nM Rivaroxaban. The effects on reversal of thrombin generation with rhFVIIa (2 µg/mL) alone, with $^{super}$FVa (400 nM) alone, or with combination of a fixed dose of rhFVIIa (2 µg/mL) and increasing doses of $^{super}$FVa (6.25-400 nM) were studied. (A) Representative example. (B) ETP (top panel) and peak height (bottom panel) as combined results from 3-5 independent experiments. rhFVIIa at 2 µg/mL corresponds to the expected plasma concentration after infusion of 90 µg/kg. The red dot represents ETP in NHP in the absence of rivaroxaban. Endogenous Thrombin Potential; ETP. Normal human plasma; NHP. $^{super}$FVa; $^S$FVa. Error bars represent standard error of the mean (n≥3).

FIGS. 21A and 21B show the synergistic effect of $^{super}$FVa and FVIIa in NHP treated with Apixaban. Thrombin generation was determined as ETP and peak height in NHP in the presence of 200 nM Apixaban. The effects on reversal of thrombin generation with rhFVIIa (2 µg/mL) alone, with $^{super}$FVa (400 nM) alone, or with combination of a fixed dose of rhFVIIa (2 µg/mL) and increasing doses of $^{super}$FVa (6.25 to 400 nM) were studied. (A) Representative example. (B) ETP (top panel) and peak height (bottom panel) as combined results from 3-5 independent experiments. rhFVIIa at 2 µg/mL corresponds to the expected plasma concentration after infusion of 90 µg/kg. The red dot represents ETP in NHP in the absence of apixaban. Endogenous Thrombin Potential; ETP. Normal human plasma; NHP. $^{super}$FVa; $^S$FVa. Error bars represent standard error of the mean (n≥3).

FIGS. 22A and 22B show the synergistic effect of $^{super}$FVa and increasing concentration of Kcentra™ in NHP treated with Rivaroxaban. Thrombin generation was determined as ETP and peak height in normal human plasma supplemented with 200 nM rivaroxaban. The effects on reversal of thrombin generation with Kcentra™ alone at increasing concentrations (0.08 to 1.35 U/mL) or in combination with $^{super}$FVa (50 nM) were studied. (A) Representative example of ETP at increasing concentrations of Kcentra™ in the absence (top panel) or presence of $^{super}$FVa at 50 nM concentration (bottom panel). (B) ETP (top panel) and peak height (bottom panel) achieved with increasing concentrations of Kcentra™ in the absence (black curve) or presence of $^{super}$FVa (red curve). Kcentra™ at 1.35 U/kg corresponds to the expected plasma concentration after infusion of the highest recommended dose (50 U/kg). The blue point represents the ETP of normal human plasma in the absence of rivaroxaban. Endogenous Thrombin Potential; ETP. $^{super}$FVa; $^S$FVa. Normal human plasma; NHP. Error bars represent standard error of the mean (n≥3).

FIGS. 23A and 23B show the synergistic effect of $^{super}$FVa and increasing concentration of Kcentra™ in NHP treated with Apixaban. Thrombin generation was determined as ETP (top panels) and peak height (bottom panels) in normal human plasma supplemented with 100 ng/ml apixaban. (A) Representative example of ETP at increasing concentrations of Kcentra™ in the absence (top panel) or presence of $^{super}$FVa at 50 nM concentration (bottom panel). (B) ETP (top panel) and peak height (bottom panel) achieved with increasing concentrations of Kcentra™ in the absence (black curve) or presence of $^{super}$FVa (red curve). Kcentra™ at 1.35 U/kg corresponds to the expected plasma concentration after infusion of the highest recommended dose (50 U/kg). The blue point represents the ETP of normal human plasma in the absence of apixaban. Endogenous Thrombin Potential; ETP. $^{Super}$FVa; $^S$FVa. Normal human plasma; NHP. Error bars represent standard error of the mean (n≥3).

FIGS. 24A and 24B show the synergistic effect of Kcentra™ and increasing concentration of $^{super}$FVa in NHP treated with Rivaroxaban or Apixaban. Thrombin generation was determined as ETP (top panels) and peak height (bottom panels) in NHP supplemented with Kcentra (1.35 U/mL) in combination with increasing concentrations of $^{super}$FVa (1.25 to 400 nM) in the presence of (A) 200 nM Rivaroxaban and (B) 200 nM Apixaban. Kcentra™ at 1.35 U/kg corresponds to the expected plasma concentration after infusion of the highest recommended dose (50 U/kg). The blue point represents the ETP of NHP in the absence of rivaroxaban or apixaban. The black point represents the ETP of NHP with Kcentra (1.35 U/mL) alone in the presence of rivaroxaban or apixaban. Endogenous Thrombin Potential; ETP. $^{Super}$FVa; $^S$FVa. Normal human plasma; NHP. Error bars represent standard error of the mean (n≥3).

FIGS. 25A, B and C show bleed correction following injection of rhFVIIa combined with $^{super}$FVa is similar to bleed correction with FVIII. FVIII-deficient mice were injected intravenously with saline, rhFVIII, increasing doses of $^{super}$FVa, rhFVIIa, or rhFVIIa in combination with $^{super}$FVa (1 Unit=activity of 20 nM wild-type FVa in the prothrombinase assay). Bleeding was determined during 20 minutes after tail clip and expressed as blood loss in μl blood per gram mouse. Error bars represent SEM. Blood loss in mice injected A) with saline, rhFVIII and with increasing doses of $^{super}$FVa or rhFVIIa, B) with low dose or C) medium dose of $^{super}$FVa or rhFVIIa alone and in combination.

Figure 26:
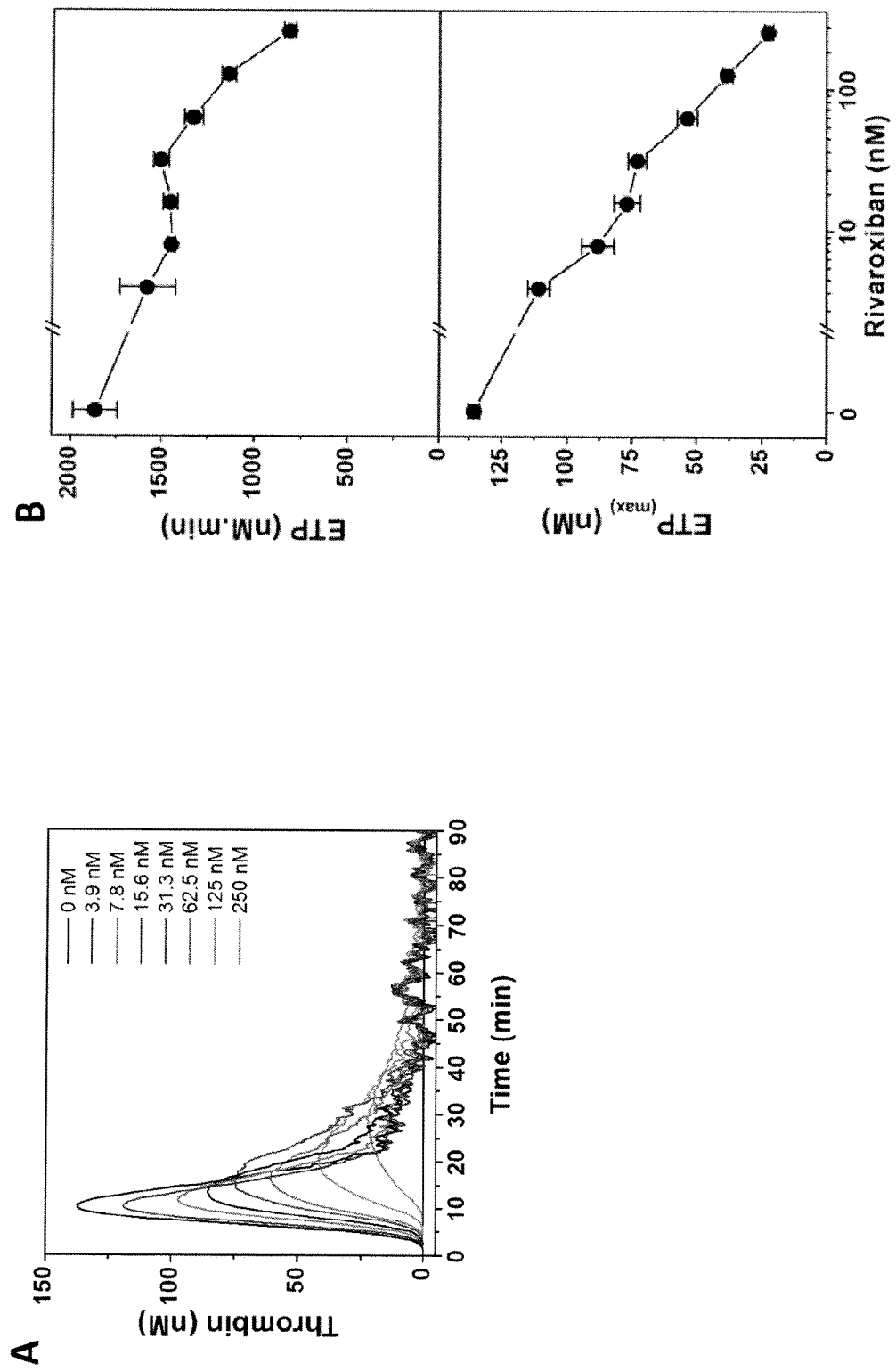

FIGS. 26A and 26B show dose titration of Rivaroxaban in NHP. Thrombin generation was determined as ETP and peak height in NHP supplemented with increasing concentrations of rivaroxaban. (A) Representative example. (B) Increasing suppression of ETP (top panel) and peak height (bottom panel) achieved with increasing concentrations of rivaroxaban. Endogenous Thrombin Potential; ETP. Normal Human Plasma; NHP. Error bars represent standard error of the mean (n≥3).

Figure 27:
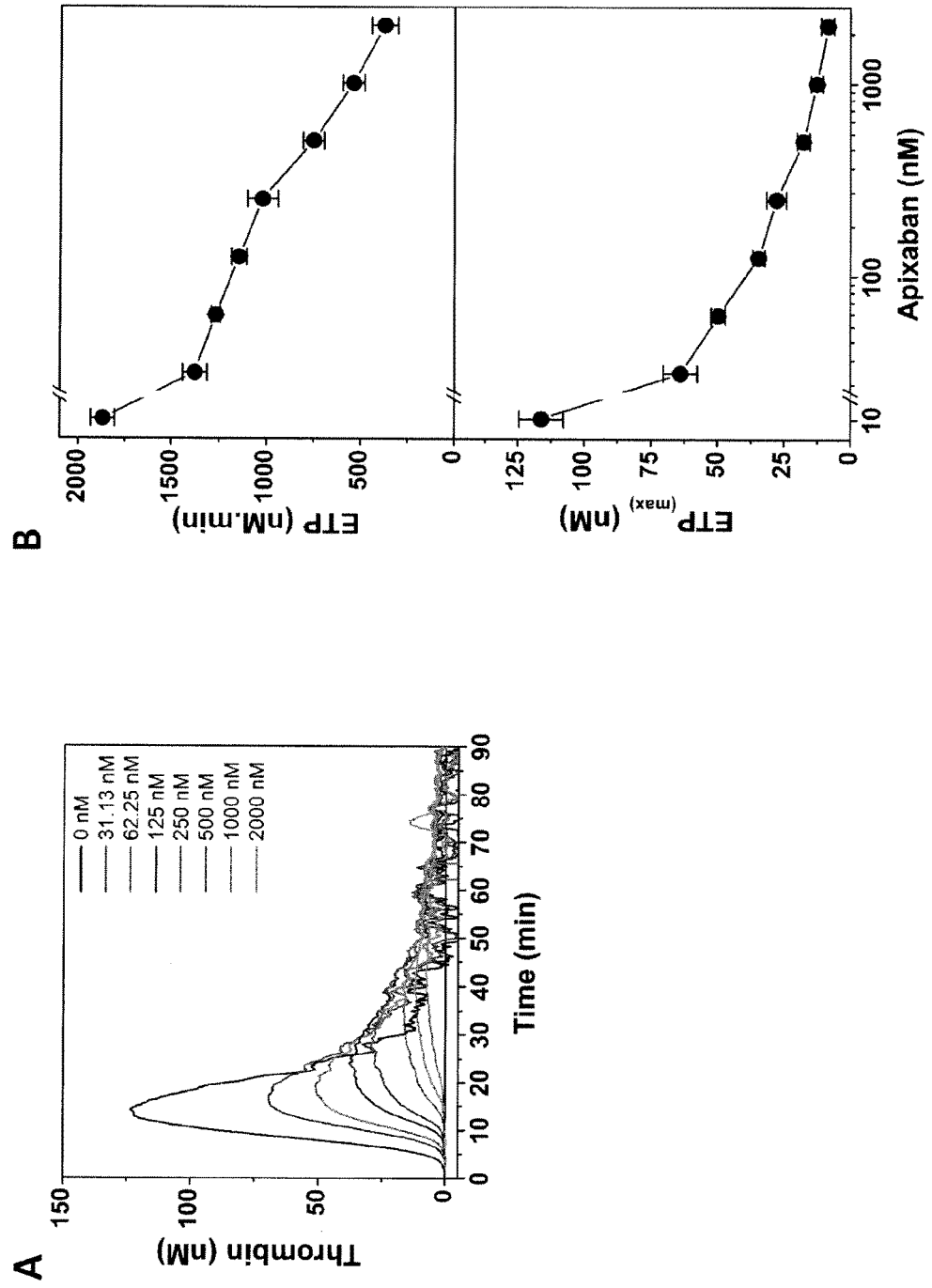

FIGS. 27A and 27B show dose titration of Apixaban in NHP. Thrombin generation was determined as ETP and peak height in NHP supplemented with increasing concentrations of apixaban. (A) Representative example. (B) Increasing suppression of ETP (top panel) and peak height (bottom panel) achieved with increasing concentrations of apixaban. Endogenous Thrombin Potential; ETP. Normal Human Plasma; NHP. Error bars represent standard error of the mean (n≥3).

FIGS. 28A and 28B show the synergistic effect of $^{super}$FVa in combination with rhFVIIa on clot stabilization in NHP spiked with anti-FVIII antibody. Clot lysis time was determined by t-PA mediated fibrinolysis following thrombin induced fibrin clot formation in NHP spiked with anti-FVIII-antibody. (A) Increasing concentrations of rhFVIIa were added in the absence (open circle) or presence (open square) of $^{super}$FVa (0.37 nM). (B) Increasing concentrations of $^{super}$FVa were added in the absence (open circle) or presence (open square) of rhFVIIa (0.37 nM). Clot lysis time of NHP without inhibitors in the absence (open upward triangle) or presence of CPI (open downward triangle) represent control experiments. Normal human plasma; NHP. Carboxypeptidase inhibitor from potato tubers; CPI. Error bars represent standard error of the mean (n≥3).

FIGS. 29A and 29B show bleed correction following injection of $^{super}$FVa, rhFVIIa, mFVIIa and a combination thereof. Balb/c mice were injected intravenously with antibody against FVIII (0.25 mg/kg) and bleeding was determined during 20 minutes after tail clip and expressed as blood loss in μl blood per gram mouse. (A) Blood loss was measured by intravenous injection of saline, increasing doses of $^{super}$FVa or rhFVIIa and a combination of rhFVIIa and $^{super}$FVa at low concentration. (B) Blood loss was measured by intravenous injection of an increasing dose of mFVIIa and a combination of mFVIIa and $^{super}$FVa at low concentration. Error bars represent SEM. 1 Unit=activity of 20 nM wild-type FVa in the prothrombinase assay. NS; No Significance.

Figure 30:
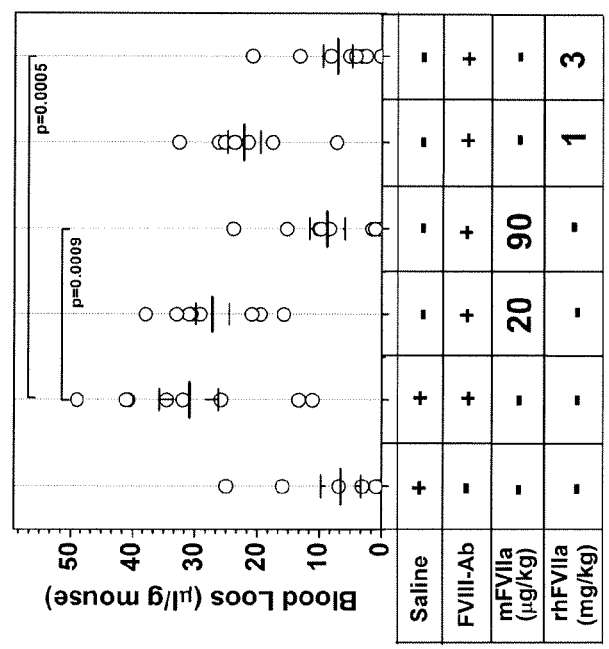

FIG. 30 shows a comparison of bleed correction following injection of rhFVIIa or mFVIIa at different concentrations. Balb/C mice were injected intravenously with antibody against FVIII (0.25 mg/kg) and bleeding was determined during 20 minutes after tail clip and expressed as blood loss in μl blood per gram mouse. Blood loss was measured after intravenous injection of saline, increasing doses of mFVIIa or rhFVIIa. Error bars represent SEM.

FIG. 31 shows the minimum concentration of rhFVIIa or $^{super}$FVa, alone and in combination, to prolong mean clot lysis time to normal. (A) Prolongation of clot lysis time in NHP spiked with anti-FVIII antibody (10 μg/ml) to that of NHP without antibody (+/−10%). Mean clot lysis time of Normal Human Plasma was ~105 min (n=3, SEM±6.4), and of FVIII deficient Plasma with rhFVIII was ~95 min (n=3, SEM±7.5), respectively. Normal human plasma; NHP.

Figure 32:
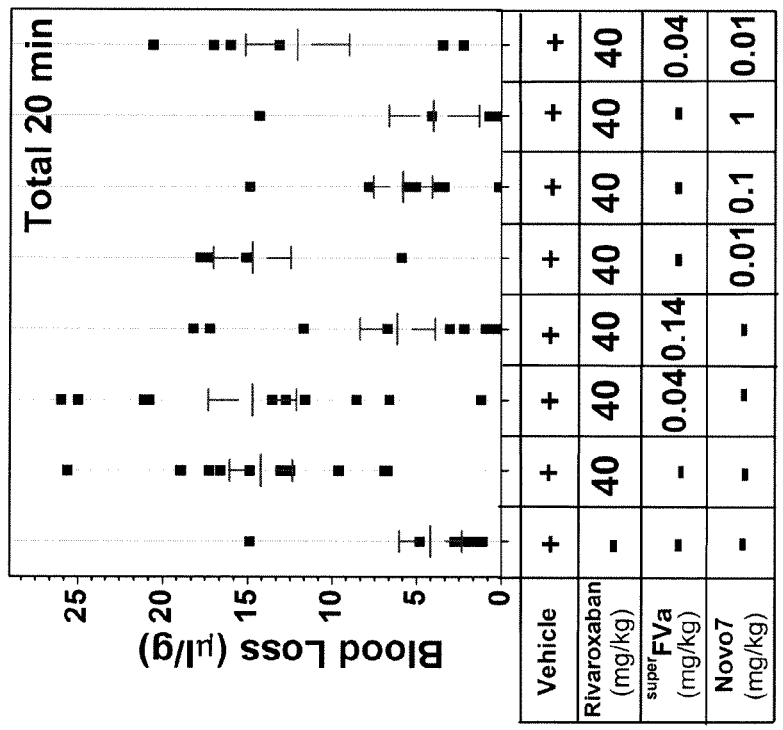

FIG. 32 shows the correction of Rivaroxaban-induced bleeding by $^{super}$FVa and NovoSeven® either alone or in combination in the murine tail clip model. Wild-type Balb/c mice were injected intravenously with Rivaroxaban or saline. $^{super}$FVa or/and NovoSeven® was injected intravenously 30 minutes after the Rivaroxaban injection. Bleeding after tail clip is expressed as blood loss in μl blood per gram mouse in 20 minutes.

FIGS. 33A and B show the correction of Apixaban-induced bleeding by $^{super}$FVa or NovoSeven® in the murine tail clip model. Wild-type Balb/c mice were injected intravenously with Apixaban (20 mg/kg in panel A; or 8 mg/kg in panel B) or saline. $^{super}$FVa or NovoSeven® was injected intravenously 30 minutes after the Rivaroxaban injection. Bleeding after tail clip is expressed as blood loss in μl blood per gram mouse in 20 minutes.

Figure 34:
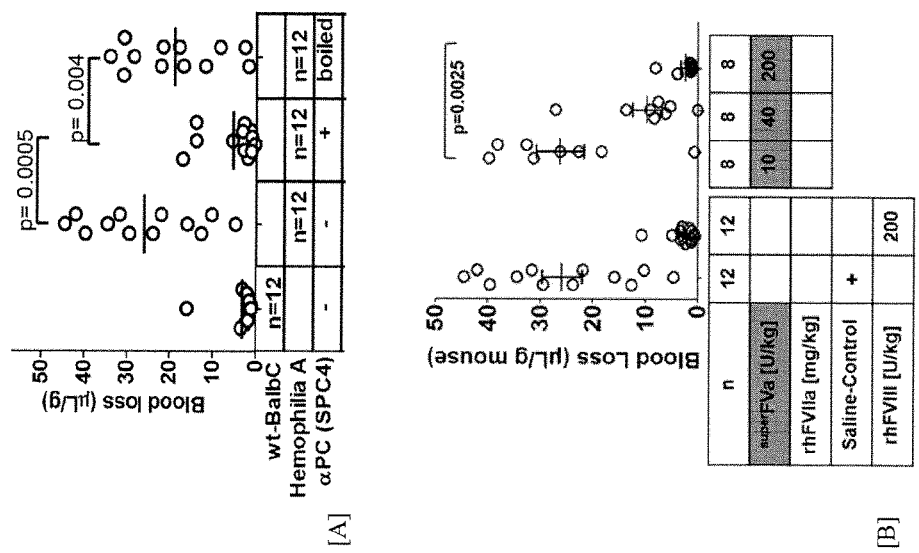

FIGS. 34A and B show that traumatic bleeding can be treated in vivo using $^{super}$FVa. A) Hemophilia A mice were treated with antibody SPC54 (10 mg/kg) against APC that blocks APC activity (Burnier L, Fernández J A, Griffin J H. Antibody SPC-54 provides acute in vivo blockage of the murine protein C system. Blood Cells Mol Dis. 2013 April; 50(4):252-8). Blocking APC activity in the hemophilia A mice reduced bleeding to the level observed in wild type BalbC mice, whereas the heat inactivated SPC54 antibody had no effect. B) The bleed reduction by the SPC54 antibody was the same as that achieved by $^{super}$FVa or treatment of hemophilia A mice with FVIII. This suggests that bleeding in hemophilia is another example of acute traumatic coagulopathy where trauma and shock cause activation of endogenous APC that mediates bleeding. Inhibition of APC, either by the blocking antibody SPC54 or by APC-resistant $^{super}$FVa reduces bleeding.

DETAILED DESCRIPTION

The present invention provides a novel therapeutic regimen for treating or preventing hypocoagulation and/or for preventing and treating bleeding in an individual in need thereof, comprising the administration of FVa, preferably a FVa that is resistant to APC degradation, alone or in combination with FVIIa, preferably the FVIIa is rhFVIIa (NovoSeven®). Also, the invention provides pharmaceutical compositions which are administrable to a subject in need of enhanced blood coagulation wherein such need for enhanced blood coagulation may arise due to any bleeding disorder or condition, e.g., a genetic condition, e.g., a hemophilia, an acquired bleeding disorder, dysmenorrhea or an event such as an injury, trauma, or as a result of surgery, or an invasive procedure that may result in excessive bleeding. In a preferred embodiment, bleeding disorders treatable by the invention include APC-associated or APC-induced or APC-mediated bleeding disorders, e.g., disorders caused by excess APC production (such as resulting from serious injury and hemorrhagic shock) or the administration of synthetic or biologic coagulants.

Further the invention provides methods of using $^{super}$FVa alone or in combination with FVIIIa to prevent, treat or reverse APC-associated, APC-induced or APC-mediated bleeding, e.g., due to the excess production of APC (such as resulting from serious injury and hemorrhagic shock) or during APC therapy, e.g., during the treatment of an inflammatory disorder such as thrombocytopenia, disseminated intravascular coagulation or sepsis disease.

In order to better describe the invention the following definitions are provided.

By "subject" or "individual" is included any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The invention described herein is intended for use in any of the above vertebrate species. However, in certain preferred embodiments, the subject or individual is human, e.g., a subject with an inherited or acquired bleeding disorder, or a person with a condition such as an injury, trauma, dysmenorrhea, surgery or other invasive procedure that causes bleeding or increases the risk of undesired bleeding, or unexplained bleeding.

The term "traumatic bleeding" (which is used interchangeably with "bleeding as a result of trauma" or "bleeding caused by trauma") refers to bleeding that is caused by an injury. The injury (or trauma) causing traumatic bleeding may vary in severity. Non-limiting examples of traumatic injury include abrasions, hematoma, bruises, lacerations, incisions, puncture wounds, crushing injuries and gunshot wounds. Traumatic bleeding includes external and internal blood loss. Internal bleeding often occurs after a significant physical injury, but it can also occur after a less severe injury or be delayed by hours or days. There are two main types of trauma or injury that can cause internal bleeding: blunt trauma and penetrating trauma. Blunt trauma occurs when a body part collides with something else, usually at high speed. As a result of blunt trauma, blood vessels inside the body may be torn or crushed by shear forces and/or a blunt object. Non-limiting examples of blunt trauma include, but are not limited to, vehicle accidents, physical assaults, and falls. Penetrating trauma occurs when a foreign object penetrates the body, tearing a hole in one or more blood vessels. Non-limiting examples of penetrating trauma include, but are not limited to, gunshot or blast wounds, stabbings, or falling onto a sharp object. Almost any organ or blood vessel can be damaged by trauma and cause internal bleeding. The most serious sources of internal bleeding due to trauma include, but are not limited to, head trauma with internal bleeding (intracranial hemorrhage); bleeding around the lungs (hemothorax); bleeding around the heart (hemopericardium and cardiac tamponade); tears in the large blood vessels near the center of the body (aorta, superior and inferior vena cava, and their major branches); and damage caused by trauma to the abdomen such as liver or spleen lacerations or perforation of other soft organs. For the purposes of this application, traumatic bleeding is studied in vivo using animal models, i.e., wild-type mice subject to traumatic tail transection or liver laceration (see FIGS. 11 and 13) or hemophilia mice subject to traumatic tail transection (see FIG. 34), which rapid bleeding due to trauma is mediated, in part or in whole, by APC-induced traumatic coagulopathy. Patients with traumatic bleeding may receive treatments, as disclosed herein, to help their blood clot properly.

The term "patient" refers to a living organism suffering from or prone to a condition that can be prevented or treated by the treatment regimen the invention, and includes both humans and animals.

The term "aPCC concentrate" refers to activated Prothrombin Complex Concentrates such as FEIBA, which contains factors such as FVII, prothrombin (FII), FIX and/or FX (and their active forms).

The term "Factor Va" and "FVa" means the activated form of "Factor V" (or "FV"), preferably human FVa. As used herein, FVa and FV include the wt FV sequence (NM_000130.4; NP_00121.2) as well as all known polymorphisms of FV (see http://www.ncbi.nlm.nih.gov/SNP/snp_ref.cgi?locusId=2153, which summarizes the known polymorphisms of factor V). For example, FV can include one or more of the single nucleotide polymorphisms (SNPs) altering the amino acid at position(s) Asp2222, Glu2217, Ala2213, Ile2204, Arg2202, Phe2200, Ile2197, Lys2185, Glu2179, Asp2175, Glu2163, Val2162, Thr2154, Lys2151, Met2148, Thr2134, Thr2134, Leu2128, Arg2108, Leu2103, Leu2103, Phe2087, Ser2086, Ser2085, Gln2081, Met2072, Pro2069, Cys2066, Arg2055, Glu2029, Thr2026, Asn2010, Gln2001, His1983, Gln1975, Ile1972, Ala1955, Ser1949, Ser1944, Gly1930, Lys1924, Pro1910, Arg1908, Thr1898, Thr1898, Ala1894, Met1874, Pro1863, Gly1853, His1845, Val1841, Gly1835, Gly1834, Ile1833, Leu1830, Met1820, Leu1818, Pro1816, Tyr1813, Met1811, His1806, Thr1795, Trp1792, Ser1790, Arg1789, Tyr1783, Phe1776, Val1770, Met1764, Met1762, Ile1755, Lys1753, Leu1749, Ile1745, Leu1744, Arg1726, Gly1722, Gly1717, Ser1716, Tyr1708, Glu1687, Thr1685, Ser1680, Gly1674, His1673, Pro1667, Ser1665, Ala1664, Arg1659, Leu1641, Leu1624, Val1618, Tyr1615, Tyr1615, Asp1612, Asp1605, Gln1598, Asn1575, Asn1559, Arh1555, Val1554, Asp1547, Tyr1546, Val1544, Glu1530, Ile1523, Asp1521, Asp1518, Ser1516, Leu1503, Asn1499, Gln1476, Ser1469, Pro146, Ser1455, Ile1454, Leu1451, Pro1449, Thr1445, Thr1437, Val1436, Gln1435, Ser1430, Asn1423, Met1409, Asp1407, Pro1404, Ley1397, Ser1376, Asn1374, Asp1369, Thr1365, Pro1361, Asp1360, Met1355, Gly1353, Leu1352, Asn1338, Phe1334, Leu1330, His1327, Pro1323, Ile1321, Gln1318, Gly1317, Leu1316, Leu1303, Phe1289, Leu1285, Thr1284, His1282, Pro1278, Leu1276, Leu1271, Ser1268, Leu1267, Ser1259, Leu1253, Leu1249, Thr1247, His1246, Pro1242, Ser1236, Asp1234, Pro1230, Gly1227, Ser1223, Gln1219, Thr1211, His1210, Leu1208, Pro1206, Ser1200, Thr1194, Pro1188, Val1185, trp1182, His1179, Ser1174, Thr1168, Ser1162, Arg1161, Asp1160, Tyr1159, Met156, Glu1152, Ser1149, Ser1148, His1114, Pro1135, Asp1134, Pro1131, Pro1122, Gln1110, Gly1109, Ser1104, Leu1086, Thr1085, Asp081, Thr1080, Asn1074, His1071, Ser1067, Lys1065, Glu1054, Leu1051, Gln1024, Gly1016, Asp1014, Gln1013, Lys1000, Ala981, Arg980, Pro975, Asn969, Ala967, Thr966, Asp961, Ile959, Tyr956, Ser955, Ser951, Leu949, Gly945, Gln936, Lys925, Pro918, Thr915, Ser912, trp907, Arg905, Met904, Ser902, Pro901, Ser900, Val890, Lys877, Lys869, Gly867, His865, Lys858, Phe857, Gly853, Arg848, Asn821, Asn817, Gly815, Pro809, Gln802, Pro798, Ala797, Gln795, Asn789, Ser781, Pro780, Ser779, Gly774, Ile772, Ser767, Phe764, Glu763, Gly761, Leu753, Asn745, Ser742, Asn741, Arg740, Ile736, Ala732, Ser720, Glu719, Glu714, Arg712, His710, Arg707, Thr702, Phe696, Glu690, Pro686, Phe679, Lys678, Lys674, Ser672, Pro670, Ser669, Met666, Thr664, Asp656, Thr652, Arg647, Thr642m Ley641, Thr640, Lys635, Gly628, Ile624, Thr623, Gln618, Val608, Glu595, Tyr592, Gly591, Glu572, Asn554, Glu553, Gln545, Leu522, Arg513, Lys484, Tyr481, Thr464, Ser461, Asn460, Glu458, Tyr455, Pro447, Val434, Ile433, Arg428, Lys414, Met413, Asn410, Val394, Lys392, Gln386, Asn385, Arg376, Asp372, Met371, Ala369, Asp362, Ile354, Phe353, Arg345, Arg341m Asn335, Lys332, Cys329, Ile324, Gln321, Pro313, Lys305, Asn297, Thr295, Ser293, Lue288, Thr287, Glu277, Leu276, Val275, Gln274, Asn272m Phe267, Ser262, Leu257, His250, Thr246, Pro243, Gln210, Thr206, Pro189, Gly188, Ser184, Glu180, Ile179, His175, His170, Pro166, Glu151, Arg146, Val142, Ala141, Met138, Ala135, Phe133, Ser123, Gln115, Leu110, Pro109, Asp107, Ile97, Asp96, Gly95, Val94, Tyr91, Leu85, Ile82, Gln79, Tyr69, Arg46, Ala38, Ala37, Val36, Ala28, Gly15, Gly4 (relative to the wt sequence of NP_000121.2). In preferred embodiments of the invention, FVa will comprise mutations that render it APC resistant such as the $^{super}$FVa or other variants disclosed herein. Also, in preferred embodiments of the invention, FVa may comprise a chemical modification (e.g., PEGylation) that improves the physical stability of other properties of the protein. It should be understood that, for purposes of this application, "Factor V" and "Factor Va" include wild-type, plasma-derived, Leiden and Cambridge F V and FVa forms of the factor.

The term "$^{super}$FVa" herein refers to a FVa molecule or fragment or variant thereof that has been modified to have enhanced properties, e.g., enhanced cofactor stability, enhanced specific activity and/or enhanced half-life in the blood. Non-limiting examples of modifications that enhance FVa cofactor stability include, but are not limited to, the introduction of cysteine residues that form disulfide pairs to stabilize the molecule, mutations at the interface of the A1, A2, B, A3, C1, and/or C2 domain that introduce attracting electrostatic interactions, eliminate opposing electrostatic interactions and/or that introduce hydrophobic interactions, as was recently demonstrated for FVIIIa (See *Noncovalent stabilization of the factor VIII A2 domain enhances efficacy in hemophilia A mouse vascular injury models*. Lilley Leong, Derek Sim, Chandra Patel, Katherine Tran, Perry Liu, Elena Ho, Thomas Thompson, Peter J. Kretschmer, Hironao Wakabayashi, Philip J. Fay, and John E. Murphy. Blood 2014 (in press) (DOI: http://dx.doi.org/10.1182/blood-2014-02-555656). Examples of modifications that enhance the specific activity of FVa include, but are not limited to, the introduction of cysteine residues that form disulfide pairs or mutations and alterations that increase the affinity of FVa for FXa, such as mutations of the A2-A3 interface, introduction of sequences of FVIII known to provide high affinity binding to FX including the a1 domain. Examples of modifications that enhance FVa half-life in the circulation include, but are not limited to, the introduction of site-directed incorporation of synthetic or chemical modifications such as polyethylene glycol (PEG) polymers or multimers, Fc receptor fusion domains, albumin fusion, or other known structures that may prolong the half-life in the circulation or reduce clearance mechanisms.

In a particular embodiment, $^{super}$FVa comprises a combination of mutations that render the protein resistant to APC inactivation, preferably highly APC resistant, such as the specific mutations disclosed herein. Preferably, the $^{super}$FVa comprises the amino acid sequence below (SEQ ID NO: 1). This sequence comprises the mature FVa protein (without the prepro sequence). To clarify, this protein has the following changes relative to wild type human FV: The sequence of 812-1491 is deleted (from the B domain). For all changes other than this deletion based on the original full length FV sequence numbering, $^{super}$FVa preferably comprises the following mutations: R306Q, R506Q, R679Q, H609C, E1691C (1011), S2183lA (1503).

1 aqlrqfyvaa qgiswsyrpe ptnsslnlsv tsfkkivyre yepyfk-kekp qstisgllgp 61 tlyaevgdii kvhfknkadk plsihpqgir ysklsegasy ldhtf-paekm ddavapgrey 121 tyewsiseds gpthddppcl thiyyshenl iedfnsglig pllick-
kgtl teggtqktfd 181 kqivllfavf deskswsqss slmytvngyv ngtmpditvc
ahdhiswhll gmssgpelfs 241 ihfngqvleq nhhkvsaitl vsatsttanm tvgpegkwii ssltp-
khlqa gmqayidikn 301 cpkktqnlkk itreqrrhmk rweyfiaaee viwdyapvip anm-
dkkyrsq hldnfsnqig 361 khykkvmytq yedesftkht vnpnmkedgi lgpiiraqvr
dtlkivfknm asrpysiyph 421 gvtfspyede vnssftsgrn ntmiravqpg etytykwnil efdep-
tenda qcltrpyysd 481 vdimrdiasg liglllicks rsldrqgiqr aadieqqavf avfdenk-
swy ledninkfce 541 npdevkrddp kfyesnimst ingyvpesit tlgfcfddtv qwh-
fcsvgtq neiltihftg 601 hsfiygkrce dtltlfpmrg esvtvtmdnv gtwmltsmns sprsk-
klrlk frdvkcipdd 661 dedsyeifep pestvmatqk mhdrlepede esdadydyqn
rlaaalgirs frnsslnqee 721 eefnltalal engtefvssn tdiivgsnys spsniskftv nnlae-
pqkap shqqattags 781 plrhligkns vlnsstaehs spysedpied ptdyieiipk
eevqsseddy aeidyvpydd 841 pyktdvrtni nssrdpdnia awylrsnngn rrnyyiaaee
iswdysefvq retdiedsdd 901 ipedttykkv vfrkyldstf tkrdprgeye ehlgilgpii raevd-
dviqv rfknlasrpy 961 slhahglsye kssegktyed dspewfkedn avqpnssyty
vwhatersgp cspgsacraw 1021 ayysavnpek dihsgligpl licqkgilhk dsnmpvdmre fvll-
fmtfde kkswyyekks 1081 rsswrltsse mkkshefhai ngmiyslpgl kmyeqewvrl hll-
niggsqd ihvvhfhgqt 1141 llengnkqhq lgvwpllpgs fktlemkask pgwwllntev gen-
qragmqt pflimdrdcr 1201 mpmglstgii sdsqikasef lgyweprlar lnnggsynaw sve-
klaaefa skpwiqvdmq 1261 keviitgiqt qgakhylksc yttefyvays snqinwqifk gnstrn-
vmyf ngnsdastik 1321 enqfdppiva ryirisptra ynrptlrlel qgcevngcst plg-
mengkie nkqitassfk 1381 kswwgdywep frarlnaqgr vnawqakann nkqwleidll
kikkitaiit qgckslssem 1441 yvksytihys eqgvewkpyr lkssmvdkif egntntkghv
knffnppiis rfirvipktw 1501 nqaitlrlel fgcdiy (SEQ ID NO:1)

More preferably, the $^

```
-continued
YLKSCYTTEFYVAYSSNQINWQIFKGNSTRNVMYENGNSDASTIKE

NQFDPPIVARYIRISPTRAYNRPTLRLELQGCEVNGCSTPLGMENG

KIENKQITASSFKKSWWGDYWEPFRARLNAQGRVNAWQAKANNNKQ

WLEIDLLKIKKITAIITQGCKSLSSEMYVKSYTIHYSEQGVEWKPY

RLKSSMVDKIFEGNTNTKGHVKNFFNPPIISRFIRVIPKTWNQAIA

LRLELFGCDIY*
```

The term "Factor VIIa" or "FVIIa" means an activated form of Factor VII. This in particular includes a FVIIa product sold by Novo Nordisk referred to as NovoSeven®. In addition, FVIIa includes other variants of recombinant FVIIa with longer half-life or increased activity relative to wild-type, e.g., because of mutation(s) and/or as a result of the addition or attachment of half-life improving entities thereto such as PEG or acyl groups. Therefore, as used herein, FVIIa includes the sequence for wild-type FVIIa and variants of this sequence having enhanced activity or stability, e.g., truncated forms comprising N-, C- and/or internal deletions, site mutations, and/or comprising one or more stabilizing or other functional groups. The sequence of a human FVIIa polypeptide is set forth below:

```
                                          (SEQ ID NO: 2)
ANAFLEELRPGSLERECKEEQCSFEEAREIFKDAERTKLFWISYSD

GDQCASSPCQNGGSCKDQLQSYICFCLPAFEGRNCETHKDDQLICV

NENGGCEQYCSDHTGTKRSCRCHEGYSLLADGVSCTPTVEYPCGKI

PILEKRNASKPQGRIVGGKVCPKGECPWQVLLLVNGAQLCGGTLIN

TIWVVSAAHCFDKIKNWRNLIAVLGEHDLSEHDGDEQSRRVAQVII

PSTYVPGTTNHDIALLRLHQPVVLTDHVVPLCLPERTFSERTLAFV

RFSLVSGWGQLLDRGATALELMVLNVPRLMTQDCLQQSRKVGDSPN

ITEYMFCAGYSDGSKDSCKGDSGGPHATHYRGTWYLTGIVSWGQGC

ATVGHFGVYTRVSQYIEWLQKLMRSEPRPGVLLRAPFP
```

The sequence of a human pro-FVII polypeptide (corresponding to NP_000122.1; coagulation factor VII isoform a preproprotein, *Homo sapiens*) is set forth below:

```
                                          (SEQ ID NO: 3)
MVSQALRLLCLLLGLQGCLAAGGVAKASGGETRDMPWKPGPHRVFV

TQEEAHGVLHRRRRANAFLEELRPGSLERECKEEQCSFEEAREIFK

DAERTKLFWISYSDGDQCASSPCQNGGSCKDQLQSYICFCLPAFEG

RNCETHKDDQLICVNENGGCEQYCSDHTGTKRSCRCHEGYSLLADG

VSCTPTVEYPCGKIPILEKRNASKPQGRIVGGKVCPKGECPWQVLL

LVNGAQLCGGTLINTIWVVSAAHCFDKIKNWRNLIAVLGEHDLSEH

DGDEQSRRVAQVIIPSTYVPGTTNHDIALLRLHQPVVLTDHVVPLC

LPERTFSERTLAFVRFSLVSGWGQLLDRGATALELMVLNVPRLMTQ

DCLQQSRKVGDSPNITEYMFCAGYSDGSKDSCKGDSGGPHATHYRG

TWYLTGIVSWGQGCATVGHFGVYTRVSQYIEWLQKLMRSEPRPGVL

LRAPFP
```

The term "Factor IXa" or "FIXa" means an activated form of "Factor IX". This includes mutants and variants of FIXa and FIX with decreased functional dependence on FVIII or FVIIIa for activation. For example, FIX with mutations at Y259F, K265T, Y345T, V181I, R338A and/or I383V. See Chang et al., J Biol Chem, 273: 12089-94 (1998); Milanov et al., Blood 119(2):602-611 (2012); Quade-Lyssy et al., J Genet Syndr Gene Ther S1:013 (2012), the disclosures of which are herein expressly incorporated by reference. Therefore, as used herein, FIXa includes the sequence for wild-type FIXa and mutants and variants of this sequence having enhanced activity or stability, e.g., truncated forms comprising N-, C- and/or internal deletions, site mutations, and/or comprising one or more stabilizing or other functional groups, e.g., glycovariants (see Brooks et al., J. Thrombosis and Haemostasis, 11(9): 1699-1706 (2013).

The term "Factor Xa" or "FXa" means an activated form of "Factor X". This includes mutants and variants of FXa and FX. For example, FX and FXa with mutations at positions 16, 17 and/or 18 (according to chymotrypsin numbering). Also encompassed by FXa is $FXa^{I116L}$ which has a longer half-life than wild-type FXa and does not cause excessive activation of coagulation. See, e.g., Ivanciu et al., Nature Biotech 29: 1028-1033 (2011), the disclosure of which is herein expressly incorporated by reference. Therefore, as used herein, FXa includes the sequence for wild-type FXa and mutants and variants of this sequence having enhanced activity or stability or specificity, e.g., truncated forms comprising N-, C- and/or internal deletions, site mutations, and/or comprising one or more stabilizing or other functional groups.

The term "therapeutically effective cycle of treatment" with FVa and FVIIa, preferably a $^{super}$FVa and rhFVIIa (NovoSeven®) is intended as a cycle of treatment that when administered, brings about a positive therapeutic response with respect to treatment of an individual having a bleeding disorder or at risk of developing a bleeding disorder or bleeding condition, e.g., as the result of surgery, injury, or caused by the overexpression of APC or the administration of APC during therapy. Preferably the treatment will elicit a synergistic effect on clotting or coagulation or APC-associated bleeding by affecting thrombin generation or reversing the anticoagulant effects of APC or other anticoagulants.

A "positive therapeutic response" is one in which the individual undergoing treatment according to the invention exhibits an improvement in one or more symptoms of a bleeding disorder, including such improvements as shortened blood clotting times and reduced bleeding and/or reduced need for factor replacement therapy. Preferably, the administration will elicit an effect, more preferably a synergistic effect, on clotting or coagulation by promoting thrombin generation or preventing the ablation of thrombin generation, e.g., as a result of APC administration as discussed infra and shown in the working examples.

A "procoagulant" refers to any factor or reagent capable of initiating or accelerating clot formation. A procoagulant includes any activator of the intrinsic or extrinsic coagulation pathways, such as a clotting factor selected from the group consisting of FXa, FIXa, FXIa, FXIIa, kallikrein, tissue factor, FVIIa, and thrombin, as well as FVIIIa, FXIIIa, and Thrombin Activatable Fibrinolysis Inhibitor (TAFI), activated TAFI (TAFIa); and activated Prothrombin Complex Concentrates (aPCC), such as FEIBA, which may comprise factors VII, FII, FIX and FX (and their active forms). Other reagents that promote clotting include prekallikrein, polyphosphate, APTT initiator (i.e., a reagent containing a phospholipid and a contact activator), Russell's viper venom (RVV time), anti-fibrinolytic agents such as tranexamic acid or epsilon-aminocaproic acid, and thromboplastin (for PT and dPT). Contact activators that can be used in the methods of the invention as procoagulant reagents include micronized silica particles, ellagic acid, sulfatides, kaolin or the like known to those of skill in the art. Procoagulants may be from a crude natural extract, a blood or plasma sample, isolated and substantially purified, synthetic, or recombinant. Procoagulants may include naturally occurring clotting factors or fragments, variants, analogs or muteins thereof that retain biological activity (i.e., promote clotting).

The terms "variant", "analog" and "mutein" refer to biologically active derivatives of the reference molecule that retain desired activity, such as clotting activity, in the treatment of a bleeding disorder described herein. In the present invention, variants of FVa contain one or more naturally occurring or genetically engineered mutations that inhibit APC degradation of the resultant variant or mutein. In general, the terms "variant" and "analog" in reference to a polypeptide (e.g., FVa or FVIIa polypeptide) that differs from the native polypeptide sequence and structure by one or more amino acid additions, substitutions (generally conservative in nature) and/or deletions, relative to the native molecule, so long as the modifications do not destroy biological activity and which are "substantially homologous" to the reference molecule as defined below. In general, the amino acid sequences of such variants or analogs will have a high degree of sequence homology to the reference sequence, e.g., amino acid sequence homology of more than 50%, generally more than 60%-70%, even more particularly 80%-85% or more, such as at least 90%-95% or more, when the two sequences are aligned. Often, the analogs will include the same number of amino acids but will include substitutions, as explained herein. Additionally, the variants of, e.g., FVa, FVIIa, FIX, and FX, include biologically active derivatives that contain the same amino acid sequence but include a chemical modification, e.g., covalent modification, e.g., PEGylation (attachment of poly-ethylene glycol (PEG)), HESylation (attachment of hydroxyethyl starch (HES)), XTENylation (attachment of XTEN (a polypeptide)), HSAylation (attachment of human serum albumin (HSA)), PASylation (attachment of polypeptide chains with expanded hydrodynamic volume comprising the small residues Pro, Ala and Ser (PAS)), glutamylation (attachment of polyglutamic acid), etc., that improves the physical property of the variant (e.g., extended half-life in the blood) without affecting its biological activity.

The term "mutein" further includes polypeptides having one or more amino acid-like molecules including but not limited to compounds comprising only amino and/or imino molecules, polypeptides containing one or more analogs of an amino acid (including, for example, unnatural amino acids, etc.), polypeptides with substituted linkages, as well as other modifications known in the art, both naturally occurring and non-naturally occurring (e.g., synthetic), cyclized, branched molecules and the like. The term also includes molecules comprising one or more N-substituted glycine residues (a "peptoid") and other synthetic amino acids or peptides. (See, e.g., U.S. Pat. Nos. 5,831,005; 5,877,278; and 5,977,301; Nguyen et al., Chem. Biol. (2000) 7:463-473; and Simon et al., Proc. Natl. Acad. Sci. USA (1992) 89:9367-9371 for descriptions of peptoids). Preferably, the analog or mutein has at least the same or increased or decreased activity or selectivity for one activity versus another, e.g., clotting activity relative to the native molecule. Methods for making polypeptide analogs and muteins are known in the art and are described further below.

As explained above, analogs also include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine, threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 conservative or non-conservative amino acid substitutions, or any integer between 5-25, so long as the desired function of the molecule remains intact. One of skill in the art may readily determine regions of the molecule of interest that can tolerate change by reference to Hopp/Woods and Kyte-Doolittle plots, well known in the art.

By "fragment" is intended a molecule consisting of only a part of the intact full-length sequence and structure. A fragment of a polypeptide can include a C-terminal deletion, an N-terminal deletion, and/or an internal deletion of the native polypeptide. Active fragments of a particular protein will generally include at least about 5-10 contiguous amino acid residues of the full-length molecule, preferably at least about 15-25 contiguous amino acid residues of the full-length molecule, and most preferably at least about 20-50 or more contiguous amino acid residues of the full-length molecule, or any integer between 5 amino acids and the full-length sequence, provided that the fragment in question retains biological activity, such as clotting activity, as defined herein.

"Homology" refers to the percent identity between two polynucleotide or two polypeptide moieties. Two nucleic acid, or two polypeptide sequences are "substantially homologous" to each other when the sequences exhibit at least about 50%, preferably at least about 75%, more preferably at least about 80%-85%, preferably at least about 90%, and most preferably at least about 95%-98% sequence identity over a defined length of the molecules. As used herein, substantially homologous also refers to sequences showing complete identity to the specified sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules (the reference sequence and a sequence with unknown % identity to the reference sequence) by aligning the sequences, counting the exact number of matches between the two aligned sequences, dividing by the length of the reference sequence, and multiplying the result by 100. Readily available computer programs can be used to aid in the analysis, such as ALIGN, Dayhoff, M. O. in Atlas of Protein Sequence and Structure M. O. Dayhoff ed., 5 Suppl. 3:353-358, National Biomedical Research Foundation, Washington, D.C., which adapts the local homology algorithm of Smith and Waterman Advances in Appl. Math. 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+ PDB+GenBank CDS translations+Swiss protein+Spupdate+ PIR. Details of these programs are readily available.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide.

The methods and compositions used to treat or prevent bleeding in the invention may further comprise, in addition to FVa alone or in combination with FVIIa, the administration of one or more other factors or clotting factors such as FXI, FXII, prekallikrein, high molecular weight kininogen (HMWK), FVIII, FVIIIa, FIX, FX, FXIII, FII, FVIIa, and von Willebrand factor, Thrombin Activatable Fibrinolysis Inhibitor (TAFI) anti-fibrinolytics (e.g., Amicar, Tranexamic Acid, ε aminocaproic acid, aprotinin, and the like) which are sometimes used in hemophilia and other bleeding disorders to prevent bleeding (e.g., such as are used during tooth extraction).

The clot-lysis data disclosed infra demonstrates that the synergy between FVIIa and $^{super}$FVa restores resistance of the clot to fibrinolysis that is lost in hemophilia due to the defect in thrombin generation. The FVIIa/$^{super}$FVa synergy restores the activation of Thrombin Activatable Fibrinolysis Inhibitor ("TAFI"), which is one of the body's natural antifibrinolytics. Thus, (1) restoring resistance of the clot or increasing the clot lysis time is another measure of the functional effect of the FVIIa/$^{super}$FVa synergy, in addition to thrombin generation, (2) restoring resistance of the clot or increasing the clot lysis time is an integral part of the mechanism of why FVIIa/$^{super}$FVa synergy reduces bleeding, and (3) due to the latter it may be advantageous to combine FVIIa/$^{super}$FVa synergy with anti-fibrinolytic or TAFI to amplify the effect on reduction of bleeding by FVIIa/$^{super}$FVa synergy.

The dose of a clotting factor, e.g., FVa, preferably a $^{super}$FVa and FVIIa, preferably rhFVIIa (NovoSeven®), is an amount that in combination is effective to treat or prevent bleeding and enhance coagulation. Preferably the relative dosage amounts of these two polypeptides will elicit a synergistic effect on clotting or coagulation by promoting the generation of thrombin.

A "synergistically effective amount" herein refers to relative amounts of a FVa, preferably a $^{super}$FVa that is highly resistant to APC degradation, and an amount of FVIIa, preferably rhFVIIa (NovoSeven®) that in combination elicit a beneficial or synergistic effect, i.e., greater than the additive effect of either of these moieties alone by synergistically promoting the generation of thrombin. In the present invention the synergy is demonstrated in normal human plasma containing or lacking FVIII inhibitory antibodies based on an increase in ETP, e.g., on the order of at least a 0.5-fold increase, more preferably at least 1-fold increase and still more preferably an additional ~1.5 to 2-2.5 or 3.0 fold increase of ETP, and an ~2 to 3-fold increase of peak height relative to the increase yielded by these moieties alone taking into account normalized clot lysis time. Also, a "synergistically effective amount" herein refers to relative amounts of a FVa, preferably a $^{super}$FVa that is highly resistant to APC degradation, and optionally an amount of FVIIa which are sufficient to enhance or restore the activation of Thrombin Activatable Fibrinolysis Inhibitor (TAFI), which is one of the body's natural antifibrinolytics. Thus, synergy herein may include or alternatively refer to as well as synergistically inducing thrombin generation, restoring resistance of the clot or increasing the clot lysis time. (This is an integral part of the mechanism of why FVIIa/$^{super}$FVa synergy reduces bleeding in hemophilia, and why it may be further advantageous to combine FVIIa/$^{super}$FVa with anti-fibrinolytic or TAFI to amplify the effect on reduction of bleeding by FVIIa/$^{super}$FVa synergy). FVIIa/$^{super}$FVa synergy restores the activation of Thrombin Activatable Fibrinolysis Inhibitor (TAFI), which is one of the body's natural antifibrinolytics. Thus, restoring resistance of the clot or increasing the clot lysis time is a measure of the functional effect of the FVIIa/$^{super}$FVa synergy, in addition to thrombin generation.

Based on the experimental results shown infra, restoring resistance of the clot or increasing the clot lysis time is believed to be why FVIIa/$^{super}$FVa synergy reduces bleeding in hemophilia, and based thereon why combining FVIIa/$^{super}$FVa synergy with an anti-fibrinolytic or TAFI may further amplify the synergistic effect on reduction of bleeding by FVIIa/$^{super}$FVa synergy.

With this understanding, the present application generally relates to methods and compositions for use in such methods, for preventing or treating bleeding and/or hypocoagulation in an individual in need thereof by a therapeutic regimen preferably including the administration of synergistically effective amounts of FVa, preferably an APC resistant FVa, i.e., preferably an APC resistant FVa such as a $^{super}$FVa as described herein, and FVIIa, preferably rhFVIIa, e.g. (NovoSeven®), or another variant of recombinant FVIIa, preferably one exhibiting improved half-life or increased activity; or another procoagulant or pro-hemostatic agent, wherein the combination elicits a synergistic effect on thrombin generation relative to the FVa or FVIIa or other procoagulant or pro-hemostatic agent when administered alone to a subject in need thereof.

As used herein, the term "hypocoagulation" refers to a genetic or acquired deficiency in one or more coagulation factors and/or a condition in which plasma of the individual manifests an abnormal clotting profile in one or more standard coagulation tests. In particular, hypocoagulation refers to decreased or deficient coagulation of the blood which may result in excessive or lengthy bleeding as a result of the altered ability to form a blood clot.

Also, the invention relates to the use of FVa, preferably an APC resistant FVa, alone or in combination with a FVIIa such as NovoSeven® or another variant thereof, e.g., one possessing improved half-life or activity to treat or prevent bleeding due to excessive APC generation or anticoagulant or APC administration. As shown herein, the present inventors have demonstrated that the subject FVa, alone or in combination with FVIIIa inhibits or reverses APC-induced reduction of thrombin generation and based thereon may be used to treat subjects with bleeding or prevent bleeding caused by excessive APC generation (such as resulting from serious injury and hemorrhagic shock) or APC or other anticoagulant administration.

The present methods and compositions may in particular be used to reverse the effects of an anticoagulant in a subject, e.g., subjects who have been treated with an anticoagulant including, but not limited to, heparin, a coumarin derivative, such as warfarin or dicumarol, TFPI, AT III, APC, lupus anticoagulant, nematode anticoagulant peptide (NAPc2), FVIIa inhibitors, active-site blocked FVIIa (FVIIai), active-site blocked FIXa (FIXai), FIXa inhibitors, a FXa inhibitor, including fondaparinux, idraparinux, DX-9065a, rivaroxaban, apixaban, edoxaban, enoxaparin, and razaxaban (DPC906), active-site blocked FXa (FXai), an inhibitor of FVa or FVIIIa, including APC and derivatives, soluble thrombomodulin, a thrombin inhibitor, including hirudin, bivalirudin, argatroban, dabigatran, or ximelagatran. In certain embodiments, the anticoagulant in the subject may be an antibody or antibody fragment that binds a clotting factor, including but not limited to, an antibody or antibody fragment that binds to FV, FVII, FVIII, FIX, FX, FXIII, FII, FXI, FXII, von Willebrand factor, prekallikrein, or high molecular weight kininogen (HMWK). As an alternative to an antibody or antibody fragment, the anticoagulant may be a small drug-like molecule, peptide or aptamer which binds to a coagulation protein and thereby inhibits its activation or its interaction with another coagulation protein or cell surface.

Additionally, in a particular aspect, the present methods and compositions may be used to treat an individual one who has a genetic coagulation disorder in which blood coagulation factors (such as FV, FVIII, prothrombin, thrombomodulin, Protein C and Protein S, antithrombin, homocysteine, or lipoprotein(a)) are absent, present at lower than normal levels or present at normal levels with impaired function due to a genetic mutation of polymorphism. In particular, the treated subject may have an acquired or genetic coagulation disorder caused by, e.g., reduced synthesis of a blood coagulation factor, mutations of a chaperone protein(s), abnormal post-translational processing, proteolytic degradation, enhanced clearance, antibodies against the blood coagulation factor or impaired activation of the blood coagulation factor. In certain aspects, the blood coagulation factor that is affected in the acquired or genetic coagulation or bleeding disorder is FV, FVIII, FIX, or FX. In other certain aspects, the acquired or genetic bleeding disorder arises from genetic mutations associated with increased levels of soluble thrombomodulin and fragments thereof. For example, the Cys537 stop mutation in thrombomodulin results in enhanced levels of soluble thrombomodulin that mediate higher than normal activation of protein C and, thus, results in APC-mediated bleeding (see Langdown et al., Blood 2014 124(12): 1951-6 (2014), the disclosure of which is expressly incorporated by reference herein).

Also, the methods of the present invention may be used to treat subjects deficient in FVIII, and the method may further comprise administering FVIII or a procoagulant bypassing agent. Suitable FVIII products are all commercially available plasma-derived and recombinant FVIII products. Suitable bypassing agents are activated prothrombin complex concentrates such as FEIBA VH Immuno (Baxter BioScience, Vienna, Austria) or rhFVIIa (NovoSeven®, Novo Nordisk, Denmark) or another FVIIa variant or mutein. The patient may also have inhibitor antibodies against FVIII. Typically, inhibitor patients are treated with a bypassing agent, such as FEIBA or rhFVIIa. Such inhibitor patients may have either a high titer response of greater than 5BU or a low titer response of between 0.5 and 5 BU. For clinical purposes, the magnitude of the antibody response can be quantified through the performance of a functional inhibitor assay from which the Bethesda unit (BU) inhibitor titer can be obtained. The International Society of Thrombosis and Haemostasis (ISTH) definition of a high titer response is >5BUs and its definition of a low titer response is between 0.5 and 5 BUs. The magnitude of the antibody response to FVIII can be quantified using a functional inhibitor assay, such as that described in Kasper C K et al (1975) Proceedings: A more uniform measurement of FVIII inhibitors. *Thromb. Diath. Haemorrh.* 34(2):612.

In some embodiments, the treated subject may be deficient in FIX, and the method may further comprise administering FIX. All commercially available recombinant and plasma-derived FIX-products may be suitable, including FIX is Bebulin VH® FIX complex (Baxter BioScience, Vienna, Austria). In this embodiment of the invention, the patient may have inhibitor antibodies against FIX. FIX inhibitors could be quantified by an aPTT assay as described by Kasper (supra). Suitably, rhFVIIa (NovoSeven®) and/or FEIBA are also administered to the FIX deficient subject.

The FVa and FVIIa compositions used in the subject invention will preferably contain one or more excipients known in the art to be suitable in formulating these factors in a form suitable for clinical use and/or maintaining storage stability. For example, an FVa (preferably an APC resistant FVa) and/or FVIIa (preferably rhFVIIa (NovoSeven®)) containing composition for use in the invention may comprise one or more pharmaceutically acceptable such as are described in "Remington: The Science & Practice of Pharmacy", 19th ed., Williams & Williams, (1995), the "Physician's Desk Reference", 52nd ed., Medical Economics, Montvale, N.J. (1998), and Kibbe, A. H., Handbook of Pharmaceutical Excipients, 3rd Edition, American Pharmaceutical Association, Washington, D.C., 2000. Exemplary excipients include, without limitation, carbohydrates, inorganic salts, antimicrobial agents, antioxidants, surfactants, buffers, acids, bases, and combinations thereof. Excipients suitable for injectable compositions include water, alcohols, polyols, glycerine, vegetable oils, phospholipids, and surfactants. A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like. The excipient can also include an inorganic salt or buffer such as citric acid, sodium chloride, potassium chloride, sodium sulfate, potassium nitrate, sodium phosphate monobasic, sodium phosphate dibasic, and combinations thereof.

Preferred excipients or carriers in the subject compositions may include $CaCl_2$, bovine serum albumin or human serum albumin, and combinations of the foregoing.

The amount of the FVa and FVIIa contained in the composition may vary depending on a number of factors, but will optimally be a therapeutically effective dose that elicits a synergistic effect on the inhibition of bleeding and the promoting of coagulation by synergistically promoting the generation of thrombin when the composition is in a unit dosage form or container (e.g., a vial).

The subject compositions may optionally include one or more additional agents, such as hemostatic agents, other blood factors, or other medications used to treat a subject for a condition or disease. Particularly preferred are compounded preparations including one or more blood factors such as FXI, FVIII, FIX, FX, FXIII, FII, and von Willebrand factor. Preparations may also include prekallikrein, high molecular weight kininogen (HMWK) and/or factor XII. Such compositions may also include other procoagulants, such as an activator of the intrinsic coagulation pathway, including but not limited to, FXa, FIXa, FXIa, FXIIa, and kallikrein; or an activator of the extrinsic coagulation pathway, including but not limited to, tissue factor, thrombin, and FXa.

The composition or compositions respectively comprising one or both of the FVa and FVIIa are typically, although not necessarily, administered orally, via injection (subcutaneously, intravenously or intramuscularly), by infusion, or locally. The pharmaceutical preparation or composition can be in the form of a liquid solution or suspension immediately prior to administration, but may also take another form such as a syrup, cream, ointment, tablet, capsule, powder, gel, matrix, suppository, or the like. Additional modes of administration are also contemplated, such as pulmonary, rectal, transdermal, transmucosal, intrathecal, pericardial, intra-arterial, intracerebral, intraocular, intraperitoneal, and so forth. The respective pharmaceutical compositions may be administered using the same or different routes of administration in accordance with any medically acceptable method known in the art.

Typically, the FVa and the FVIIa are administered contemporaneously to each other and may be in the same or different compositions. However, as noted these moieties may be administered at different times and such administration may be effected in either order. Based on the information contained in this application a skilled artisan will be able to select an appropriate dosage to achieve the desired effect, preferably synergistic effect on the prevention or treatment of bleeding, e.g., as a result of a genetic disorder, acquired condition, or the result of excessive APC generation or APC administration. The dosage and dosage regimen will depend on factors such as the specific bleeding disorder treated, age and heath of treated subject, any other treatments being effected and the like.

Exemplary dosing schedules for different indications wherein the subject combination will be of use in treating or preventing hypocoagulation or bleeding are set forth below. It should be understood that these regimens are intended to be exemplary and not exhaustive of suitable dosing schedules and bleeding conditions treatable by the present invention.

|  | Low dose | Medium dose | High dose |
|---|---|---|---|
| $^{super}$FVa* (Single dose) |  |  |  |
| Dose range (μg/mL plasma) | ~0.006-0.6 | ~0.6-6.0 | ~6-60 |
| Dose range (μg/kg body weight)* | ~0.27-27 | ~27-270 | ~270-2700 |
| FVIIa (Single dose) |  |  |  |
| Dose range (μg/mL plasma) | ~0.006-0.06 | ~0.06-0.6 | ~0.6-6[#] |
| Dose range (μg/kg body weight) | ~0.27-2.7 | ~2.7-27 | ~27-270[#] |
| aPCC concentrates (such as FEIBA) (Single dose) |  |  |  |
| Dose range (units/kg body weight) | ~1-25 | ~25-50 | ~50-100 |

*calculation based on the fact that plasma volume = 45 mL/kg body weight.
[#]the upper dose limit of 6 ug/mL or 270 μg/kg body weight was chosen based on the fact that some physicians exceed the labeled dose of FVIIa (90 μg/kg) 3-fold (270 μg/kg) on occasions for improved efficacy in non-responders.

Exemplary Dosing Regimens

1) Acute bleeding: Single dose parenteral administration of $^{super}$FVa at low dose, medium dose or high dose alone or in combination with single dosing of FVIIa or aPCC or PCC or 3-factor PCC or 4-factor PCC or FEIBA or fresh frozen plasma at low dose, medium dose or high dose simultaneously or alternating repeatedly until optimal response for acute bleeding. Dosing intervals may span from every 2 hours to every 4 hours to every 8 hours to every 12 hours to every 24 hours to every 48 hours to every 72 hours simultaneously or alternating.

2) Acute bleeding: Continuous infusion or continuous parenteral administration of $^{super}$FVa at 0.0001-2700 μg/kg body weight per hour alone or in combination with single dose infusion of FVIIa or aPCC at low, medium or high dose. Dosing intervals for FVIIa or aPCC or PCC or 3-factor PCC or 4-factor PCC or FEIBA or fresh frozen plasma may span from every 2 hours to every 4 hours to every 8 hours to every 12 hours to every 24 hours to every 48 hours to every 72 hours until optimal response for acute bleeding.

3) Acute bleeding: Same as in 1) or 2) in combination with FV Leiden- or FV Cambridge- or FVIII- or FIX- or FX-product. For FVIII- or FIX- or FX-product single dose infusion or parenteral administration at ~1-300 units per kg body weight until optimal response for acute bleeding. Dosing intervals may span from every 2 hours to every 4 hours to every 8 hours to every 12 hours to every 24 hours to every 48 hours to every 72 hours simultaneously or alternating.

4) Bleed prophylaxis or bleed prevention: Single dose parenteral administration of $^{super}$FVa at low dose, medium dose or high dose alone or in combination with single dose of FVIIa or aPCC or PCC or 3-factor PCC or 4-factor PCC or FEIBA or fresh frozen plasma at low dose, medium dose or high dose simultaneously or alternating. Dosing intervals for prophylactic use may span from every 8 hours to every 12 hours to every 24 hours to every 48 hours to every 72 hours to weekly simultaneously or alternating.

In certain aspects of the invention, $^{super}$FVa is administered as a monotherapy for various bleeding disorders and conditions, e.g., hemophilia, traumatic bleeding and NOAC-induced bleeding. Exemplary dosing schedules and ranges for $^{super}$FVa as a monotherapy to treat these conditions are provided below:

In hemophilia with inhibitors, the dose of $^{super}$FVa is about 4-2000 U/kg or about 0.01-8.0 mg/kg, preferably about 40-200 U/kg or about 0.1-0.8 mg/kg.

In acute traumatic coagulopathy, the dose of $^{super}$FVa is about 20-10,000 U/kg or about 0.06-35 mg/kg, preferably about 200-1000 U/kg or about 0.6-3.5 mg/kg.

In NOAC-mediated bleeding, the dose of $^{super}$FVa is about 40-200 U/kg or about 0.1-0.8 mg/kg.

Dosing can be a single bolus or a bolus infusion over 10 min, 20 min, 30 min or 60 min. Dosing can be a continuous infusion for 1 hour, 2 hour, 4 hour, 6 hour, 8 hour, 12 hour, 24 hour, 36 hour, 48 hour, 72 hour, 96 hour, or as long as required to resolve the bleeding episode or coagulopathy. Dosing can be a single bolus or a bolus infusion repeated every 2 hours, every 4 hours, every 6 hours, every 8 hours, every 10 hours, twice daily, once daily, every other day, twice weekly, or once weekly for as long as required to resolve the bleeding episode or coagulopathy or indefinitely when used as a prophylactic or preventative treatment.

In other aspects of the invention, $^{super}$FVa is administered along with other pharmaceutically active agents in a combination therapy for various bleeding disorders and conditions, e.g., hemophilia, traumatic bleeding and NOAC-induced bleeding. Exemplary dosing schedules and ranges for $^{super}$FVa when used in combination therapy are provided below:

For example, when used in combination therapy, the dose of $^{super}$FVa may be about 4-20 U/kg or 0.01-0.08 mg/kg, preferably about 0.04-2 U/kg or about 0.001-0.008 mg/kg, to treat acute traumatic coagulopathy; about 20-100 U/kg or 0.06-0.35 mg/kg, preferably about 2-10 U/kg or about 0.0006-0.035 mg/kg, to treat acute traumatic coagulopathy; or about 4-20 U/kg or 0.01-0.08 mg/kg, preferably about 0.04-2 U/kg or about 0.001-0.008 mg/kg, to treat NOAC-mediated bleeding, when used in combination with a clinical dose of FVIIa (90 µg/ml) or a high clinical dose of FVIIa (270 µg/ml) or a clinical dose of FEIBA (25-50 U/kg).

Alternatively, to treat hemophilia with inhibitors and/or NOAC-mediated bleeding, a dose of about 40-200 U/kg or 0.1-0.8 mg/kg, preferably about 4-20 U/kg or about 0.01-0.08 mg/kg, more preferably about 0.4-2 U/kg or about 0.001-0.008 mg/kg, most preferably about 0.04-0.2 U/kg or about 0.0001-0.0008 mg/kg of $^{super}$FVa may be administered along with about 90-270 gig/ml, preferably about 9-27 µg/ml, more preferably about 0.9-2.7 µg/ml, most preferably about 0.009-0.27 µg/ml of FVIIa; or about 25-50 U/kg, preferably 2.5-5.0 U/kg, more preferably about 0.25-0.5 U/kg, most preferably about 0.025-0.05 U/kg of FEIBA; or about 1-100 U/kg, preferably about 0.1-10 U/kg, more preferably about 0.01-1 U/kg, most preferably about 0.001-0.1 U/kg of PCC.

Additionally, to treat acute traumatic coagulopathy, a dose of about 200-1000 U/kg or about 0.6-3.5 mg/kg, preferably about 20-100 U/kg or about 0.06-0.35 mg/kg, more preferably about 2-10 U/kg or about 0.006-0.035 mg/kg, most preferably about 0.2-1 U/kg or about 0.0006-0.0035 mg/kg of $^{super}$FVa may be administered along with about 90-270 µg/ml, preferably about 9-27 µg/ml, more preferably about 0.9-2.7 µg/ml, most preferably about 0.009-0.27 µg/ml of FVIIa; or about 25-50 U/kg, preferably 2.5-5.0 U/kg, more preferably about 0.25-0.5 U/kg, most preferably about 0.025-0.05 U/kg of FEIBA; or about 1-100 U/kg, preferably about 0.1-10 U/kg, more preferably about 0.01-1 U/kg, most preferably about 0.001-0.1 U/kg of aPCC.

In yet other aspects of the invention, the combination therapy involving $^{super}$FVa also includes alternate dosing of $^{super}$FVa and a second pharmaceutically active agent, e.g., FVIIa, FEIBA, and aPCC. For example, when $^{super}$FVa may be administered 1 hour, 2 hours, 4 hours or 6 hours after a clinical dose of FVIIa to make use of the natural "washout period" for FVIIa to lower its concentration for synergy with $^{super}$FVa.

The invention is also understood to encompass isolated nucleic acids encoding a $^{super}$FVa, preferably a $^{super}$FVa having 90% sequence identity to SEQ ID NO:4, more preferably a $^{super}$FVa having 95% sequence identity to SEQ ID NO:4, and most preferably a $^{super}$FVa of SEQ ID NO:4. Also, the invention includes host cells, e.g., bacteria, yeast, mammalian cells, that contain the isolated nucleic acid encoding a $^{super}$FVa. Thus, the present invention should be understood to further include methods for recombinant production of an activated form of FV, such as the $^{super}$FV of SEQ ID NO:4, comprising culturing a host cell containing the nucleic acid under conditions suitable for FV production and optionally isolating and purifying said activated form of FV.

The present invention has been described in detail. In order to further illustrate the present invention and its intrinsic benefits the following examples discussing experiments conducted by the inventors are provided.

WORKING EXAMPLES

Materials and Methods Used in Examples

Materials

Normal pooled human plasma and plasma from human FVIII-deficient patients with and without inhibitors (titer specified in Bethesda Units (BU)) was purchased from George King Bio-Medical (Overland Park, Kans., USA). In addition, plasma and clinical information was obtained from two patients with severe FVIII-deficiency (<1% intrinsic FVIII-activity levels) and inhibitors (titers determined in BU by the clinical laboratory using the Nijmegen assay (17) regularly visiting the Hemophilia Treatment Center at the University of California, San Diego (UCSD) after informed consent was obtained. Patient confidentiality safeguards, sample and data acquisition methods were approved by the UCSD Institutional Review Board. Blood was drawn into 3.8% sodium citrate (pH 5.5) at a 9:1 blood/anticoagulant volume ratio, and processed immediately. Plasma was collected and frozen at −80° C. after centrifugation at 2600×g for 15 minutes. The following reagents were used: Thrombin from Enzyme Research Laboratories (South Bend, Ind., USA), hirudin from Calbiochem (San Diego, Calif., USA), Corn trypsin inhibitor (CTI) from Enzyme Research Laboratories, thrombin calibrator from Synapse BV (distributed by Diagnostica Stago), Substrate Z-Gly-Gly-Arg-AMC from Bachem (Bubendorf Switzerland), recombinant human tissue factor (TF), Dade Innovin from Dade Behring (Newark, Del., USA), mouse anti-human FVIII (GMA8015) and isotype antibody (GMA650) from Green mountain antibodies (Burlington, Vt., USA), recombinant human FVIIa, NovoSeven®, from NovoNordisk (Bagsvaerd, Denmark), Phospholipid vesicles (80% phosphatidylcholine (PC), 20% phosphatidylserine (PS)) were purchased from Avanti Lipids (Alabaster, Ala., USA) and prepared as described (18).

Protein Preparation

Recombinant super factor five ($^{super}$FV) (M. wt. 174 kDa) was made on a B-domain deleted S2183A FV platform and purified from conditioned media of stable transfected BHK cells by a combination of affinity chromatography using anti-FV 3B1 and HV5101 monoclonal antibodies as described (16). SuperFV protein concentration was determined by absorbance at 280 nm using FV ε1%=16.9 (calculated based on amino acid composition and MW of 174 kDa using DNASTAR Lasergene (Madison, Wis.)) and ELISA (Enzyme Research Laboratories) according to manufacturer's instructions. $^{super}$FV protein was activated with 2 nM thrombin for 20 minutes at 37° C. in prothrombinase buffer (50 mM HEPES, 150 mM NaCl, 0.5% BSA, 5 mM CaCl$_2$ and 0.1 mM MnCl$_2$). Activation was terminated by the addition of 1.1 molar equivalent of hirudin.

Activated Protein C (APC)

Human recombinant or plasma-derived APC, and murine recombinant APC was used as indicated in the different experiments. For a human source of APC, recombinant human (rh) APC (Xigris®, Eli Lilly, Indianapolis, Ind., USA) was used, and reconstituted according to the manufacturer's specification. Recombinant murine APC was purified and prepared as previously described (5).

Thrombin Generation Assays

Endogenous thrombin potential (ETP) assays were performed as described (19). Briefly, plasma samples supplemented with CTI, TF, PCPS vesicles and coagulation factors were preincubated with the plasma at 37° C. Thrombin generation was initiated by addition of CaCl$_2$ and Z-Gly-Gly-Arg-AMC in HBS/0.5% BSA. The final reaction mixture contained, 50% plasma, 0.2 pM TF, 4 M PCPS vesicles, 0.725 μM CTI, 0.5 mM Z-GGR-AMC and 7.6 mM CaCl$_2$ in a total volume of 100 μL. In some experiments, 1.25 μg/ml anti-FVIII antibody was added to the plasma and ETP was determined after 1 hour of preincubation. Fluorescence was measured at excitation/emission wavelengths of 360/460 nM using Gemini EM fluorescent plate reader (Molecular Devices). Fluorescence time course data were converted to nM thrombin as described (20). ETP, defined as the area under the curve (AUC) and the peak height were determined using Origin or GraphPad Prism software.

BU titer values for FVIII antibodies added to FVIII-deficient plasma were determined using a modified Nijmegen Bethesda assay (Barrow and Lollar; JTH 2006, 4:2223-2229). Briefly, antibody was serially diluted in HBS with 0.05% Tween 80 and mixed 1:1 with pooled normal plasma that was supplemented with 100 mM Imidazole, pH 7.0. Samples were incubated at 37° C. for 2 hours then assayed by aPTT with APTT XL reagent (Pacific Hemostasis). A standard curve was derived from a serial dilution of normal plasma into FVIII deficient plasma that was also mixed 1:1 with HBST and incubated at 37° C. for 2 hours. Percent FVIII activity was plotted versus mg/ml of antibody and residual activity of 50% was defined as 1 BU/ml. In addition, endogenous thrombin potential (ETP) assays were performed as described (3). Briefly FVa mutants or saline were added to human or murine plasma (George King Bio-Medical; mouse source, 50% v/v) supplemented with 1.45 M corn trypsin inhibitor (Haematologic Technologies), 10 mM CaCl$_2$, 10 μM phospholipid vesicles (80% phosphatidylcholine, 20% phosphatidylserine, prepared as described (6), 0.2 pM soluble tissue factor (Innovin®, Dade Behring), and 0.4 mM Z-Gly-Gly-Arg-AMC (thrombin substrate, Bachem) in HBS. After mixing, 100 μL was transferred to a FluoroNunc microtiter plate at 37° C. to monitor fluorescence (excitation at 360 nm/emission at 460 nm; Gemini EM fluorescent plate reader (Molecular Devices)). Fluorescence time course data were converted to nM thrombin as described (7). ETP, defined as the area under the curve, was determined using Prism 5.04 (Graphpad).

FVA Inactivation Assays

APC-mediated inactivation of FVa was analyzed in ETP assays and aPTT clotting assays. FVa mutants were incubated with equal volumes of either recombinant human APC (Xigris®) or buffer in human and murine Balb/c plasma.

APTT Clotting Assays

Plasma (50 μL) was mixed with 50 μL of a PTT reagent (APTT-XL, Pacific Hemostasis) and incubated at 37° C. for 3 minutes in the presence of FVa either with recombinant human APC or buffer. Following addition of 25 μL of 50 mM CaCl$_2$ in HBS, 0.5% BSA, the clotting time was recorded using an ST4 coagulometer (Diagnostica Stago).

Ex-Vivo APTT Clotting Assays

Recombinant murine APC was administered intravenously to Balb/c mice by tail vein injection 2 minutes prior to retroorbital blood harvest in siliconized microcapillaries (75 μL) prefilled with 20 μL Sodium-Citrate (3.8%). Whole blood aPTT was performed immediately, whereby 50 μL of blood were mixed with 50 μL of aPTT reagent (APTT-XL, Pacific Hemostasis) and incubated at 37° C. for 3 minutes in the presence of FVa or buffer. Following addition of 25 μL of 130 mM CaCl$_2$ in HBS, 0.5% BSA, the clotting time was recorded using an ST4 coagulometer (Diagnostica Stago).

Tail Clip Bleeding Assay

Mice were anesthetized with Isoflurane 3%, placed on temperature controlled heating pads (37° C.), and the distal portion of the tail was cut at 1.5 mm diameter after which the tail was immersed in a predefined volume of 37° C. saline (0.9% NaCl) for 20 minutes. To study effects on bleeding and clot stability, tubes were changed after 10 minutes to collect blood for the first and second 10 minutes separately. Blood loss was determined by the hemoglobin concentration in the saline solution after red cell lysis with 2% acetic acid and measured by absorbance at 490 nm. Using a hemoglobin standard derived from defined blood volumes, blood loss was calculated assuming a hematocrit of 46% and expressed in μL/g body weight. Groups of Balb/c mice were injected intravenously (tail vein) with equal volumes (200 μL) of $^{super}$FVa or saline 2 minutes prior to intravenous injection of rhAPC (Xigris®). Immediately after APC injection tail cut was performed. All agents were diluted in sterile sodium chloride 0.9% for injection (Hospira Inc).

Liver Laceration Bleeding Assay

Mice were anesthetized with Isofluorane 3% and the abdomen was opened by substernal blunt midline dissection. The liver was mobilized and externalized onto sterile gauze, followed by a defined 10 mm scalpel cut through the left liver lobe which resulted in complete ventral and dorsal laceration. Immediately after laceration mice were positioned prone into a small weighing dish (8 cm diameter) filled with saline (37° C., 13 mL), transferred into the anesthesia chamber which rested on a heating pad (37° C.). Anesthesia was maintained at 3% Isofluorane and dishes were changed after 10 minutes to collect blood for the first and second 10 minutes separately. Blood loss was determined as described for the tail clip model. Groups of Balb/c mice were injected intravenously (tail vein) with equal volumes (200 μL) of $^{super}$FVa or saline 2 minutes prior to intravenous injection of plasma-derived human APC, followed immediately by liver laceration. All agents were diluted in sterile sodium chloride 0.9% for injection (Hospira Inc).

Statistical Analysis

Two-sided Student's t test was used to assess statistical significance where appropriate. A p-value of ≤0.05 was considered statistically significant.

Example 1

This example relates to the experiments the results of which are contained in FIGS. 1A and 1B. These experiments illustrate the synergistic effects of FVIIa and $^{super}$FVa in FVIII-deficient plasma. In these experiments, thrombin generation was determined as ETP and peak height in FVIII-deficient plasma supplemented with increasing concentrations of $^{super}$FVa in the absence or presence of a fixed concentration of rhFVIIa (NovoSeven®, 25 ng/mL). Panel (A) in the figure is a representative example of ETP at increasing concentrations of $^{super}$FVa in the absence (top panel) or presence of rhFVIIa (bottom panel). Panel (B) depicts the amount of ETP (Endogenous Thrombin Potential) (top panel) and peak height (bottom panel) achieved with increasing concentrations of $^{super}$FVa in the absence (black curve) or presence of rhFVIIa (red curve). In the figure the error bars represent standard error of the mean (n≥5). These results statistically demonstrate the synergistic effects of the combination on ETP and peak height and based thereon on thrombin generation.

Example 2

This example relates to the experiments the results of which are contained in FIGS. 2A and 2B. These experiments further show the synergistic effect of FVIIa and $^{super}$FVa in FVIII-deficient plasma. In the experiments, thrombin generation was determined as ETP and peak height in FVIII-deficient plasma supplemented with increasing concentrations of rhFVIIa (NovoSeven®) in the absence or presence of a fixed concentration of $^{super}$FVa (0.59 µg/ml). Panel (A) contains a representative example of ETP at increasing concentrations of rhFVIIa in the absence (top panel) or presence of $^{super}$FVa (bottom panel). Panel (B) shows ETP (top panel) and peak height (bottom panel) achieved with increasing concentrations of rhFVIIa in the absence (black curve) or presence of $^{super}$FVa (red curve). The error bars again represent standard error of the mean (n≥5). These results also statistically demonstrate the synergistic effects of the combination on ETP and peak height and based thereon on thrombin generation.

Example 3

This example relates to the experiments the results of which are contained in FIGS. 3A and 3B. These experiments further demonstrate the synergistic effect of FVIIa and $^{super}$FVa in normal human plasma with anti-FVIII antibody (inhibitor). Thrombin generation was again determined as ETP (top panels) and peak height (bottom panels) in normal human plasma supplemented with 1.25 µg/ml anti-human FVIII-antibody. Panel (A) shows thrombin generation with increasing concentrations of $^{super}$FVa in the absence (black curve) or presence of a fixed dose of rhFVIIa (NovoSeven®, 25 ng/ml) (red curve) concentration. Panel (B) shows thrombin generation with increasing concentrations of rhFVIIa in the absence (black curve) or presence of a fixed dose of $^{super}$FVa (red curve) concentration. Endogenous Thrombin Potential; ETP. $^{super}$FVa; SFVa. The error bars again represent standard error of the mean (n≥5). These results also statistically demonstrate the synergistic effects of the combination on ETP and peak height and based thereon on thrombin generation.

Example 4

This example relates to the experiments the results of which are contained in FIGS. 4A and 4B. These experiments further illustrate the synergistic effect of FVIIa and $^{super}$FVa in plasma of patients with congenital FVIII-deficiency and high titer anti-FVII antibodies (inhibitors). In particular, the procoagulant effects of $^{super}$FVa and/or rhFVIIa were also studied in patients with congenital FVIII-deficiency and inhibitors. ETP of 2 clinic collected and 3 commercial plasma samples from patients with high titer inhibitor (clinic samples BU-titer=64 for both patients; commercial samples BU-titer=41, 150 and 280) were studied at baseline, in the presence of 2 different concentrations of $^{super}$FVa or rhFVIIa, or combinations of both. Results were compared to the ETP of NHP (FIG. 4A/B). RhFVIIa or $^{super}$FVa increased ETP and peak height in all five patient samples. ETP and peak height were comparable between plasmas spiked with 40 nM rhFVIIa (therapeutic concentration of rhFVIIa) and $^{super}$FVa at 3.3 nM. Notwithstanding inter-individual responses to factor substitution, ETP and peak height increased noticeably in all patient samples when rhFVIIa (40 nM; therapeutic concentration) and $^{super}$FVa (3.3 nM) were combined, demonstrating an ~1.5- to 3-fold increase compared to either factor alone. When lowering the concentration of rhFVIIa by 20-fold, from 40 nM to 2 nM in the presence of $^{super}$FVa at 3.3 nM, effects on ETP and peak height remained comparable to the combination therapy with rhFVIIa at 40 nM. However, increasing the concentration of $^{super}$FVa to 30 nM in the presence of only 2 nM rh FVIIa, appeared to further increase ETP and/or peak height in several patient samples. Effects were most pronounced in the clinical collected samples, where with factor combination ETPs became comparable to the ETP of normal pooled plasma (FIG. 4A).

These results statistically demonstrate the synergistic effects of the combination on coagulation or clotting and thrombin generation (as evidenced by increased ETP and peak height).

Example 5

Figure 5:
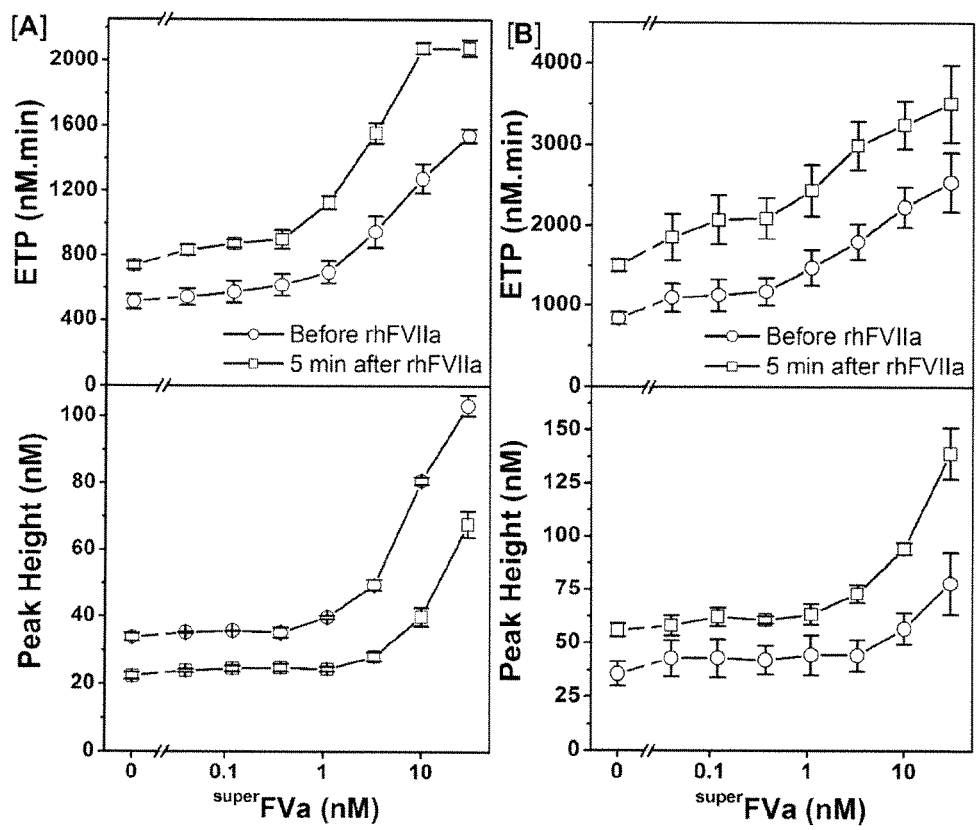

This example relates to the experiments the results of which are contained in FIG. 5. In particular, the effects of $^{super}$FVa were also studied directly in two different patients with congenital FVIII-deficiency and high titer inhibitor (Patient A, BU=64; Patient B, BU=32), immediately before and 5 minutes after treatment with rhFVIIa at 90 µg/kg for acute joint or muscle bleeding. Treatment with rhFVIIa resulted in ~1.5 to 2 fold increase of ETP and peak height over baseline in both patients. Addition of increasing concentrations of $^{super}$FVa to patient plasma ex vivo resulted in an additional ~3-fold increase of ETP and peak height in the plasma harvested before and 5 minutes after rhFVIIa infusion (FIG. 5). ETP, but not peak height plateaued at 10 nM $^{super}$FVa for Patient A.

These experiments illustrate the synergistic effect of $^{super}$FVa in the plasma of a patient with congenital FVIII-deficiency and high titer anti-FVIII antibodies treated with rhFVIIa (NovoSeven®) for acute joint bleeding. Blood samples were obtained just before (black curve) and 5 minutes post infusion of rhFVIIa at 90 µg/kg (red curve). BU-titer=64 U/ml. Thrombin generation was determined as ETP (top panel) or peak height (bottom panel) with increasing concentrations of $^{super}$FVa added to plasma samples ex vivo. These results statistically demonstrate the synergistic effects of the combination on coagulation or clotting and thrombin generation based on detected ETP and peak height.

Example 6

This example relates to the clotting experiments the results of which are contained in FIGS. 8A and B. In this experiment, thrombin generation was determined in A) murine Balb/c plasma and B) normal human plasma supplemented with rhFVa or rh$^{super}$FVa in the presence of rhAPC. Thrombin generation was expressed as area under curve (AUC) (n=4-6). Error bars represent standard error of the mean. * denotes statistical significance (all p-values <0.001.

Example 7

This example relates to the experiments the results of which are contained in FIGS. 9A, 9B and 9C. In these experiments aPTT correction is demonstrated. Particularly, as shown in FIG. 9, aPTT clotting times were determined in human plasma in the presence of A) increasing concentrations of rhFVa or rh$^{super}$FVa in the presence of 10 nM rhAPC (n=4), in FIG. 9B aPTT correction is depicted as a single data point at 10 nM rhAPC and 1 nM rh FVa variants, and in FIG. 9C aPTT correction is shown using murine plasma in the presence of rhFVa variants (n=10). Error bars represent standard error of the mean. * denotes statistical significance (all p-values <0.001.

Example 8

This example relates to the experiments the results of which are contained in FIG. 10. In the experiments aPTT correction is demonstrated with FVa variants after intravenous injection of recombinant murine APC into Balb/c mice. Mice were injected intravenously with saline or rmAPC (0.5 mg/kg). Two minutes later blood was collected retroorbitally and whole blood aPTT was determined immediately. In the two groups of mice that were injected with APC whole blood was spiked ex vivo with either $^{super}$FVa or wt FVa (open triangles 1 U/mL, open circles 0.5 U/mL, closed triangles 0.05 U/mL) to determine the extent of aPTT correction with both variants. Error bars represent standard error of the mean. * denotes statistical significance (all p-values <0.001).

Example 9

This example relates to the experiments the results of which are contained in FIGS. 11A and 11B which demonstrate the correction of APC-induced bleeding by $^{super}$FVa in the murine tail clip model. Wild-type mice were injected intravenously with increasing doses of rhAPC or with saline. $^{super}$FVa was injected intravenously 2 minutes prior to APC at 2 concentrations. Bleeding after tail clip is expressed as blood loss in μl blood per gram mouse. FIG. 11A shows blood loss during 20 minutes, FIG. 11B shows this divided into 1$^{st}$ 10 minutes and FIG. 11C shows the 2$^{nd}$ 10 minutes after tail clip depicted. Error bars represent SEM. * denotes statistical significance (p-value <0.05).

Example 10

This example relates to the experiments the results of which are contained in FIG. 12. The experiments directly compare bleeding patterns following tail clip and liver laceration. FVIII-deficient mice were injected intravenously with saline (200 μL) or rhFVIII (50 U/kg; 200 μL) and subjected to tail clip or liver laceration. Wild-type Balb/c mice were injected with saline for baseline values. Blood loss in all groups of mice during 20 minutes was determined in both models.

Example 11

This example relates to the experiments the results of which are contained in FIGS. 13A-C which show the correction of APC-induced bleeding by $^{super}$FVa after liver laceration. In these experiments mice were injected intravenously with saline or plasma derived human APC at 1.25 mg/kg. $^{super}$FVa was injected intravenously 2 minutes prior to APC at 3.5 mg/kg. Bleeding after liver laceration is expressed as blood loss in μl blood per gram mouse. FIG. 13(A) shows blood loss and FIG. 13B survival during 20 minutes. FIG. 13C shows blood loss divided into 1$^{st}$ 10 minutes (top panel) and 2$^{nd}$ 10 minutes (bottom panel) after injury. Four of 13 mice injected with APC died during the 1st 10 minutes after injury (open circles). Three more mice died during the 2$^{nd}$ 10 minutes, respectively (open rectangles) and are therefore were excluded from bottom panel. Error bars represent standard error of the mean. * denotes statistical significance (all p-values ≤0.01).

Example 12

This example relates to the experiments the results of which are contained in FIGS. 14A and B. The experiments show the suppression of thrombin generation by rhAPC plasma and the dose response. In the experiments thrombin generation was determined in 14A) normal human plasma and 14B) mouse plasma in the presence of increasing of rhAPC. Thrombin generation was expressed as area under curve AUC.

Example 13

This example relates to the experiments the results of which are contained in FIGS. 15A and B. A The experiments show the prolongation of aPTT clotting times in plasma by rhAPC and the dose response. In this experiment APTT was determined in 15A) normal human plasma and 15B) murine plasma after supplementation with increasing concentrations of rhAPC (n=2-5). Error bars represent standard error of the mean.

Example 14

This example relates to the experiments the results of which are contained in FIGS. 16A and 16B, which demonstrate the rescue of APC-induced reduction of thrombin generation in human plasma. In the experiments thrombin generation was determined in normal human plasma as A) Area Under the Curve (AUC) and B) Peak Height in the presence of rhAPC. For rescue of thrombin generation $^{super}$FVa and rhFVIIa were applied either alone or in combination.

The results contained therein show that rhFVIIa alone, comprised at increasing concentrations had no effects on thrombin generation, while $^{super}$FVa corrected thrombin generation to levels to those of normal human plasma. In addition, the experiments showed that the addition of trace amounts of rhFVIIa (100 ng/mL) to $^{super}$FVa increased thrombin generation by approximately 50% above normal human plasma.

This experiment provides convincing evidence that the combination of rhFVIIa with superFVa synergistically increased thrombin generation which had been suppressed by APC in human plasma. The lowest optimal concentration ranges of $^{super}$FVa in combination with rhFVIIa to correct thrombin generation to normal was not effected but may be determined based on these results.

Example 15

This example relates to the experiments the results of which are contained in FIGS. 17-19 and 28.

The experiments contained in FIG. 17 show the results of a clot lysis assay performed to study the effect of anti-FVIII antibody on normal human plasma. Titration of anti-FVIII antibody showed that more than 5 µg/ml antibody was sufficient to decrease the clot lysis time to the level of CPI control.

Figure 18:
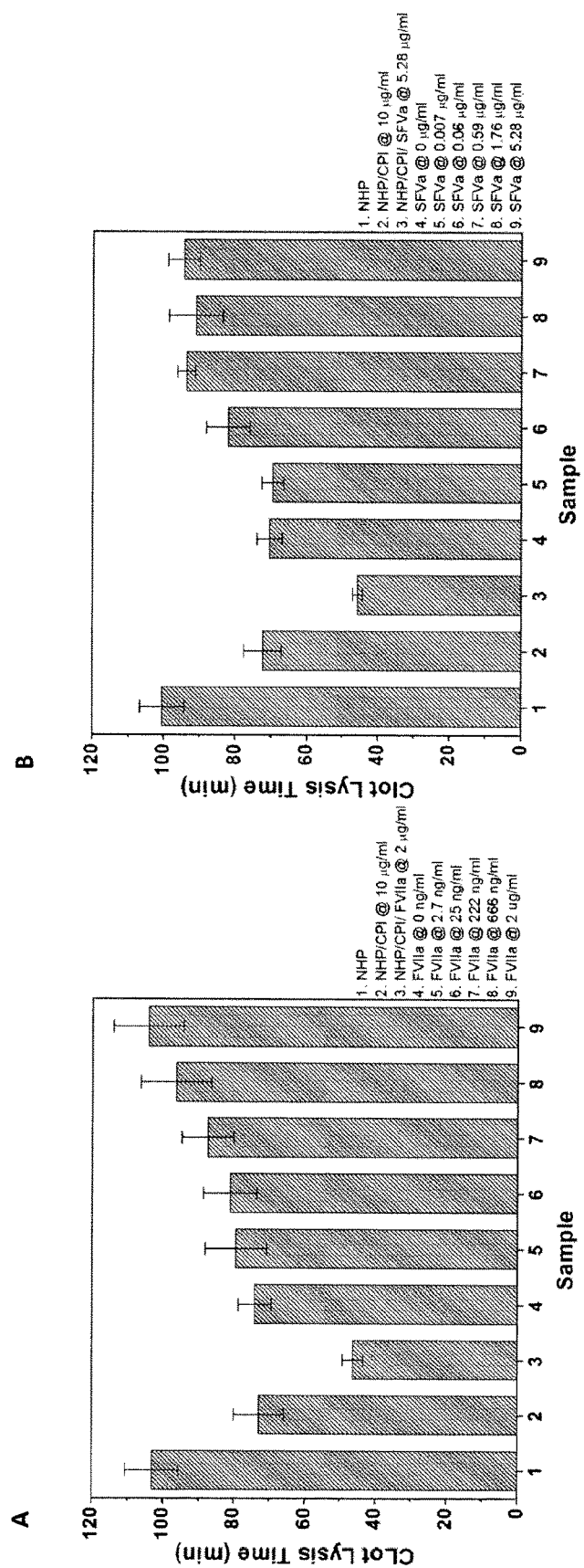

FIG. 18 contains the results of clot lysis assays, in which 10 µg/ml antibody concentration was used to study the effect of rhFVIIa and $^{super}$FVa individually and in a synergistic manner on the clot lysis of normal human plasma with inhibitor against FVIII. As shown therein the rhFVIIa and $^{super}$FVa individually showed an enhancement of clot lysis time in normal human plasma incubated with 10 µg/ml of anti-FVIII antibody at higher concentration of 2 µg/ml and ~2-5 µg/ml respectively.

Figure 19:
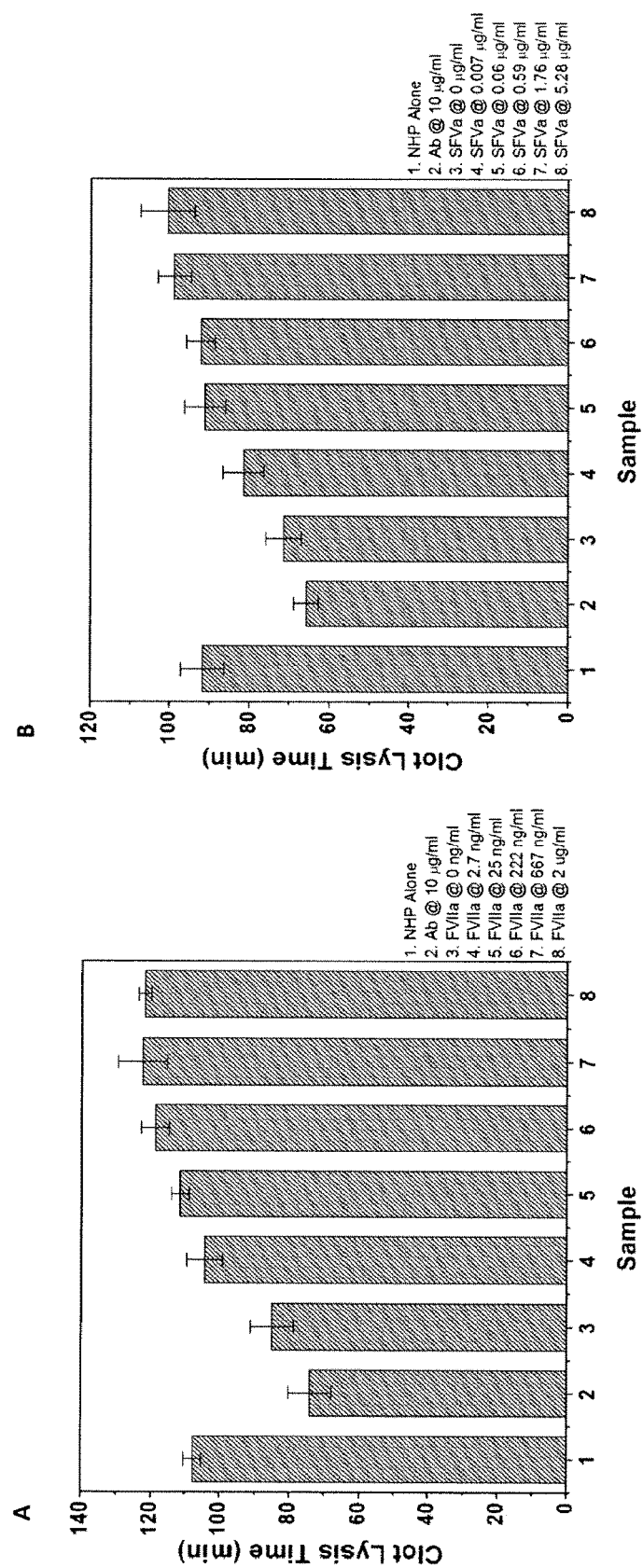

FIG. 19 contains clot lysis assays, in which rhFVIIa and $^{super}$FVa were used in combination. As shown by the data therein clot lysis time was observed to increase to the level of normal plasma at a decreased concentration of rhFVIIa by two orders of magnitude and in $^{super}$FVa to increase by more than an order of magnitude demonstrating a synergistic effect of both rhFVIIa and $^{super}$FVa in correcting the clot lysis time of normal human plasma comprising inhibitors against FVIII.

Figure 28:
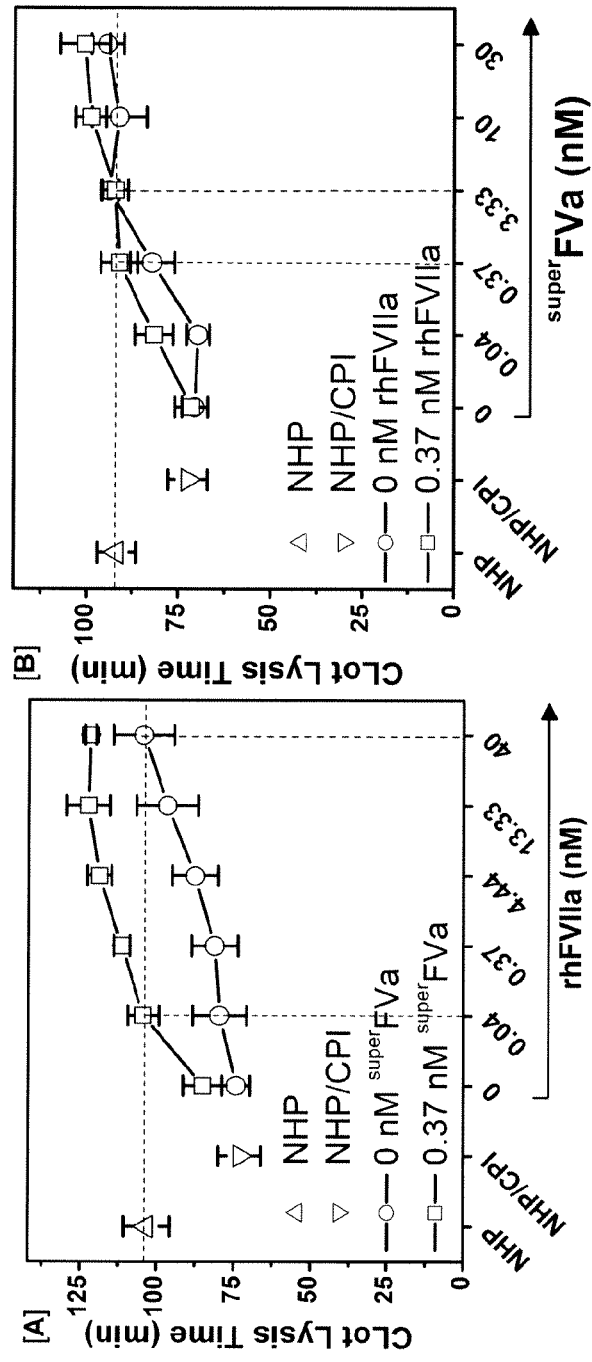

FIG. 28 shows the results of a clot lysis assay performed to study the effect of $^{super}$FVa and FVIIa, alone and in combination, on normal human plasma (NHP) spiked with anti-FVIII antibody. Clot lysis time was observed to return to normal at 40 nM rhFVIIa (therapeutic plasma concentration; FIG. 28A) or 3.33 nM $^{super}$FVa (FIG. 5B). However, the concentration of rhFVIIa required to normalize clot lysis times could be lowered by 100-fold (to ~0.4 nM) in the presence of trace amounts of $^{super}$FVa (0.37 nM) (FIG. 28A/B). Similar results were obtained when the experiments were performed in FVIII deficient plasma (FVIIIdP) (data not shown).

FIG. 31 shows the concentrations of rhFVIIa or $^{super}$FVa alone or in combination necessary to normalize clot lysis times to what is expected in NHP. In general, concentrations required to reach the mean clot lysis time of NHP were ~10-100 times lower for each factor when used in combination.

Results and Analysis
1. Effects of $^{super}$FVA and $FVII_A$ on Thrombin Generation in FVIII-Deficient Plasma The present inventors have demonstrated that $^{super}$FVa increases ETP in human FVIII-deficient plasma approximately 2-fold (von Drygalski A, et al. JTH 2014; 12:363-372, the disclosure of which is herein expressly incorporated by reference in its entirety). To study potential additive or synergistic effects of $^{super}$FVa in the presence of rhFVIIa thrombin generation was assessed in FVIII-deficient plasma at increasing concentrations of $^{super}$FVa alone or in combination with rhFVIIa. Increasing concentrations of $^{super}$FVa resulted in ~2.5-fold increase in ETP and peak height. Addition of FVIIa at a fixed dose of 25 ng/mL, which is ~100-fold lower than expected for therapeutic plasma levels after intravenous administration of FVIIa at 90 µg/kg body weight (~2 µg/mL), resulted in an additional ~2.5-fold increase of ETP and peak height at all concentrations of $^{super}$FVa (0.007 to 5.28 µg/mL). At the highest concentration of $^{super}$FVa (5.28 µg/mL), peak height in the presence of FVIIa rose to ~5-fold over what could be achieved with $^{super}$FVa alone (FIG. 1). Additionally, lag times to thrombin generation observed in FVIII-deficient plasma were abrogated in the presence of FVIIa (FIG. 1).

Figure 2:
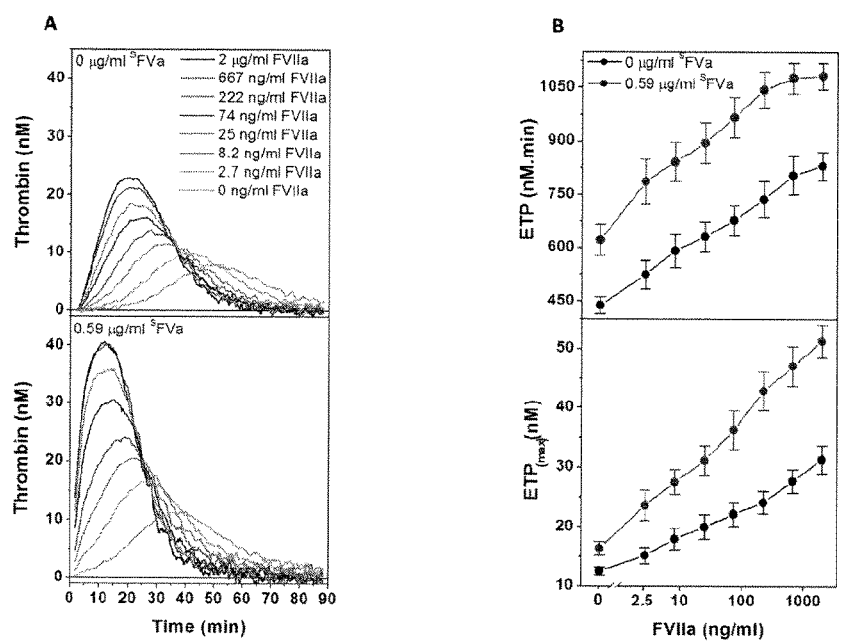

Subsequently, the reciprocal relationship of potential additive or synergistic effects of increasing concentrations of FVIIa on thrombin generation in the presence of low dose fixed $^{super}$FVa (0.59 µg/mL) were determined with thrombin generation in FVIII deficient plasma. An ~2-fold increase of ETP and peak height were noted at each concentration of rhFVIIa in the presence of $^{super}$FVa and lag times were abolished (FIG. 2).

Figure 3:
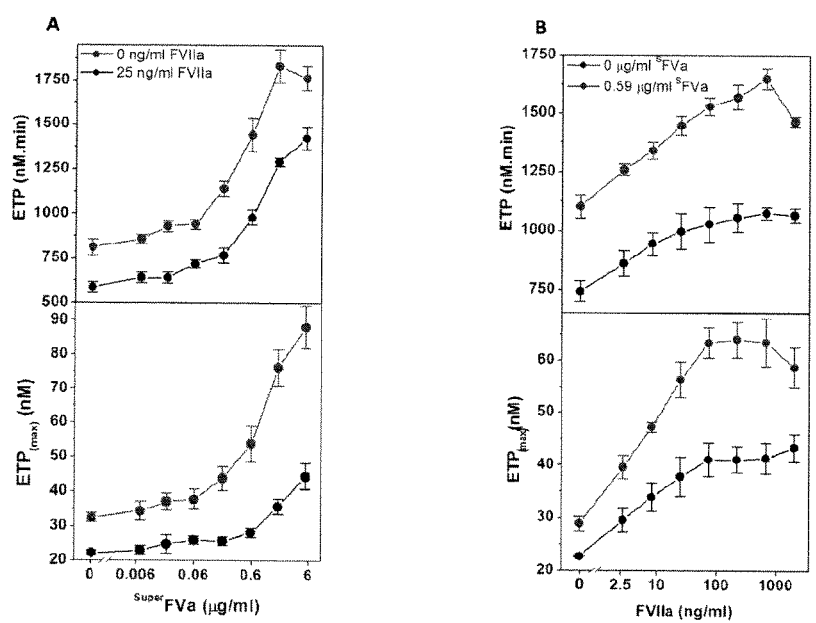

2. Effects of $^{super}$FVa and $FVII_A$ on Thrombin Generation in Normal Human Plasma with FVIII Inhibiting Antibodies To further evaluate the procoagulant effects of $^{super}$FVa alone or in combination with rhFVIIa in the presence of FVIII inhibiting antibodies (inhibitors) in normal human plasma the optimal concentration of anti-FVIII GMA8015 for maximal suppression of thrombin generation was determined first and found to be 1.25 µg/ml. (See FIG. 7.) Both, rhFVIIa or $^{super}$FVa alone were able to overcome suppression of thrombin generation and increased ETP and peak height compared to baseline approximately 1.5 to 2-fold. Of note, effects with rhFVIIa seemed to plateau at 200 ng/mL, which is ~10% of the usual therapeutic plasma concentration following intravenous administration of 90 µg/kg. When either trace amounts of rhFVIIa (25 ng/mL corresponding to ~1% usual therapeutic concentration) were combined with increasing concentrations of $^{super}$FVa, or trace amounts of $^{super}$FVa (0.59 µg/mL; usual plasma concentration of FV ~10 µg/mL) were combined with increasing concentrations of rhFVIIa, ETP and peak height increased significantly (FIG. 3). Both combinations yielded an additional ~1.5 to 2-fold increase of ETP, and a ~2 to 3-fold increase of peak height. Thrombin generation in normal human plasma with and without isotype antibody was similar, indicating that the antibody type did not interfere with thrombin generation. (See FIG. 7).

3. Effects of $^{super}$FVa and $FVII_A$ on Thrombin Generation in Plasma from Patients with Congenital FVIII-Deficiency and Inhibitors.

Figure 4:
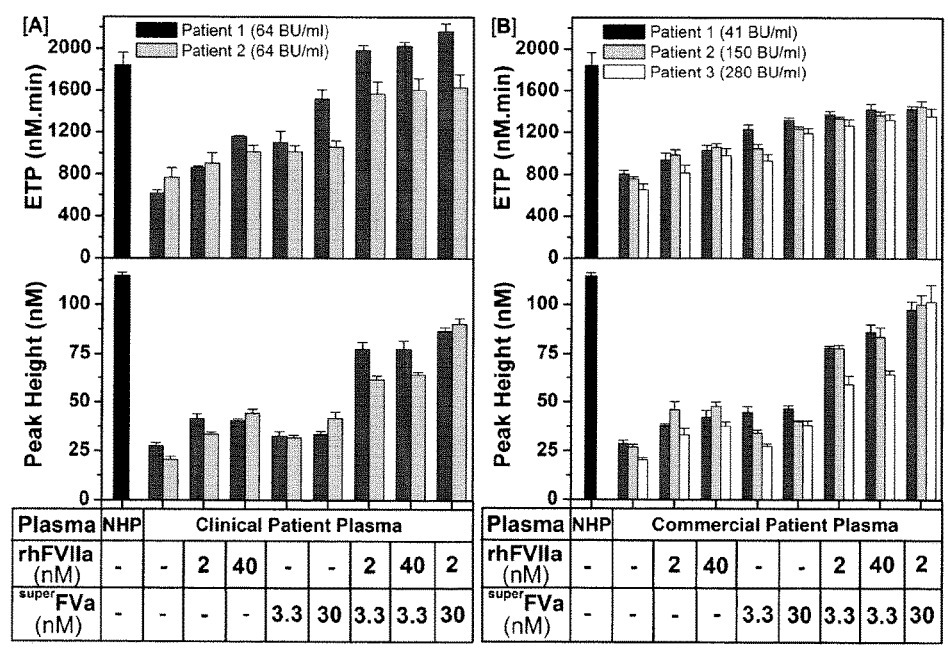

The procoagulant effects of $^{super}$FVa and/or rhFVIIa were also studied in patients with congenital FVIII-deficiency and inhibitors. ETP of three commercial and two clinic collected plasma samples from patients with high titer inhibitor (commercial samples BU-titer=41, 150 and 280; clinic samples BU-titer=64 for both patients) were assessed at baseline, in the presence of two different concentrations of $^{super}$FVa, rhFVIIa, or combinations of both. Results were compared to ETP of normal human plasma (FIG. 4). rhFVIIa or $^{super}$FVa increased ETP and peak height in all five patient samples. ETP and peak height were comparable between plasmas spiked with 2 µg/mL rhFVIIa (~expected therapeutic concentration of rhFVIIa) and $^{super}$FVa at 0.59 µg/mL ETP and peak height increased noticeably when rhFVIIa (2 µg/mL) and $^{super}$FVa (0.59 µg/mL) were combined. Notwithstanding inter-individual responses to factor substitution, the combination achieved an ~1.5- to 3-fold increase of ETP or peak height compared to either factor alone. Of note, effects with the combination were not compromised when the concentration of rhFVIIa was decreased by 20-fold from 2 µg/mL to 100 ng/mL ETP and peak height appeared to further increase when the concentration of $^{super}$FVa was increased to 1.76 µg/mL while maintaining FVIIa at 100 ng/mL (FIG. 4). Effects were most pronounced in the clinical collected samples, where with factor combination ETPs became comparable to the ETP of normal pooled plasma (FIG. 4B).

The effects of $^{super}$FVa were also studied directly in clinic collected plasma from one of the patient's with congenital FVIII-deficiency and high titer inhibitor (BU=64), just before and 5 minutes after treatment with rhFVIIa at 90 μg/kg for acute joint bleeding. Patient treatment with rhFVIIa resulted in ~1.5-fold increase of ETP and peak height over baseline. Addition of increasing concentrations of $^{super}$FVa to patient plasma ex vivo resulted in additional ~3-fold increase of ETP and peak height in samples collected at baseline and after treatment with rhFVIIa (FIG. 5). ETP, but not peak height plateaued at 1.76 μg/mL $^{super}$FVa. Of note, values for ETPs and peak heights when this patient's plasma was spiked ex vivo with rhFVIIa at 2 μg/mL alone or in combination with $^{super}$FVa corresponded to values obtained after infusion of rhFVIIa (FIG. 4B). This corroborates that for in vitro experiments a concentration of 2 μg/mL FVIIa can be safely proposed as the therapeutic concentration post-infusion.

4. Effects of $^{super}$FVa on the Correction of ETP and Clotting Times in the Presence of rhAPC in Human and Murine Plasma To address the ability of $^{super}$FVa to reconstitute ETP that was maximally suppressed by human APC in murine or human plasma, plasma was spiked with $^{super}$FVa or FVa in the presence of APC. The optimal concentration of APC for maximal suppression of ETP in human and murine plasma was determined by dose-response to be 5 nM or 100 nM in human plasma or murine plasma, respectively (FIG. 14). Only $^{super}$FVa restored ETP to ~90-100% in human or murine plasma at concentrations where FVa did not show effects (FIG. 8). To address the ability of $^{super}$FVa to normalize APC-induced prolongation of clotting times, effects of $^{super}$FVa and FVa on aPTT shortening were studied in the presence of human APC. Prior to these experiments the optimal concentration of APC for aPTT prolongation to ~100 seconds had been determined to be 10 nM or 25 nM in human or murine plasma, respectively (FIG. 15). Both, $^{super}$FVa and FVa dose-dependently normalized the aPTT. However, in human plasma $^{super}$FVa normalized the aPTT at 100-fold lower concentrations compared to FVa (FIG. 9A). At 0.05 U/mL FVa variants, $^{super}$FVa fully corrected the aPTT, whereas FVa shortened the aPTT only from ~100 to 80 seconds (FIG. 9B). Similar findings were evident in murine plasma. At 5 U/mL FVa variants $^{super}$FVa fully corrected the aPTT, whereas FVa shortened the aPTT only from ~100 to 70 seconds (FIG. 9C).

5. Effects of $^{super}$FVA on the Correction of Clotting Times After Intravenous Administration of rmAPC to Balb/c Mice In an ex vivo whole blood aPTT assay, intravenous injection of rhAPC (0.5 mg/kg) compared to intravenous injection of saline into Balb/c mice doubled clotting times from mean 30 sec with saline to mean 67 sec with APC (saline n=31; rmAPC n=16; p<0.0001). Ex vivo addition of $^{super}$FVa to whole blood immediately drawn after APC injection normalized the aPTT to mean 30 sec (n=11; p=0.0005), whereas ex vivo addition of FVa failed to show a significant effect (mean aPTT 50; n=11; p=0.2). The effects of FVa variants seemed concentration dependent and differences in whole blood aPTT correction between $^{super}$FVa and FVa appeared most pronounced when FVa variants were employed at low concentration (0.05 U/mL; n=8). With increasing concentrations of the FVa variants differences became less evident (0.5 or 1 U/mL; n=3) (FIG. 10).

6. Efficient Prevention of Acute APC-Induced Bleeding after Tail Clip in Balb C Mice by $^{super}$FVA To determine the in vivo efficacy of $^{super}$FVa for bleed reduction in Balb/c mice treated with APC, blood loss was first determined in a conventional tail transection model. Blood was collected separately for the first 10 min and second 10-20 min after tail clip to distinguish initial bleeding from late rebleeding. The dose of APC that resulted in notable bleeding was determined by in vivo dose response to be 1.25 mg/kg. During the combined 20 minute bleeding period blood loss increased from mean 3.4 μL/kg with saline to mean 27 μL/kg with APC (p=0.007) (FIG. 11A). Protection with $^{super}$FVa 2 minutes prior to APC-injection decreased blood loss dose-dependently. At 5 U/mL a mild reduction of mean blood loss to 21 μL/kg was observed, whereas at 25 U/mL a significant reduction of mean blood loss to 9.2 μL/kg (p=0.04) was achieved (FIG. 11A).

Blood loss following APC was continuous and similar during the first and second 10 minutes after tail clip (mean 13.7 and 13.2 μL/kg, respectively). $^{super}$FVa reduced blood loss equally well during both time periods. The higher dose of $^{super}$FVa (25 U/mL) suppressed blood loss significantly to mean 4.3 μL/kg and 4.8 μL/kg during the first and second 10 minutes, respectively (all p-values ≤0.05) (FIG. 11B/C).

7. Feasibility of Liver Laceration in Mice as an Important Endpoint to Study Microvascular Parenchymal Organ Bleeding Liver laceration is frequently used as a bleeding model in larger animals such as rats, rabbits and swine (8-10) since it provides important information concerning microvessel-mediated parenchymal profuse bleeding after acute traumatic organ injury. In contrast, bleeding after tail clip more emulates bleeding patterns following complete transection of larger arterial and venous vessels. Bleeding patterns in both models may differ and may provide complementary information. However, in mice liver laceration is rarely performed and not universally established due to technical challenges pertaining to surgical intervention and abdominal blood collection in small animals. The inventors established a surgical approach, modified from Bajaj et al (11), whereby the liver is externalized after abdominal midline incision, and the left liver lobe lacerated with a 10 mm long scalpel cut, followed by blood collection with the mouse in prone position into saline (37°).

Feasibility and validation of the model were performed in hemophilia mice with established bleeding diathesis in the tail clip model by comparing results after tail clip with results after liver laceration. In both models, mean blood loss after 20 minutes was similar (liver laceration 40 μL/g; tail clip 35.7 μL/g). However, standard error of the mean (SEM), standard deviation (SD) and inter-individual range of blood loss were each ~4-fold reduced in the liver laceration model compared to the tail clip model (FIG. 12). SEM, SD, and range were decreased from 5 to 1.7, 20 to 4.9, and 61.1 to 14.6 μL/g, respectively. When treated with rhFVIII (50 U/kg), significant bleed reduction that was comparable to blood loss in wild type Balb/c mice was achieved in each model. Mean blood loss in FVIII-treated hemophilia mice and saline-treated wild type Balb/c mice was 25 μL/g and 29 μL/g (vs. 40 μL/g untreated hemophilia mice; p<0.0001) in the liver laceration model, and 9.7 μL/g and 4.2 μL/g in the tail clip model (vs. 35.7 μL/g untreated hemophilia mice; p=0.002), respectively. Low inter-individual differences in blood loss allowed to noticeably reduce the number of animals required to obtain statistical significance in the liver laceration model (liver laceration 26 mice; tail clip 39 mice) (FIG. 12). Given these results we determined that liver laceration in mice is a valid alternative method to study hemostasis in mice.

8. Efficient Treatment of Acute APC-Induced Bleeding After Liver Laceration in Balb C Mice by $^{super}$FVA To determine the in vivo efficacy of $^{super}$FVa for bleed reduction in wild-type Balb/c mice treated with APC in the liver laceration model, mice were injected intravenously either with $^{super}$FVa (25 U/mL) or saline, followed by intravenous APC (1.25 mg/kg). Dosing of APC and $^{super}$FVa was based on conditions yielding optimal results in the tail bleed model (FIG. 11). As after tail clip, mean blood loss during 20 minutes after liver laceration was significantly higher in mice injected with APC (40 µL/g) compared to mice injected with saline (29.5 µL/g; p=0.007), and treatment with $^{super}$FVa decreased mean blood loss significantly to baseline values (29 µL/g; p=0.02) (FIG. 13A). Mean blood loss during the first 10 minutes after liver laceration was pronounced following APC-injection (35.1 µL/g vs. saline 22.5 µL/g; p<0.0001) and significantly higher than after tail clip (35.1 µL/g vs 13.7 µL/g; p<0.0001). In contrast to the tail clip model, only little more bleeding was therefore observed during the second 10 minutes. The excessive bleeding induced by APC during the first 10 minutes was associated with a 54% mortality rate. Treatment with $^{super}$FVa not only corrected mean blood loss during the first 10 minutes from 35.1 µL/g to 23.2 µL/g (p=0.001), equivalent to blood loss observed at baseline in control wild type mice (22.5 µL/g), but also abolished bleeding-induced mortality (FIG. 11).

9. Rescue of APC-Induced Reduction of Thrombin Generation in Human Plasma.

The experiments in FIG. 16 show that rhFVIIa alone at increasing concentrations had no effects on thrombin generation, while $^{super}$FVa corrected thrombin generation to levels to those of normal human plasma. By contrast, adding trace amounts of rhFVIIa (100 ng/mL) to $^{super}$FVa increased thrombin generation by approximately 50% above normal human plasma.

These experiments provide convincing evidence that the combination of rhFVIIa with $^{super}$FVa synergistically increased thrombin generation suppressed by APC in human plasma. A dose finding study can be effected to determine lowest optimal concentration ranges of $^{super}$FVa in combination with rhFVIIa to correct thrombin generation to normal levels.

10. Clot Lysis Assay Results

Clot lysis assay was performed first to study the effect of anti-FVIII antibody on normal human plasma (FIG. 17). Titration of anti-FVIII antibody showed that more than 5 µg/ml antibody was sufficient to decrease the clot lysis time to the level of CPI control. 10 µg/ml antibody concentration was used further in studying the effect of rhFVIIa and $^{super}$FVa individually and in a synergistic manner on the clot lysis of normal human plasma with inhibitor against FVIII.

rhFVIIa and $^{super}$FVa individually showed an enhancement of clot lysis time in normal human plasma incubated with 10 µg/ml of anti-FVIII antibody at higher concentration of 2 µg/ml and ~2-5 µg/ml respectively (FIG. 18). However, when both of them were used together, clot lysis time was observed to enhance to the level of normal plasma at a decreased concentration of rhFVIIa by two orders of magnitude and in $^{super}$FVa by more than an order of magnitude (FIG. 19). The results clearly suggesting a synergistic effect of both rhFVIIa and $^{super}$FVa on correcting the clot lysis time of normal human plasma with inhibitors against FVIII. Plasma sample with CPI, inhibitor and highest concentration of either rhFVIIa or $^{super}$FVa in FIG. 18 was used as a negative control to show that the enhancement in clot lysis time is indeed due to either of these factors and not because of any other component of the coagulation cascade.

Moreover, in addition correcting the clot lysis time of normal human plasma with inhibitors against FVIII, alone and in combination, rhFVIIa and $^{super}$FVa have been shown to act synergistically to correct clot lysis time in FVIIIdP (FIG. 28).

11. Effects of $^{super}$FVA and FVIIA on Clot Lysis in FVIIIDP and NHP with FVIII-Inhibiting Antibodies.

Clot stability was studied as t-PA induced clot lysis time in NHP with anti-FVIII antibodies (GMA8015) at 10 µg/mL, as well as in FVIIIdP. The concentration of antibody was based on maximal shortening of the clot lysis time from approximately 105 min to 75 min following antibody titration (data not shown). The clot lysis time in the presence of antibody (10 µg/mL) was similar to the clot lysis time in the presence of CPI, which was used as control since it causes suppression of Thrombin Activatable Fibrinolysis Inhibitor (TAFI) activation. NHP and FVIIIdP were supplemented with rhFVIIa and $^{super}$FVa individually or combined. In NHP with anti-FVIII-antibody, increasing concentrations of rhFVIIa or $^{super}$FVa demonstrated increasing prolongation of clot lysis times (FIG. 5). Clot lysis times returned to normal at 40 nM rhFVIIa (therapeutic plasma concentration; FIG. 28A) or 3.33 nM $^{super}$FVa (FIG. 5B). The concentration of rhFVIIa to normalize clot lysis times could be lowered by 100-fold to ~0.4 nM in the presence of trace amounts of $^{super}$FVa (0.37 nM) (FIGS. 28A and 28B). Similar results were obtained when the experiments were performed in FVIIIdP (data not shown).

Example 16

The following materials and methods were used in this example.

Materials

Normal pooled human plasma (NHP) was purchased from George King Bio-Medical (Overland Park, Kans., USA). The following reagents were used: Rivaroxaban (Xarelto®, Bayer Healthcare, Leverkusen, Germany), Apixaban (Eliquis®, Bristol Meyers-Squibb, Princeton, N.J., USA), 4-Factor PCC (Kcentra™; CSL-Behring, King of Prussia, Pa., USA), recombinant human tissue factor (TF) (Dade Innovin®, Dade Behring; Newark, Del., USA), Corn trypsin inhibitor ((CTI) and thrombin (both from Enzyme Research Laboratories, South Bend, Ind., USA), thrombin calibrator (Diagnostica Stago, Parsippany, N.J., USA), Substrate Z-Gly-Gly-Arg-AMC (Bachem, Bubendorf, Switzerland), recombinant human FVIIa (NovoSeven®, NovoNordisk, Bagsvaerd, Denmark). Phospholipid vesicles (80% phosphatidylcholine (PC), 20% phosphatidylserine (PS)) were purchased from Avanti Lipids (Alabaster, Ala., USA) and prepared as described [18].

Protein Preparation

Recombinant $^{super}$FV (M. wt. 174 kDa) was made on a B-domain deleted S2183A FV platform and purified from conditioned media of stable transfected BHK cells by a combination of affinity chromatography using anti-FV 3B1 and HV5101 monoclonal antibodies as described [19]. $^{super}$FV protein concentration was determined by absorbance at 280 nm using FV ε1%=16.9 (calculated based on amino acid composition and MW of 174 kDa using DNASTAR (Lasergene, Madison, Wis.) and ELISA (Enzyme Research Laboratories, South Bend, Ind., USA) according to manufacturer's instructions. $^{super}$FV protein was activated with 2 nM thrombin for 20 minutes at 37° C. in prothrombinase buffer (50 Mm HEPES, 150 Mm NaCl, 0.5% BSA, 5 Mm CaCl2 and 0.1 Mm MnCl2). Activation was terminated by the addition of 1.1 molar equivalent of hirudin.

Thrombin Generation Assays

Thrombin generation or Endogenous Thrombin Potential (ETP) assays were performed as described [20]. Briefly, plasma samples supplemented with CTI, TF, PCPS were preincubated with the plasma at 37° C. vesicles in the presence or absence of rivaroxaban, apixaban, Kcentra®, NovoSeven® or $^{super}$FVa. Thrombin generation was initiated by addition of CaCl2 and Z-Gly-Gly-Arg-AMC in HBS/0.5% BSA. The final reaction mixture contained, 50% plasma, 0.725 μM CTI, 0.2 Pm TF, 4 μM PCPS vesicles, 0.5 mM Z-GGR-AMC, 7.6 mM CaCl2 in a total volume of 100 μl. Concentrations of rivaroxaban, apixaban, Kcentra®, NovoSeven® or $^{super}$FVa are indicated in the result section and in the figure legends. Fluorescence was measured at excitation/emission wavelengths of 360/460 nM using Gemini EM fluorescent plate reader (Molecular Devices). Fluorescence time course data were converted to Nm thrombin as described [21]. ETP, defined as the area under the curve (AUC) and the peak height were determined using Origin software.

Results

Effects of $^{super}$FVa and FVIIa on thrombin generation in NHP in the presence of the NOACs rivaroxaban and apixaban.

Figure 20:
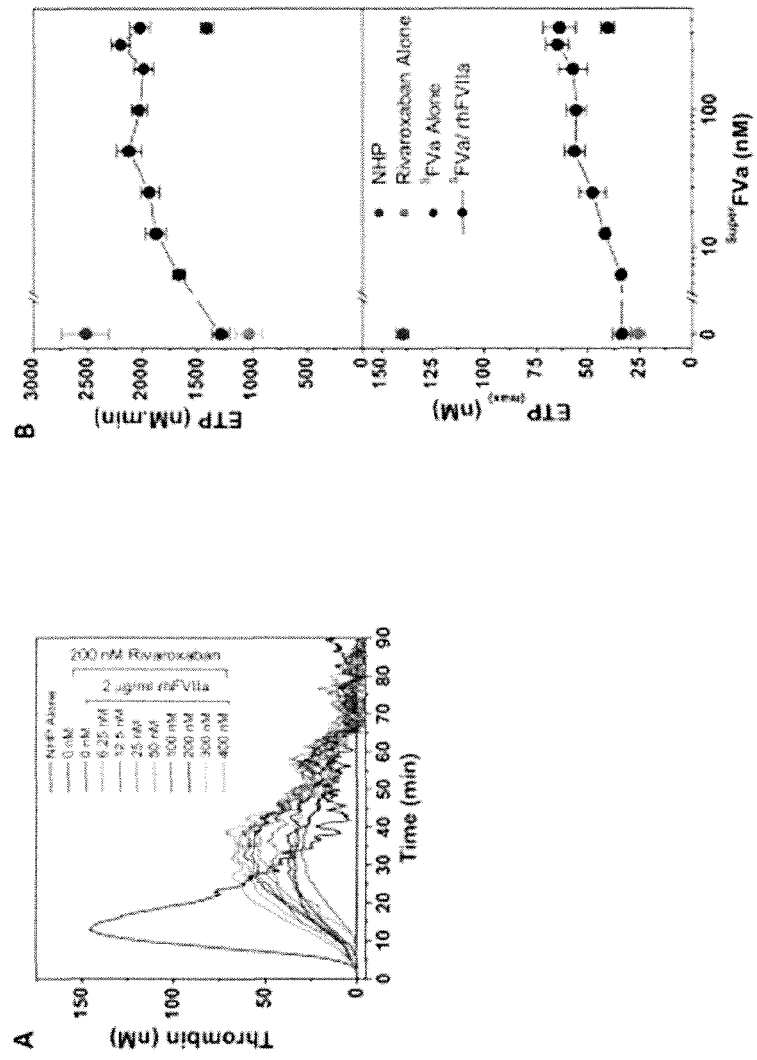
Figure 21:
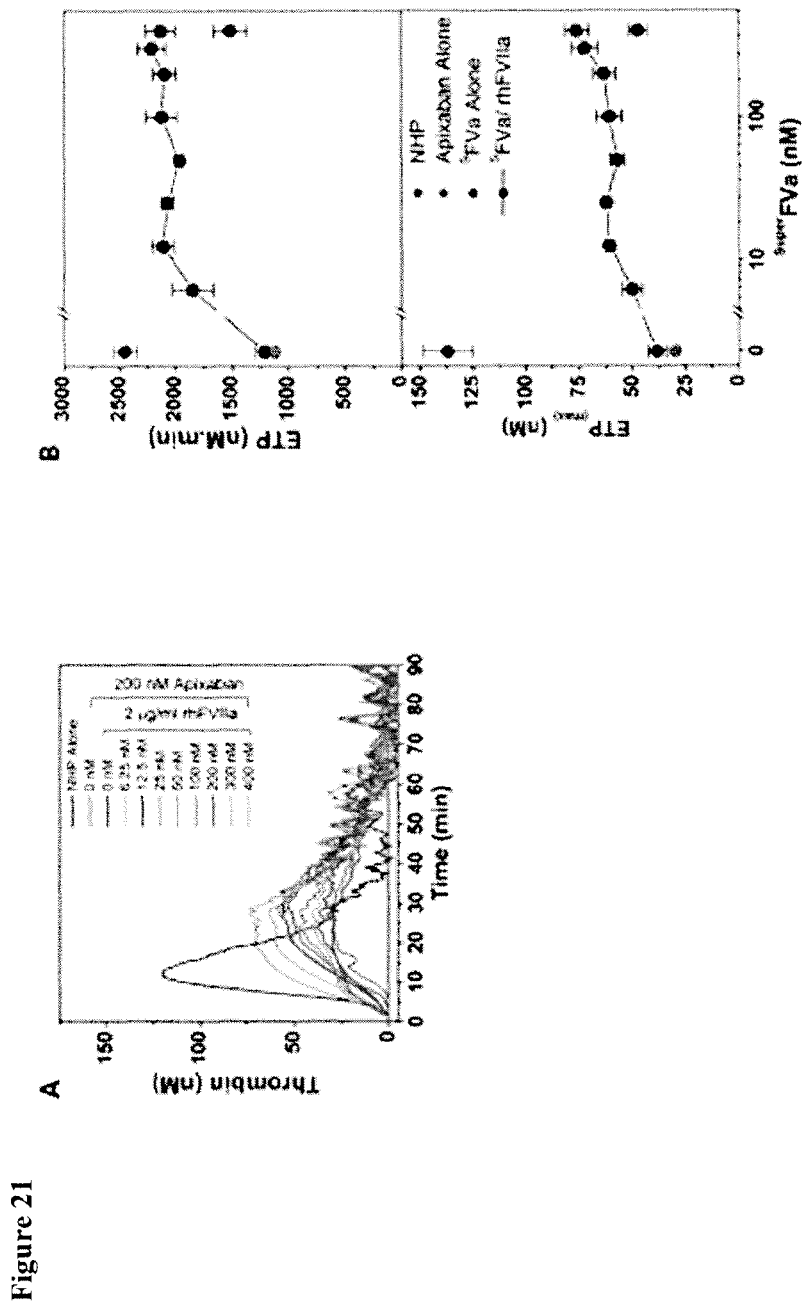

When rivaroxaban or apixaban were added to NHP, optimal suppression of ETP was reached at a concentration of 200 nM following dose titration for both agents (FIGS. 20 and 21). This concentration approximates peak plasma concentrations achieved in humans after oral administration [22, 23]. Neither rhFVIIa at 2 μg/ml, which corresponds to the expected peak plasma concentration following intravenous administration in humans at the maximum approved dose for hemophilia patients with inhibitors (90 μg/kg), nor $^{super}$FVa at high concentration (400 nM) were able to enhance the ETP of NHP suppressed with either rivaroxaban or apixaban (200 nM) (FIGS. 20 and 21). However, combination of rhFVIIa (2 μg/mL) with increasing concentrations of $^{super}$FVa (6.25 to 400 nM) in the presence of rivaroxaban or apixaban enhanced ETP ~2 fold and peak height ~1.5 fold over baseline. A maximum plateau effect was reached at a concentration of 25-50 nM $^{super}$FVa, with no further increases in ETP or peak height with higher concentrations of $^{super}$FVa. (FIGS. 20 and 21).

Effects of $^{super}$FVa and Kcentra™ on thrombin generation in NHP in the presence of the NOACs rivaroxaban and apixaban.

Figure 22:
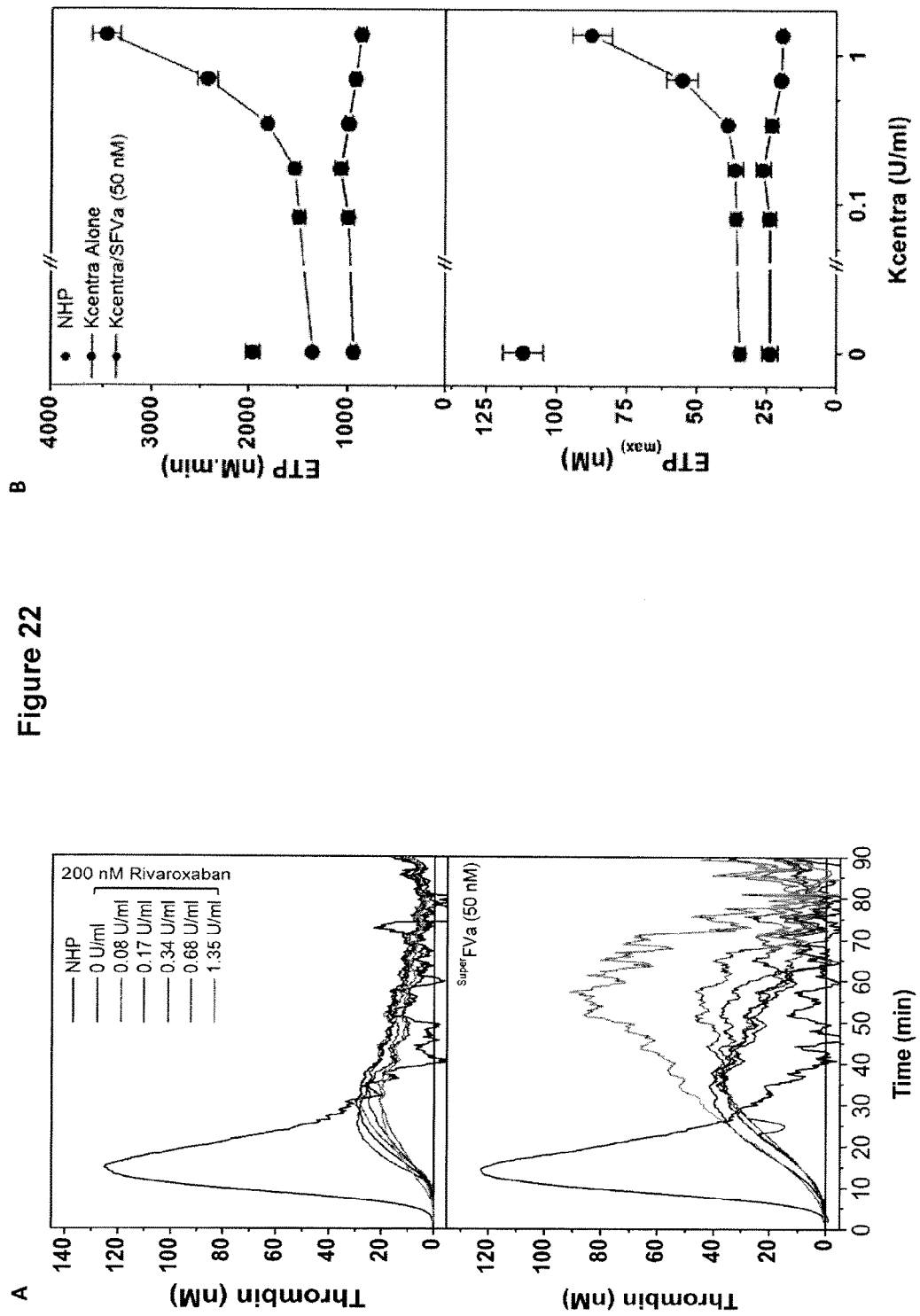
Figure 23:
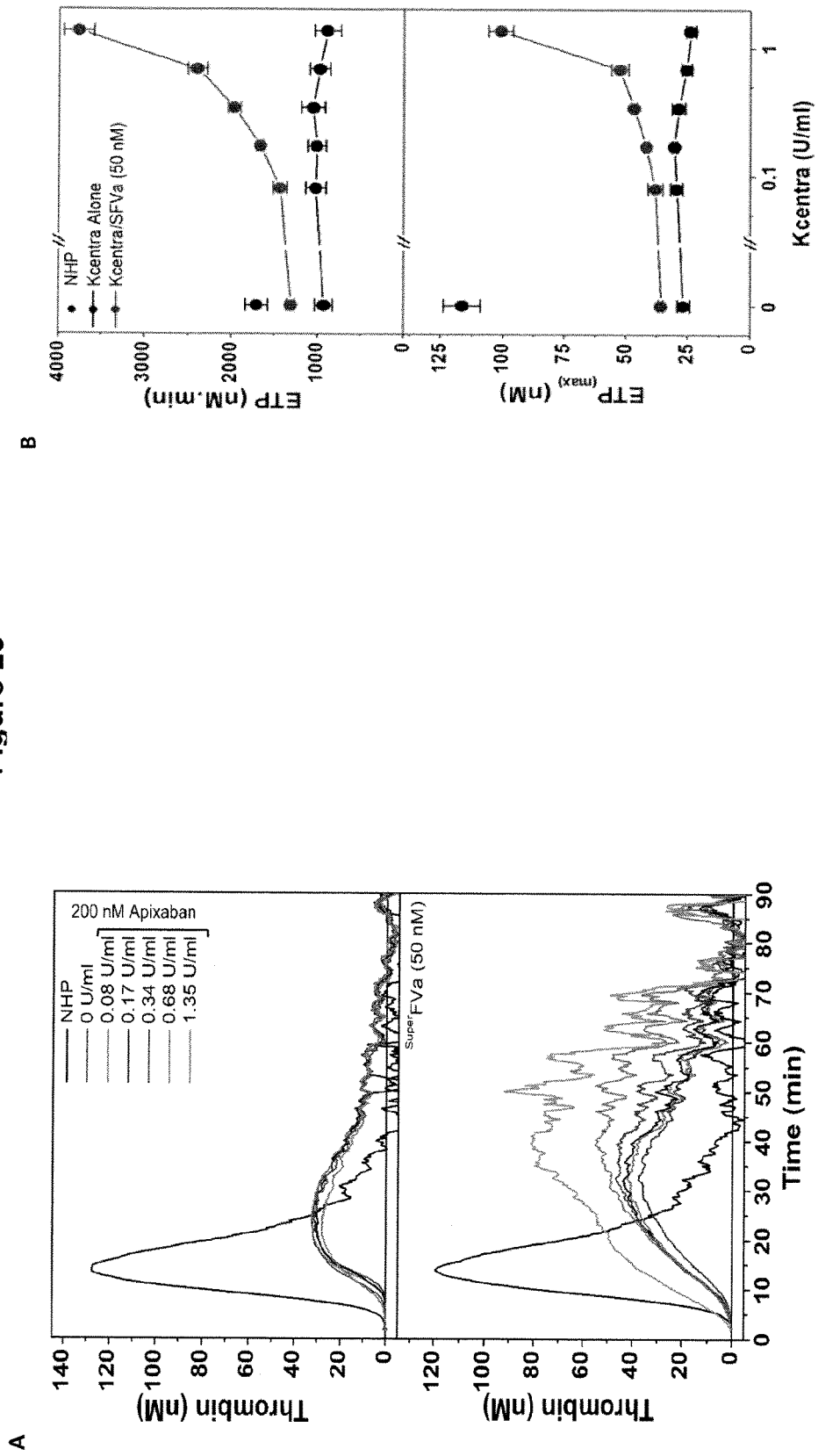
Figure 24:
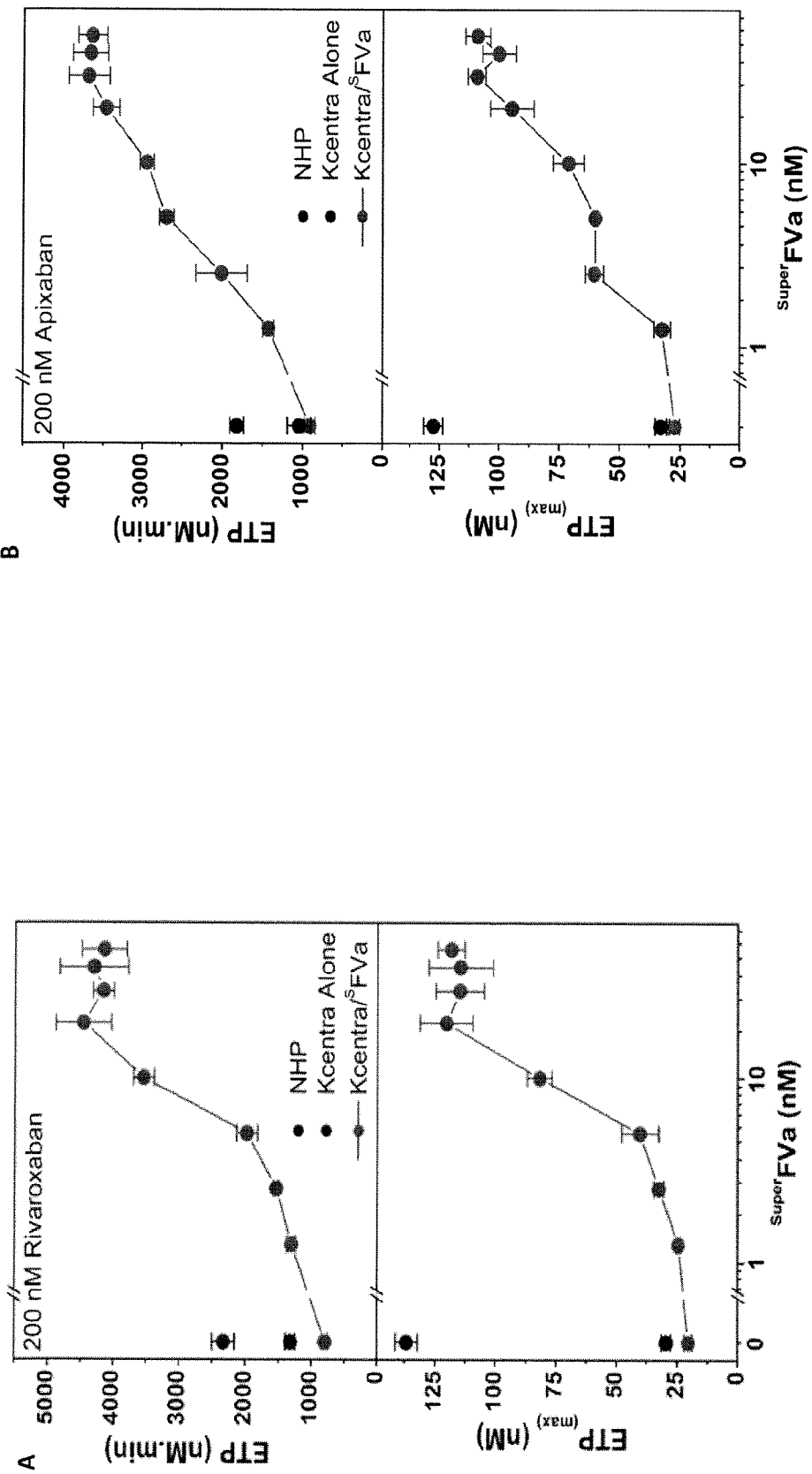

The 4-Factor PCC Kcentra™ is approved and effective for reversal of warfarin-induced bleeding [9] and is also often used off-label for NOAC-induced bleeding absent clinical evidence of effectiveness. We therefore studied the effect of Kcentra™ alone and in combination with $^{super}$FVa using thrombin generation assays in NHP in the presence of either rivaroxaban or apixaban. When Kcentra™ was added to NHP at a concentration which approximates the expected plasma concentration (1.35 U/Ml) after intravenous infusion of the highest recommended dose (50 U/kg), Kcentra™ alone was not able to increase thrombin generation suppressed by either rivaroxaban or apixaban (20 nM) (FIGS. 22 and 23). However, synergistic effects on ETP and peak height were observed when Kcentra™ was combined with $^{super}$FVa. At a fixed concentration of $^{super}$FVa (50 Nm) increasing concentrations of Kcentra™ (0.08 to 1.35 U/Ml) in the presence of rivaroxaban or apixaban (200 nM) increased the ETP up to ~4-fold and the peak height up to ~2-fold over baseline (FIGS. 22 and 23). Similarly, at a fixed concentration of Kcentra™ (1.35 U/ml) the titration of $^{super}$FVa (1.25 to 400 Nm) into NHP enhanced both, ETP and peak height, up to ~4-fold over baseline in the presence of rivaroxaban or apixaban (200 nM) (FIG. 24).

Example 17

The following materials and methods were used in this example.

Animals.

All described animal protocols were carried out as approved by the institutional animal and care committee of The Scripps Research Institute. Several breeding pairs of FVIII-deficient mice (Balb/c background) were a generous gift of Dr. David Lillicrap. Mice of both genders, aged ≥8 weeks were used for tail bleeding assays.

Bleeding Assays in FVIII-Deficient Mice.

Mice were anesthetized, placed on temperature controlled heating pads (37° C.), and the distal portion of the tail was cut at 1.5 mm diameter after which the tail was immersed in a predefined volume of 37° C. saline (0.9% NaCl) for 20 minutes. Blood loss was determined by the hemoglobin concentration in the saline solution after red cell lysis with 2% acetic acid and measured by absorbance at 405 nm. Using a hemoglobin standard derived from defined blood volumes, blood loss was calculated assuming a hematocrit of 46% and expressed in μL/g body weight. Groups of FVIII-deficient mice were injected intravenously (retro-orbital) within 2 minutes prior to tail cut with equal volumes (200 μM) of sterile saline for injection (0.9%, Hospira Inc.), rhFVIII 200 units/kg FVIII (Xyntha®, Pfizer, NY, N.Y., USA) $^{super}$FVa, rhFVIIa (NovoSeven®, NovoNordisk, Bagsvaerd, Denmark) or a combination of $^{super}$FVa and rhFVIIa. All agents were diluted in sterile sodium chloride 0.9% for injection (Hospira Inc). As with FVIII, FVa variant dosing was based on prothrombinase cofactor activity, whereby the activity of 20 nM wild-type FVa (approximate FV plasma concentration) was defined as one Unit.

Statistical Analysis.

Student's t-test, or for bleeding Kruskal-Wallis followed by two-tailed Mann-Whitney test, was used to assess statistical significance where appropriate. A p-value of ≤0.05 was considered statistically significant.

Results

Efficient treatment of acute tail bleeding in FVIII-deficient mice by combining $^{super}$FVa and rhFVIIa.

To determine the in vivo efficacy of $^{super}$FVa alone and in combination with rhFVIIa for bleed reduction in hemophilia, blood loss during a 20 minute bleeding period was determined in a tail transection model in FVIII-deficient mice. $^{super}$FVa significantly reduced blood loss in a dose dependent fashion. Mean blood loss in mice injected with the lowest dose of $^{super}$FVa (10 U/kg) was similar to saline (25.9 μL/g vs. 26.3 μL/g), but improved significantly with injection of higher doses. Mean blood loss was reduced to 9.7 and 2.5 μL/g at 40 and 200 U/kg $^{super}$FVa (p=0.005). Blood loss reduction achieved with the highest dose of $^{super}$FVa (200 u/kg) was indistinguishable from rhFVIII (2.9 μL/g). As reported previously, bleed reduction with rhFVIIa in FVIII-deficient mice can only be achieved at 10 to 100-fold higher doses than used in hemophilic patients (21). Compared to saline (25.9 μL/g) mean blood loss after injection of 1 mg/kg rhFVIIa (~10-fold higher dose than in human) and 3 mg/kg rhFVIIa was reduced to 16.8 μL/g (p=0.1) and 7.2 μL/g (p=0.003), which remained significantly different from rhFVIII (2.9 μL/g, p=0.03). When rhFVIIa at low dose (1 mg/kg) was combined with $^{super}$FVa at the concentration of 10 U/kg, which had previously not demonstrated a decrease in bleeding, a significant reduction of mean blood loss from 16.7 µL/g to 10.2 µL/g was noted (p=0.05). When rhFVIIa at 3 mg/kg was combined with a medium dose of $^{super}$FVa (40 U/kg) bleeding was abrogated similar to what was observed with rhFVIII. Mean blood loss decreased from 7.2 µL/g with rhFVIIa alone to 1.6 µL/g (p=0.01) when both molecules were combined. In combination, these results suggest synergistic effects of rhFVIIa and $^{super}$FVa on bleed reduction in FVIII-deficient mice (FIG. 25A-C).

Efficient treatment of acute tail bleeding in FVIII-deficient mice by combining $^{super}$FVa and rhFVIIa.

Figure 29:
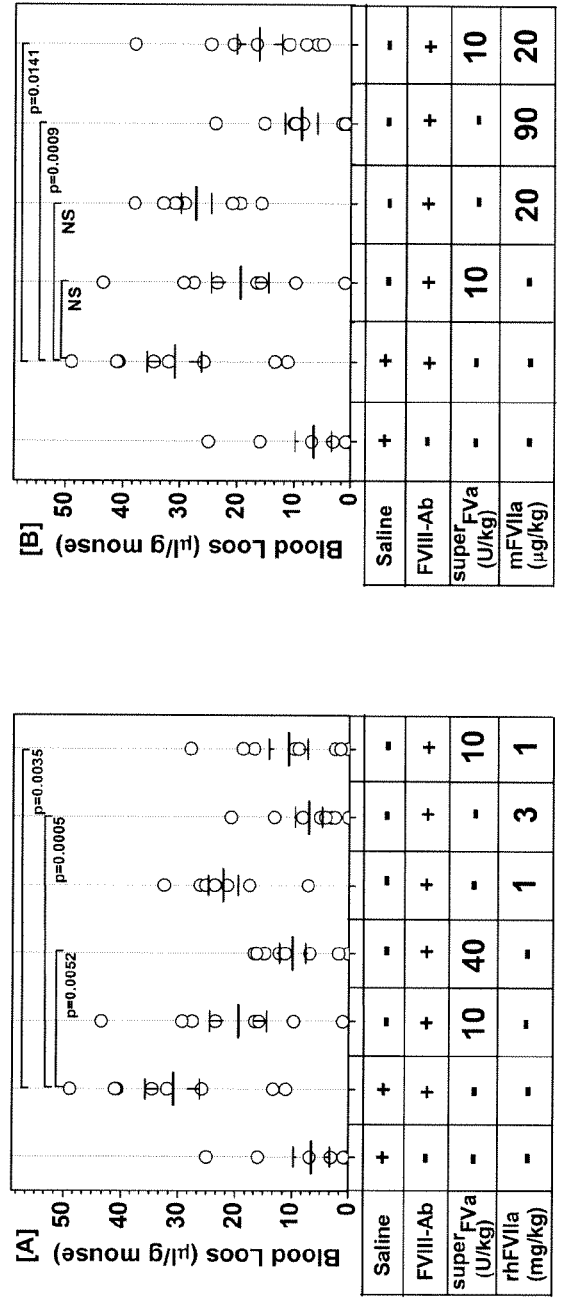

To further elucidate the efficiency of $^{super}$FVa to reduce bleeding in presence of inhibitors for FVIII either alone or in combination with rhFVIIa, blood loss during a 20 minute bleeding period was determined in a tail transection model in Balb/c mice treated with anti-FVIII antibodies (0.25 mg/kg). The Bethesda Unit of the antibodies in mice was estimated to be 35±2 BU/ml. Significant dose dependent reduction of bleeding was observed with $^{super}$FVa which matched with our previous study in FVIII-deficient mice model. While a low dose of $^{super}$FVa (10 U/kg) did not show a significant bleed reduction than control saline injected mice (19.47 µL/g vs. 30.9 µL/g respectively), a high dose of $^{super}$FVa (40 U/kg) significantly reduced the bleeding (9.97 µL/g, p=0.005) as compared to the saline. Similarly, low dose of rhFVIIa (1 mg/kg) was not able to significantly reduce the bleeding (22.18 µL/g) but a high dose of 3 mg/kg rhFVIIa significantly decreased the bleeding (7.13 µL/g. p=0.0005). Combination of low doses of $^{super}$FVa (10 U/kg) and rhFVIIa (1 mg/kg) together synergistically reduced the bleeding in a significant manner to 10.77 µL/g, p=0.003 (FIG. 29). We further used mFVIIa purified in our lab to test the effect in bleed reduction of Balb/c mice treated with anti-FVIII antibodies. At low concentration of mFVIIa (20 µg/kg), bleed reduction was not significantly (27.2 µl/g) different than the saline injected mice. However, at 90 µg/kg (dosage similar to therapeutic dose of rhFVIIa in humans) significant bleed reduction was observed (8.77 µl/g, p=0.0009). When we combined the low dose of $^{super}$FVa (10 U/kg) and mFVIIa (20 µg/kg) blood loss was significantly reduced to 16.15 µl/g (p=0.0141) as compared to the saline injected mice (FIG. 29A/B).

The study was also helpful in directly comparing the dosage required to reduce bleeding by rhFVIIa and mFVIIa in Balb/c mice treated with anti-FVIII antibodies (FIG. 30), which provided the proof of concept of a synergistic association of $^{super}$FVa and rhFVIIa in treating the bleeding complication in patients with inhibitors against FVIII.

CONCLUSIONS

Increased risk of bleeding is observed in patients receiving therapy with a variety of anticoagulant drugs, and there is an unmet need for prohemostatic agents that reduce bleeding risk. In some clinical trials, wild type (wt) APC therapy was associated with an increased risk of serious bleeding. In most animal models of inflammatory injury and disease where APC was beneficial, APC's cytoprotective effects were responsible for the protective effects of APC therapy whereas its anticoagulant effects were neither required nor contributing. Thus, wt APC's anticoagulant activities and associated risk of bleeding may be a limiting factor for potential novel wt-APC therapies. The availability of a wt APC-anticoagulant specific antidote or reversal agent that does not affect wt APC's cytoprotective activities would be highly desirable.

We hypothesized that $^{super}$FVa, an engineered FVa-variant that potently normalizes hemostasis in hemophilia, fits the criteria for a prohemostatic biologic that could reduce wt APC-induced bleeding, and here we test this hypothesis. $^{super}$FVa has enhanced specific activity compared to wt FVa due to an engineered disulfide bond (Cys609-Cys1691) between the A2 and A3 domains (FV (A2-SS-A3)) and, its biological activity is augmented by mutations of the APC cleavage sites (Arg506/306/679Gln) and by a mutation that alters glycosylation (Ser2183Ala). As a result of these modifications, $^{super}$FVa was found to be resistant to wt APC and normalized hemostatic properties and prevented bleeding in a hemophilic mouse model much more efficiently than wt FVa.

In aPTT clotting assays both $^{super}$FVa and wt FVa dose-dependently normalized clotting times when wt-APC was used to prolong clotting (aPTT >100 sec). However, $^{super}$FVa normalized the aPTT at 100-fold lower concentrations compared to wt FVa. In thrombin generation assays using either human or murine plasma, $^{super}$FVa fully restored thrombin generation at concentrations where wt FVa did not show effects.

In an ex vivo whole blood aPTT assay, intravenous (iv) injection of murine recombinant wt APC (0.5 mg/kg) in Balb/c mice doubled clotting times from 30 sec to ~60 sec (n=40). Addition of $^{super}$FVa (1 nM) to whole blood significantly normalized aPTT clotting times whereas wt FVa failed to show a significant effect.

In a tail clip-bleeding model in Balb/c mice, injection (iv) of human recombinant or plasma-derived wt APC induced significant bleeding at 1.25 mg/kg and mean blood loss increased from 3.4 µL/g with saline to 27 µL/g with wt APC treatment. $^{super}$FVa injected (iv 3.5 mg/kg) 2 min prior to wt APC administration reduced bleeding significantly to 9.2 µL/g (n~10 per group).

In another bleeding model, liver laceration was used because it provides important information concerning microvessel-mediated bleeding after acute organ injury. After adaptation and technical modifications of the model used in rats and rabbits for mouse anatomy and validation in hemophilia versus control mice, this model provided a reliable assessment of bleeding with a ~4-fold reduced inter-individual range of blood loss compared to the tail clip-bleeding model. Injection (iv) of human wt APC increased blood loss from 29 µL/g to 49 µL/g, and the excessive bleeding was associated with a ~40% mortality rate. $^{super}$FVa reduced wt APC-induced bleeding after 20 min significantly to 29 µL/g and abolished bleeding-induced mortality.

Remarkably, bleeding patterns in the tail clip and liver laceration models were different when blood loss was determined separately for the $1^{st}$ and $2^{nd}$ 10 min after injury. In the tail clip-model wt-APC-induced bleeding during both $1^{st}$ and $2^{nd}$ 10 min after tail clip and $^{super}$FVa decreased blood loss during both phases. In the liver laceration model, most blood loss occurred immediately after injury and bleeding during the $2^{nd}$ 10 min was less pronounced. In this model, however, $^{super}$FVa corrected blood loss entirely during the $1^{st}$ 10 min phase and fully prevented bleeding during the $2^{nd}$ 10 min phase.

Therefore, our results demonstrate that FVa, and in particular $^{super}$FVa may be used to inhibit or prevent APC-associated bleeding. With respect thereto, severe hemorrhage is a frequent complication of anti-coagulant therapy in general (32), has been reported with APC-therapy (21) and may complicate clinical development of wild-type APC for important indications such as mitigation of radiation injury (33). Here, we demonstrate that $^{super}$FVa, an engineered FVa variant, is an efficient prohemostatic reversal agent for bleeding induced by wild type APC.

As described herein, in order to study the effects of $^{super}$FVa as a bleed reversal agent for APC-induced bleeding, the inventors established the optimal dose of APC to elicit bleeding in the mouse after a single intravenous administration by dose-response to be 1.25 mg/kg. Given the necessity to overcome as best as possible the inter-individual bleed variation after tail clip the optimal APC dosing was established in the tail clip model, and subsequently applied to liver laceration. In both bleeding models $^{super}$FVa reduced blood loss significantly in mice treated with APC. The massive blood loss within the 1$^{st}$ 10 minutes was associated with a ~50% mortality rate. Notably, $^{super}$FVa not only provided significant bleed protection similar to blood loss in mice without APC treatment, but also abolished bleeding-induced mortality.

The mechanism by which $^{super}$FVa prevents APC-induced bleeding is consistent with FVa activity augmentation within the prothrombinase complex. It is well described that the presence of FVa in the prothrombinase complex potently enhances the rate of thrombin generation to approximately 10,000-fold (36, 37). However, FVa is also rapidly inactivated by APC via proteolytic cleavage at Arg506 followed by a slower cleavage at Arg306. Mutations of these inactivation cleavage sites, such as Arg506Gln (a.k.a. $FV_{Leiden}$), extend the FVa cofactor activity half-life. In vivo relevance that FVa and especially mutations which render FVa APC-inactivation resistant can mitigate clinical bleeding is derived from studies in hemophilic patients and mice. The $FV_{Leiden}$ mutation is now accepted to be a disease modifier in persons with hemophilia and hemophilic mice (34, 38). Moreover, the pharmacological administration of FVa to hemophilic mice was demonstrated to improve coagulation profiles (34) as well as bleeding and blood loss was much more efficiently abrogated by $^{super}$FVa.

Therefore, we have demonstrated that $^{super}$FVa is effective in the prevention and reversal of wild type APC-induced bleeding, which is of major concern for intervention in acute traumatic coagulopathy, in severe sepsis and treatment of other conditions which may result in increased APC such as acute radiation injury (33). Our findings suggest utility of $^{super}$FVa as a prohemostatic agent due to cofactor activity in the prothrombinase complex, which constitutes the last step in the process of thrombin generation. FVa activity augmentation by $^{super}$FVa is relevant in treating serious bleeding such as severe traumatic bleeding or bleeding with novel anti-coagulants where a paucity of therapeutic options exist with an unmet clinical need for life saving hemostatic measures.

Accordingly, in summary our results provide convincing evidence that $^{super}$FVa is effective as a monotherapy or in combination with other procoagulants in the prevention and reversal of wt APC-induced bleeding. In addition to improving hemostasis in hemophilia, $^{super}$FVa protects against bleeding in 2 different mouse models where bleeding was induced by wt APC. Hence, $^{super}$FVa should be used as a prohemostatic agent in situations where bleeding is a serious risk.

The following references are cited in this patent application. The contents of each of these references are incorporated by reference in their entirety herein.

REFERENCES

1. Darby S C, Kan S W, Spooner R J, Giangrande P L, Hill F G, Hay C R, Lee C A, Ludlam C A, and Williams M. Mortality rates, life expectancy, and causes of death in people with hemophilia A or B in the United Kingdom who were not infected with HIV. *Blood.* 2007; 110(3): 815-25.
2. Gouw S C, van der Bom J G, Ljung R, Escuriola C, Cid A R, Claeyssens-Donadel S, van Geet C, Kenet G, Mikipernaa A, Molinari A C, et al. Factor VIII products and inhibitor development in severe hemophilia A. *N Engl J Med.* 2013; 368(3):231-9.
3. Hay C R, DiMichele D M, and Study IIT. The principal results of the International Immune Tolerance Study: a randomized dose comparison. *Blood.* 2012; 119(6):1335-44.
4. Hoots W K. Arthropathy in inhibitor patients: differences in the joint status. *Semin Hematol.* 2008; 45(2 Suppl 1):S42-9.
5. Hoffman M, Monroe D M, and Roberts H R. Activated factor VII activates factors IX and X on the surface of activated platelets: thoughts on the mechanism of action of high-dose activated factor VII. *Blood coagulation & fibrinolysis: an international journal in haemostasis and thrombosis.* 1998; 9 Suppl 1(S61-5.
6. van't Veer C, and Mann K G. The regulation of the factor VII-dependent coagulation pathway: rationale for the effectiveness of recombinant factor VIIa in refractory bleeding disorders. *Seminars in thrombosis and hemostasis.* 2000; 26(4):367-72.
7. Astermark J, Donfield S M, DiMichele D M, Gringeri A, Gilbert S A, Waters J, Berntorp E, and Group F S. A randomized comparison of bypassing agents in hemophilia complicated by an inhibitor: the FEIBA NovoSeven Comparative (FENOC) Study. *Blood.* 2007; 109(2):546-51.
8. Astermark J, Santagostino E, and Keith Hoots W. Clinical issues in inhibitors. *Haemophilia.* 2010; 16 Suppl 5(54-60.
9. de Paula E V, Kavakli K, Mahlangu J, Ayob Y, Lentz S R, Morfini M, Nemes L, Sǎlek SZ, Shima M, Windyga J, et al. Recombinant factor VIIa analog (vatreptacog alfa [activated]) for treatment of joint bleeds in hemophilia patients with inhibitors: a randomized controlled trial. *Journal of thrombosis and haemostasis. JTH* 2012; 10(1): 81-9.
10. Møss J, Scharling B, Ezban M, and Møller Sorensen T. Evaluation of the safety and pharmacokinetics of a fast-acting recombinant FVIIa analogue, NN1731, in healthy male subjects. *Journal of thrombosis and haemostasis: JTH.* 2009; 7(2):299-305.
11. Spira J, Plyushch O, Zozulya N, Yatuv R, Dayan I, Bleicher A, Robinson M, and Baru M. Safety, pharmacokinetics and efficacy of factor VIIa formulated with PEGylated liposomes in haemophilia A patients with inhibitors to factor VIII—an open label, exploratory, cross-over, phase I/II study. *Haemophilia.* 2010; 16(6): 910-8.
12. Milanov P, Ivanciu L, Abriss D, Quade-Lyssy P, Miesbach W, Alesci S, Tonn T, Grez M, Seifried E, and Schüttrumpf J. Engineered factor IX variants bypass FVIII and correct hemophilia A phenotype in mice. *Blood.* 2012; 119(2):602-11.
13. Ivanciu L, Toso R, Margaritis P, Pavani G, Kim H, Schlachterman A, Liu J H, Clerin V, Pittman D D, Rose-Miranda R, et al. A zymogen-like factor Xa variant corrects the coagulation defect in hemophilia. *Nat Biotechnol.* 2011; 29(11):1028-33.
14. Toso R, Zhu H, and Camire R M. The conformational switch from the factor X zymogen to protease state mediates exosite expression and prothrombinase assembly. *J Biol Chem.* 2008; 283(27):18627-35.
15. Mann K G, Jenny R J, and Krishnaswamy S. Cofactor proteins in the assembly and expression of blood clotting enzyme complexes. *Annual review of biochemistry.* 1988; 57(915-56.
16. Gale A J, Xu X, Pellequer J L, Getzoff E D, and Griffin J H. Interdomain engineered disulfide bond permitting elucidation of mechanisms of inactivation of coagulation factor Va by activated protein C. *Protein Sci.* 2002; 11(9):2091-101.
17. Lusher J M K C, Green D. *Acquired Hemophilia.* Princeton: Excerpta Medica, Inc.; 1995.
18. Mesters R M, Houghten R A, and Griffin J H. Identification of a sequence of human activated protein C (residues 390-404) essential for its anticoagulant activity. *The Journal of biological chemistry.* 1991; 266(36):24514-9.
19. Radtke K P, Griffin J H, Riceberg J, and Gale A J. Disulfide bond-stabilized factor VIII has prolonged factor VIIIa activity and improved potency in whole blood clotting assays. *Journal of thrombosis and haemostasis: JTH.* 2007; 5(1): 102-8.
20. Hemker H C, Giesen P, AlDieri R, Regnault V, de Smed E, Wagenvoord R, Lecompte T, and Beguin S. The calibrated automated thrombogram (CAT): a universal routine test for hyper- and hypocoagulability. *Pathophysiology of haemostasis and thrombosis.* 2002; 32(5-6):249-53.
21. Bernard G R, Vincent J L, Laterre P F, LaRosa S P, Dhainaut J F, Lopez-Rodriguez A, et al. Efficacy and safety of recombinant human activated protein C for severe sepsis. N Engl J Med. 2001 March; 344(10):699-709.
22. Kerschen E J, Fernandez J A, Cooley B C, Yang X V, Sood R, Mosnier L O, et al. Endotoxemia and sepsis mortality reduction by non-anticoagulant activated protein C. J Exp Med. 2007 October; 204(10):2439-48.
23. Mosnier L O, Yang X V, Griffin J H. Activated protein C mutant with minimal anticoagulant activity, normal cytoprotective activity, and preservation of thrombin activable fibrinolysis inhibitor-dependent cytoprotective functions. J Biol Chem. 2007 November; 282(45):33022-33.
24. Gale A J, Xu X, Pellequer J L, Getzoff E D, Griffin J H. Interdomain engineered disulfide bond permitting elucidation of mechanisms of inactivation of coagulation factor Va by activated protein C. Protein Sci. 2002 September; 11(9):2091-101.
25. Burnier L, Fernández J A, Griffin J H. Antibody SPC-54 provides acute in vivo blockage of the murine protein C system. Blood Cells Mol Dis. 2013 April; 50(4):252-8.
26. MESTERS R, HOUGHTEN R, GRIFFIN J. IDENTIFICATION OF A SEQUENCE OF HUMAN ACTIVATED PROTEIN-C(RESIDUES 390-404) ESSENTIAL FOR ITS ANTICOAGULANT ACTIVITY. Journal of Biological Chemistry. 1991 Dec. 25 1991; 266(36): 24514-9.
27. Hemker H, Giesen P, AlDieri R, Regnault V, de Smed E, Wagenvoord R, et al. The Calibrated Automated Thrombogram (CAT): A universal routine test for hyper- and hypocoagulability. Pathophysiology of Haemostasis and Thrombosis. 2002 September-December 2002; 32(5-6): 249-53.
28. Lu G, DeGuzman F, Hollenbach S, Karbarz M, Abe K, Lee G, et al. A specific antidote for reversal of anticoagulation by direct and indirect inhibitors of coagulation factor Xa. Nature Medicine. 2013 April 2013; 19(4): 446-+.
29. Karakaya K, Ucan H, Tascilar O, Emre A, Cakmak G, Irkorucu O, et al. Evaluation of a New Hemostatic Agent Ankaferd Blood Stopper in Experimental Liver Laceration. Journal of Investigative Surgery. 2009 2009; 22(3): 201-6.
30. Charbonneau S, Lemarie C, Peng H, Ganopolsky J, Shek P, Blostein M. Surface-attached amphipathic peptides reduce hemorrhage in vivo. Journal of Trauma and Acute Care Surgery. 2012 January. 2012; 72(1):136-42.
31. Bajaj M, Ogueli G, Kumar Y, Vadivel K, Lawson G, Shanker S, et al. Engineering Kunitz Domain 1 (KDI) of Human Tissue Factor Pathway Inhibitor-2 to Selectively Inhibit Fibrinolysis PROPERTIES OF KD1-L17R VARIANT. Journal of Biological Chemistry. 2011 February 2011; 286(6):4329-40.
32. Jasuja G K, Reisman J I, Miller D R, Berlowitz D R, Hylek E M, Ash A S, et al. Identifying major hemorrhage with automated data: results of the Veterans Affairs study to improve anticoagulation (VARIA). Thrombosis research. 2013 January; 131(1):31-6.
33. Geiger H, Pawar S A, Kerschen E J, Nattamai K J, Hernandez I, Liang H P, et al. Pharmacological targeting of the thrombomodulin-activated protein C pathway mitigates radiation toxicity. Nat Med. 2012 July; 18(7):1123-9.
34. Schlachterman A, Schuettrumpf J, Liu J H, Furlan Freguia C, Toso R, Poncz M, et al. Factor V Leiden improves in vivo hemostasis in murine hemophilia models. Journal of thrombosis and haemostasis: JTH. 2005 December; 3(12):2730-7.
35. Mei B, Pan C, Jiang H, Tjandra H, Strauss J, Chen Y, et al. Rational design of a fully active, long-acting PEGylated factor VIII for hemophilia A treatment. Blood. 2010 Jul. 15; 116(2):270-9.
36. Mann K G, Jenny R J, Krishnaswamy S. Cofactor proteins in the assembly and expression of blood clotting enzyme complexes. Annual review of biochemistry. 1988; 57:915-56.
37. Nesheim M E. A simple rate law that describes the kinetics of the heparin-catalyzed reaction between antithrombin III and thrombin. J Biol Chem. 1983 Dec. 10; 258(23):14708-17.
38. Franchini M, Lippi G. Factor V Leiden and hemophilia. Thrombosis research. 2010 February; 125(2):119-23.

REFERENCES CITED IN EXAMPLES 16 AND 17

1 Majeed A, Schulman S: Bleeding and antidotes in new oral anticoagulants. Best Pract Res Clin Haematol 2013; 26:191-202.
2 Siegal D M, Cuker A: Reversal of novel oral anticoagulants in patients with major bleeding. J Thromb Thrombolysis 2013; 35:391-398.
3 Connolly S J, Ezekowitz M D, Yusuf S, Eikelboom J, Oldgren J, Parekh A, Pogue J, Reilly P A, Themeles E, Varrone J, Wang S, Alings M, Xavier D, Zhu J, Diaz R, Lewis B S, Darius H, Diener H C, Joyner C D, Wallentin L, Investigators R-LSCa: Dabigatran versus warfarin in patients with atrial fibrillation. N Engl J Med 2009; 361:1139-1151.
4 Patel M R, Mahaffey K W, Garg J, Pan G, Singer D E, Hacke W, Breithardt G, Halperin J L, Hankey G J, Piccini J P, Becker R C, Nessel C C, Paolini J F, Berkowitz S D, Fox K A, Califf R M, Investigators RA: Rivaroxaban versus warfarin in nonvalvular atrial fibrillation. N Engl J Med 2011; 365:883-891.
5 Granger C B, Alexander J H, McMurray J J, Lopes R D, Hylek E M, Hanna M, Al-Khalidi H R, Ansell J, Atar D, Avezum A, Bahit M C, Diaz R, Easton J D, Ezekowitz J A, Flaker G, Garcia D, Geraldes M, Gersh B J, Golitsyn S, Goto S, Hermosillo A G, Hohnloser S H, Horowitz J, Mohan P, Jansky P, Lewis B S, Lopez-Sendon J L, Pais P, Parkhomenko A, Verheugt F W, Zhu J, Wallentin L, Investigators ACa: Apixaban versus warfarin in patients with atrial fibrillation. N Engl J Med 2011; 365:981-992.
6 Connolly S J, Eikelboom J, Joyner C, Diener H C, Hart R, Golitsyn S, Flaker G, Avezum A, Hohnloser S H, Diaz R, Talajic M, Zhu J, Pais P, Budaj A, Parkhomenko A, Jansky P, Commerford P, Tan R S, Sim K H, Lewis B S, Van Mieghem W, Lip G Y, Kim J H, Lanas-Zanetti F, Gonzalez-Hermosillo A, Dans A L, Munawar M, O'Donnell M, Lawrence J, Lewis G, Afzal R, Yusuf S, Investigators ASCa: Apixaban in patients with atrial fibrillation. N Engl J Med 2011; 364:806-817.
7 Prins M H, Lensing A W, Bauersachs R, van Bellen B, Bounameaux H, Brighton T A, Cohen A T, Davidson B L, Decousus H, Raskob G E, Berkowitz S D, Wells P S, Investigators E: Oral rivaroxaban versus standard therapy for the treatment of symptomatic venous thromboembolism: A pooled analysis of the einstein-dvt and pe randomized studies. Thromb J 2013; 11:21.
8 Schulman S, Kearon C, Kakkar A K, Mismetti P, Schellong S, Eriksson H, Baanstra D, Schnee J, Goldhaber S Z, Group R-CS: Dabigatran versus warfarin in the treatment of acute venous thromboembolism. N Engl J Med 2009; 361:2342-2352.
9 Quinlan D J, Eikelboom J W, Weitz J I: Four-factor prothrombin complex concentrate for urgent reversal of vitamin K antagonists in patients with major bleeding. Circulation 2013; 128:1179-1181.
10 Pabinger I, Brenner B, Kalina U, Knaub S, Nagy A, Ostermann H, Group BPNARS: Prothrombin complex concentrate (beriplex p/n) for emergency anticoagulation reversal: A prospective multinational clinical trial. J Thromb Haemost 2008; 6:622-631.
11 Lippi G, Favaloro E J, Cervellin G: Massive posttraumatic bleeding: Epidemiology, causes, clinical features, and therapeutic management. Semin Thromb Hemost 2013; 39:83-93.
12 Logan A C, Goodnough L T: Recombinant factor viia: An assessment of evidence regarding its efficacy and safety in the off-label setting. Hematology Am Soc Hematol Educ Program 2010; 2010:153-159.
13 Marlu R, Hodaj E, Paris A, Albaladejo P, Cracowski J L, Crackowski J L, Pernod G: Effect of non-specific reversal agents on anticoagulant activity of dabigatran and rivaroxaban: A randomised crossover ex vivo study in healthy volunteers. Thromb Haemost 2012; 108:217-224.
14 Skolnick B E, Mathews D R, Khutoryansky N M, Pusateri A E, Carr M E: Exploratory study on the reversal of warfarin with rfviia in healthy subjects. Blood 2010; 116:693-701.
15 Tanaka K A, Gruber A, Szlam F, Bush L A, Hanson S R, Di Cera E: Interaction between thrombin mutant w215a/e217a and direct thrombin inhibitor. Blood Coagul Fibrinolysis 2008; 19:465-468.
16 Schiele F, van Ryn J, Canada K, Newsome C, Sepulveda E, Park J, Nar H, Litzenburger T: A specific antidote for dabigatran: Functional and structural characterization. Blood 2013; 121:3554-3562.
17 Lu G, DeGuzman F R, Hollenbach S J, Karbarz M J, Abe K, Lee G, Luan P, Hutchaleelaha A, Inagaki M, Conley P B, Phillips D R, Sinha U: A specific antidote for reversal of anticoagulation by direct and indirect inhibitors of coagulation factor xa. Nat Med 2013; 19:446-451.
18 Mesters R M, Houghten R A, Griffin J H: Identification of a sequence of human activated protein c (residues 390-404) essential for its anticoagulant activity. The Journal of biological chemistry 1991; 266:24514-24519.
19 Gale A J, Xu X, Pellequer J L, Getzoff E D, Griffin J H: Interdomain engineered disulfide bond permitting elucidation of mechanisms of inactivation of coagulation factor va by activated protein c. Protein science: a publication of the Protein Society 2002; 11:2091-2101.
20 Radtke K P, Griffin J H, Riceberg J, Gale A J: Disulfide bond-stabilized factor viii has prolonged factor viiia activity and improved potency in whole blood clotting assays. Journal of thrombosis and haemostasis: JTH 2007; 5:102-108.
21 Hemker H C, Giesen P, AlDieri R, Regnault V, de Smed E, Wagenvoord R, Lecompte T, Beguin S: The calibrated automated thrombogram (cat): A universal routine test for hyper- and hypocoagulability. Pathophysiology of haemostasis and thrombosis 2002; 32:249-253.
22 Frost C, Nepal S, Wang J, Schuster A, Byon W, Boyd R A, Yu Z, Shenker A, Barrett Y C, Mosqueda-Garcia R, Lacreta F: Safety, pharmacokinetics and pharmacodynamics of multiple oral doses of apixaban, a factor xa inhibitor, in healthy subjects. Br J Clin Pharmacol 2013; 76:776-786.
23 Kubitza D, Becka M, Mueck W, Zuehlsdorf M: Rivaroxaban (bay 59-7939)—an oral, direct factor xa inhibitor—has no clinically relevant interaction with naproxen. Br J Clin Pharmacol 2007; 63:469-476.

The invention claimed is:

1. A method for treating adverse bleeding and/or promoting blood coagulation in an individual in need thereof comprising the administration of an effective amount of an activated variant Factor Va (FVa), wherein
   (i) the variant FVa necessarily comprises the following mutations: Arg306Gln, Arg506Gln, Arg679Gln, His609Cys, Glu1691Cys, and Ser2183Ala wherein the residue numbering of said mutations is relative to mature wild type human factor V which lacks the prepro polypeptide and an N-terminal methionine residue;
   (ii) the variant FVa polypeptide possesses the same deletion of residues of the B domain as SEQ ID NO: 4;
   (iii) the polypeptide possesses at least 90% sequence identity to the polypeptide of SEQ ID NO: 4 and
   (iv) said activated FVa more effectively treats bleeding and/or promotes blood coagulation compared to a wild-type FVa.

2. The method of claim 1, wherein the polypeptide possesses at least 95% sequence identity to the polypeptide of SEQ ID NO: 4.

3. The method of claim 1, wherein the activated variant FVa polypeptide has a sequence which is identical to SEQ ID NO: 4.

4. The method of claim 1, wherein the variant FVa comprises an intramolecular interdomain disulfide bridge.

5. The method of claim 1, wherein the method comprises administering the variant FVa in combination with at least one selected from Factor VIIa (FVIIa) and/or another procoagulant or pro-hemostatic agent which are in the same or different compositions.

6. The method of claim 5, wherein the variant FVa and the at least one of FVIIa and/or another procoagulant or pro-hemostatic agent are administered at the same time.

7. The method of claim 5, wherein the variant FVa and the at least one of FVIIa and/or another procoagulant or pro-hemostatic agent are administered sequentially.

8. The method of claim 5, wherein the combination elicits a synergistic or additive effect on thrombin generation and/or on hemostasis potential.

9. The method of claim 5, wherein the other procoagulant or pro-hemostatic agent is selected from factor II, factor V, factor VII, factor VIII, factor IX, factor X, factor XI, factor XII, factor XIII, factor H, activated forms of any of the foregoing factors, a prothrombin complex concentrate, prekallikrein, high molecular weight kininogen (HMWK), fresh frozen plasma, von Willebrand factor, an activated prothrombin complex concentrate, and any combination thereof.

10. The method of claim 5, wherein the method comprises administering the variant FVa in combination with FVIIa.

11. The method of claim 1, wherein the method comprises administering the variant FVa in combination with at least one anti-fibrinolytic.

12. The method of claim 11, wherein the anti-fibrinolytic is selected from thrombin activated fibrinolysis inhibitor (TAFI) derivatives, tranexamic acid, aminocaproic acid, epsilon-aminocaproic acid Amicar, epsilon-aminocaproic acid, aprotinin, and any combination thereof.

13. The method of claim 1, wherein the individual has or is at risk of developing a disease or condition associated with bleeding.

14. The method of claim 13, wherein the disease or condition associated with bleeding is selected from dysmenorrhea, hemorrhagic stroke or shock, trauma, surgery, a genetic disorder associated with abnormal bleeding, an acquired coagulation disorder, a hemostatic disorder, liver disease, bleeding due to Activated Protein C (APC) generation or administration, and bleeding caused by Novel Oral Anticoagulants (NOACs).

15. The method of claim 14, wherein the genetic disorder associated with abnormal bleeding is hemophilia or von Willebrand's disease.

16. The method of claim 14, wherein the disease or condition associated with bleeding comprises bleeding caused by NOACs.

17. The method of claim 16, wherein the NOAC is a direct FXa inhibitor and/or a thrombin inhibitor.

18. The method of claim 16, wherein the NOACs are selected from Rivaroxaban, Apixaban, Edoxaban, Dabigatran, and any combination thereof.

19. The method of claim 1, wherein the variant FVa is administered orally, subcutaneously, intravenously, intramuscularly, by infusion, by inhalation, or locally.

20. The method of claim 1, wherein the variant FVa is administered intravenously.

* * * * *

```
SEQUENCE LISTING

<160> NUMBER OF SEQ ID NOS: 4

<210> SEQ ID NO 1
<211> LENGTH: 1516
<212> TYPE: PRT
<213> ORGANISM: Artificial Sequence
<220> FEATURE:
<223> OTHER INFORMATION: superFVa

<400> SEQUENCE: 1

Ala Gln Leu Arg Gln Phe Tyr Val Ala Ala Gln Gly Ile Ser Trp Ser
1               5                   10                  15
```

```
Tyr Arg Pro Glu Pro Thr Asn Ser Ser Leu Asn Leu Ser Val Thr Ser
            20                  25                  30

Phe Lys Lys Ile Val Tyr Arg Glu Tyr Glu Pro Tyr Phe Lys Lys Glu
            35                  40                  45

Lys Pro Gln Ser Thr Ile Ser Gly Leu Leu Gly Pro Thr Leu Tyr Ala
 50                  55                  60

Glu Val Gly Asp Ile Ile Lys Val His Phe Lys Asn Lys Ala Asp Lys
 65                  70                  75                  80

Pro Leu Ser Ile His Pro Gln Gly Ile Arg Tyr Ser Lys Leu Ser Glu
                85                  90                  95

Gly Ala Ser Tyr Leu Asp His Thr Phe Pro Ala Glu Lys Met Asp Asp
            100                 105                 110

Ala Val Ala Pro Gly Arg Glu Tyr Thr Tyr Glu Trp Ser Ile Ser Glu
            115                 120                 125

Asp Ser Gly Pro Thr His Asp Asp Pro Pro Cys Leu Thr His Ile Tyr
            130                 135                 140

Tyr Ser His Glu Asn Leu Ile Glu Asp Phe Asn Ser Gly Leu Ile Gly
145                 150                 155                 160

Pro Leu Leu Ile Cys Lys Lys Gly Thr Leu Thr Glu Gly Gly Thr Gln
                165                 170                 175

Lys Thr Phe Asp Lys Gln Ile Val Leu Leu Phe Ala Val Phe Asp Glu
            180                 185                 190

Ser Lys Ser Trp Ser Gln Ser Ser Ser Leu Met Tyr Thr Val Asn Gly
            195                 200                 205

Tyr Val Asn Gly Thr Met Pro Asp Ile Thr Val Cys Ala His Asp His
210                 215                 220

Ile Ser Trp His Leu Leu Gly Met Ser Ser Gly Pro Glu Leu Phe Ser
225                 230                 235                 240

Ile His Phe Asn Gly Gln Val Leu Glu Gln Asn His His Lys Val Ser
                245                 250                 255

Ala Ile Thr Leu Val Ser Ala Thr Ser Thr Thr Ala Asn Met Thr Val
            260                 265                 270

Gly Pro Glu Gly Lys Trp Ile Ile Ser Ser Leu Thr Pro Lys His Leu
            275                 280                 285

Gln Ala Gly Met Gln Ala Tyr Ile Asp Ile Lys Asn Cys Pro Lys Lys
            290                 295                 300

Thr Gln Asn Leu Lys Lys Ile Thr Arg Glu Gln Arg Arg His Met Lys
305                 310                 315                 320

Arg Trp Glu Tyr Phe Ile Ala Ala Glu Glu Val Ile Trp Asp Tyr Ala
                325                 330                 335

Pro Val Ile Pro Ala Asn Met Asp Lys Lys Tyr Arg Ser Gln His Leu
            340                 345                 350

Asp Asn Phe Ser Asn Gln Ile Gly Lys His Tyr Lys Lys Val Met Tyr
            355                 360                 365

Thr Gln Tyr Glu Asp Glu Ser Phe Thr Lys His Thr Val Asn Pro Asn
 370                 375                 380

Met Lys Glu Asp Gly Ile Leu Gly Pro Ile Ile Arg Ala Gln Val Arg
385                 390                 395                 400

Asp Thr Leu Lys Ile Val Phe Lys Asn Met Ala Ser Arg Pro Tyr Ser
                405                 410                 415

Ile Tyr Pro His Gly Val Thr Phe Ser Pro Tyr Glu Asp Glu Val Asn
            420                 425                 430

Ser Ser Phe Thr Ser Gly Arg Asn Asn Thr Met Ile Arg Ala Val Gln
```

-continued

```
                435                 440                 445
Pro Gly Glu Thr Tyr Thr Tyr Lys Trp Asn Ile Leu Glu Phe Asp Glu
450                 455                 460
Pro Thr Glu Asn Asp Ala Gln Cys Leu Thr Arg Pro Tyr Tyr Ser Asp
465                 470                 475                 480
Val Asp Ile Met Arg Asp Ile Ala Ser Gly Leu Ile Gly Leu Leu Leu
                485                 490                 495
Ile Cys Lys Ser Arg Ser Leu Asp Arg Gln Gly Ile Gln Arg Ala Ala
                500                 505                 510
Asp Ile Glu Gln Gln Ala Val Phe Ala Val Phe Asp Glu Asn Lys Ser
                515                 520                 525
Trp Tyr Leu Glu Asp Asn Ile Asn Lys Phe Cys Glu Asn Pro Asp Glu
                530                 535                 540
Val Lys Arg Asp Asp Pro Lys Phe Tyr Glu Ser Asn Ile Met Ser Thr
545                 550                 555                 560
Ile Asn Gly Tyr Val Pro Glu Ser Ile Thr Thr Leu Gly Phe Cys Phe
                565                 570                 575
Asp Asp Thr Val Gln Trp His Phe Cys Ser Val Gly Thr Gln Asn Glu
                580                 585                 590
Ile Leu Thr Ile His Phe Thr Gly His Ser Phe Ile Tyr Gly Lys Arg
                595                 600                 605
Cys Glu Asp Thr Leu Thr Leu Phe Pro Met Arg Gly Glu Ser Val Thr
610                 615                 620
Val Thr Met Asp Asn Val Gly Thr Trp Met Leu Thr Ser Met Asn Ser
625                 630                 635                 640
Ser Pro Arg Ser Lys Lys Leu Arg Leu Lys Phe Arg Asp Val Lys Cys
                645                 650                 655
Ile Pro Asp Asp Glu Asp Ser Tyr Glu Ile Phe Glu Pro Pro Glu
                660                 665                 670
Ser Thr Val Met Ala Thr Gln Lys Met His Asp Arg Leu Glu Pro Glu
                675                 680                 685
Asp Glu Glu Ser Asp Ala Asp Tyr Asp Tyr Gln Asn Arg Leu Ala Ala
                690                 695                 700
Ala Leu Gly Ile Arg Ser Phe Arg Asn Ser Ser Leu Asn Gln Glu Glu
705                 710                 715                 720
Glu Glu Phe Asn Leu Thr Ala Leu Ala Leu Glu Asn Gly Thr Glu Phe
                725                 730                 735
Val Ser Ser Asn Thr Asp Ile Ile Val Gly Ser Asn Tyr Ser Ser Pro
                740                 745                 750
Ser Asn Ile Ser Lys Phe Thr Val Asn Asn Leu Ala Glu Pro Gln Lys
                755                 760                 765
Ala Pro Ser His Gln Gln Ala Thr Thr Ala Gly Ser Pro Leu Arg His
                770                 775                 780
Leu Ile Gly Lys Asn Ser Val Leu Asn Ser Ser Thr Ala Glu His Ser
785                 790                 795                 800
Ser Pro Tyr Ser Glu Asp Pro Ile Glu Asp Pro Thr Asp Tyr Ile Glu
                805                 810                 815
Ile Ile Pro Lys Glu Glu Val Gln Ser Ser Glu Asp Asp Tyr Ala Glu
                820                 825                 830
Ile Asp Tyr Val Pro Tyr Asp Asp Pro Tyr Lys Thr Asp Val Arg Thr
                835                 840                 845
Asn Ile Asn Ser Ser Arg Asp Pro Asp Asn Ile Ala Ala Trp Tyr Leu
850                 855                 860
```

```
Arg Ser Asn Asn Gly Asn Arg Arg Asn Tyr Tyr Ile Ala Ala Glu Glu
865                 870                 875                 880

Ile Ser Trp Asp Tyr Ser Glu Phe Val Gln Arg Glu Thr Asp Ile Glu
            885                 890                 895

Asp Ser Asp Asp Ile Pro Glu Asp Thr Thr Tyr Lys Lys Val Val Phe
                900                 905                 910

Arg Lys Tyr Leu Asp Ser Thr Phe Thr Lys Arg Asp Pro Arg Gly Glu
            915                 920                 925

Tyr Glu Glu His Leu Gly Ile Leu Gly Pro Ile Ile Arg Ala Glu Val
                930                 935                 940

Asp Asp Val Ile Gln Val Arg Phe Lys Asn Leu Ala Ser Arg Pro Tyr
945                 950                 955                 960

Ser Leu His Ala His Gly Leu Ser Tyr Glu Lys Ser Ser Glu Gly Lys
                965                 970                 975

Thr Tyr Glu Asp Asp Ser Pro Glu Trp Phe Lys Glu Asp Asn Ala Val
                980                 985                 990

Gln Pro Asn Ser Ser Tyr Thr Tyr Val Trp His Ala Thr Glu Arg Ser
            995                 1000                1005

Gly Pro Cys Ser Pro Gly Ser Ala Cys Arg Ala Trp Ala Tyr Tyr
        1010                1015                1020

Ser Ala Val Asn Pro Glu Lys Asp Ile His Ser Gly Leu Ile Gly
        1025                1030                1035

Pro Leu Leu Ile Cys Gln Lys Gly Ile Leu His Lys Asp Ser Asn
        1040                1045                1050

Met Pro Val Asp Met Arg Glu Phe Val Leu Leu Phe Met Thr Phe
        1055                1060                1065

Asp Glu Lys Lys Ser Trp Tyr Tyr Glu Lys Lys Ser Arg Ser Ser
        1070                1075                1080

Trp Arg Leu Thr Ser Ser Glu Met Lys Lys Ser His Glu Phe His
        1085                1090                1095

Ala Ile Asn Gly Met Ile Tyr Ser Leu Pro Gly Leu Lys Met Tyr
        1100                1105                1110

Glu Gln Glu Trp Val Arg Leu His Leu Leu Asn Ile Gly Gly Ser
        1115                1120                1125

Gln Asp Ile His Val Val His Phe His Gly Gln Thr Leu Leu Glu
        1130                1135                1140

Asn Gly Asn Lys Gln His Gln Leu Gly Val Trp Pro Leu Leu Pro
        1145                1150                1155

Gly Ser Phe Lys Thr Leu Glu Met Lys Ala Ser Lys Pro Gly Trp
        1160                1165                1170

Trp Leu Leu Asn Thr Glu Val Gly Glu Asn Gln Arg Ala Gly Met
        1175                1180                1185

Gln Thr Pro Phe Leu Ile Met Asp Arg Asp Cys Arg Met Pro Met
        1190                1195                1200

Gly Leu Ser Thr Gly Ile Ile Ser Asp Ser Gln Ile Lys Ala Ser
        1205                1210                1215

Glu Phe Leu Gly Tyr Trp Glu Pro Arg Leu Ala Arg Leu Asn Asn
        1220                1225                1230

Gly Gly Ser Tyr Asn Ala Trp Ser Val Glu Lys Leu Ala Ala Glu
        1235                1240                1245

Phe Ala Ser Lys Pro Trp Ile Gln Val Asp Met Gln Lys Glu Val
        1250                1255                1260
```

```
Ile Ile Thr Gly Ile Gln Thr Gln Gly Ala Lys His Tyr Leu Lys
1265                1270                1275

Ser Cys Tyr Thr Thr Glu Phe Tyr Val Ala Tyr Ser Ser Asn Gln
    1280                1285                1290

Ile Asn Trp Gln Ile Phe Lys Gly Asn Ser Thr Arg Asn Val Met
    1295                1300                1305

Tyr Phe Asn Gly Asn Ser Asp Ala Ser Thr Ile Lys Glu Asn Gln
    1310                1315                1320

Phe Asp Pro Pro Ile Val Ala Arg Tyr Ile Arg Ile Ser Pro Thr
    1325                1330                1335

Arg Ala Tyr Asn Arg Pro Thr Leu Arg Leu Glu Leu Gln Gly Cys
    1340                1345                1350

Glu Val Asn Gly Cys Ser Thr Pro Leu Gly Met Glu Asn Gly Lys
    1355                1360                1365

Ile Glu Asn Lys Gln Ile Thr Ala Ser Ser Phe Lys Lys Ser Trp
    1370                1375                1380

Trp Gly Asp Tyr Trp Glu Pro Phe Arg Ala Arg Leu Asn Ala Gln
    1385                1390                1395

Gly Arg Val Asn Ala Trp Gln Ala Lys Ala Asn Asn Lys Gln
    1400                1405                1410

Trp Leu Glu Ile Asp Leu Leu Lys Ile Lys Lys Ile Thr Ala Ile
    1415                1420                1425

Ile Thr Gln Gly Cys Lys Ser Leu Ser Ser Glu Met Tyr Val Lys
    1430                1435                1440

Ser Tyr Thr Ile His Tyr Ser Glu Gln Gly Val Glu Trp Lys Pro
    1445                1450                1455

Tyr Arg Leu Lys Ser Ser Met Val Asp Lys Ile Phe Glu Gly Asn
    1460                1465                1470

Thr Asn Thr Lys Gly His Val Lys Asn Phe Phe Asn Pro Pro Ile
    1475                1480                1485

Ile Ser Arg Phe Ile Arg Val Ile Pro Lys Thr Trp Asn Gln Ala
    1490                1495                1500

Ile Thr Leu Arg Leu Glu Leu Phe Gly Cys Asp Ile Tyr
    1505                1510                1515

<210> SEQ ID NO 2
<211> LENGTH: 406
<212> TYPE: PRT
<213> ORGANISM: Homo sapiens

<400> SEQUENCE: 2

Ala Asn Ala Phe Leu Glu Glu Leu Arg Pro Gly Ser Leu Glu Arg Glu
1               5                   10                  15

Cys Lys Glu Glu Gln Cys Ser Phe Glu Glu Ala Arg Glu Ile Phe Lys
                20                  25                  30

Asp Ala Glu Arg Thr Lys Leu Phe Trp Ile Ser Tyr Ser Asp Gly Asp
            35                  40                  45

Gln Cys Ala Ser Ser Pro Cys Gln Asn Gly Gly Ser Cys Lys Asp Gln
        50                  55                  60

Leu Gln Ser Tyr Ile Cys Phe Cys Leu Pro Ala Phe Gly Arg Asn
65                  70                  75              80

Cys Glu Thr His Lys Asp Asp Gln Leu Ile Cys Val Asn Glu Asn Gly
                85                  90                  95

Gly Cys Glu Gln Tyr Cys Ser Asp His Thr Gly Thr Lys Arg Ser Cys
            100                 105                 110
```

```
Arg Cys His Glu Gly Tyr Ser Leu Leu Ala Asp Gly Val Ser Cys Thr
            115                 120                 125

Pro Thr Val Glu Tyr Pro Cys Gly Lys Ile Pro Ile Leu Glu Lys Arg
130                 135                 140

Asn Ala Ser Lys Pro Gln Gly Arg Ile Val Gly Lys Val Cys Pro
145                 150                 155                 160

Lys Gly Glu Cys Pro Trp Gln Val Leu Leu Leu Val Asn Gly Ala Gln
                165                 170                 175

Leu Cys Gly Gly Thr Leu Ile Asn Thr Ile Trp Val Val Ser Ala Ala
            180                 185                 190

His Cys Phe Asp Lys Ile Lys Asn Trp Arg Asn Leu Ile Ala Val Leu
        195                 200                 205

Gly Glu His Asp Leu Ser Glu His Asp Gly Asp Glu Gln Ser Arg Arg
    210                 215                 220

Val Ala Gln Val Ile Ile Pro Ser Thr Tyr Val Pro Gly Thr Thr Asn
225                 230                 235                 240

His Asp Ile Ala Leu Leu Arg Leu His Gln Pro Val Val Leu Thr Asp
                245                 250                 255

His Val Val Pro Leu Cys Leu Pro Glu Arg Thr Phe Ser Glu Arg Thr
            260                 265                 270

Leu Ala Phe Val Arg Phe Ser Leu Val Ser Gly Trp Gly Gln Leu Leu
        275                 280                 285

Asp Arg Gly Ala Thr Ala Leu Glu Leu Met Val Leu Asn Val Pro Arg
    290                 295                 300

Leu Met Thr Gln Asp Cys Leu Gln Gln Ser Arg Lys Val Gly Asp Ser
305                 310                 315                 320

Pro Asn Ile Thr Glu Tyr Met Phe Cys Ala Gly Tyr Ser Asp Gly Ser
                325                 330                 335

Lys Asp Ser Cys Lys Gly Asp Ser Gly Gly Pro His Ala Thr His Tyr
            340                 345                 350

Arg Gly Thr Trp Tyr Leu Thr Gly Ile Val Ser Trp Gly Gln Gly Cys
        355                 360                 365

Ala Thr Val Gly His Phe Gly Val Tyr Thr Arg Val Ser Gln Tyr Ile
    370                 375                 380

Glu Trp Leu Gln Lys Leu Met Arg Ser Glu Pro Arg Pro Gly Val Leu
385                 390                 395                 400

Leu Arg Ala Pro Phe Pro
                405

<210> SEQ ID NO 3
<211> LENGTH: 466
<212> TYPE: PRT
<213> ORGANISM: Homo sapiens

<400> SEQUENCE: 3

Met Val Ser Gln Ala Leu Arg Leu Leu Cys Leu Leu Leu Gly Leu Gln
1               5                   10                  15

Gly Cys Leu Ala Ala Gly Gly Val Ala Lys Ala Ser Gly Gly Glu Thr
            20                  25                  30

Arg Asp Met Pro Trp Lys Pro Gly Pro His Arg Val Phe Val Thr Gln
        35                  40                  45

Glu Glu Ala His Gly Val Leu His Arg Arg Arg Ala Asn Ala Phe
    50                  55                  60

Leu Glu Glu Leu Arg Pro Gly Ser Leu Glu Arg Glu Cys Lys Glu Glu
```

65                  70                  75                  80
        Gln Cys Ser Phe Glu Glu Ala Arg Glu Ile Phe Lys Asp Ala Glu Arg
                        85                  90                  95
        Thr Lys Leu Phe Trp Ile Ser Tyr Ser Asp Gly Asp Gln Cys Ala Ser
                        100                 105                 110
        Ser Pro Cys Gln Asn Gly Gly Ser Cys Lys Asp Gln Leu Gln Ser Tyr
                        115                 120                 125
        Ile Cys Phe Cys Leu Pro Ala Phe Glu Gly Arg Asn Cys Glu Thr His
                        130                 135                 140
        Lys Asp Asp Gln Leu Ile Cys Val Asn Glu Asn Gly Gly Cys Glu Gln
        145                 150                 155                 160
        Tyr Cys Ser Asp His Thr Gly Thr Lys Arg Ser Cys Arg Cys His Glu
                        165                 170                 175
        Gly Tyr Ser Leu Leu Ala Asp Gly Val Ser Cys Thr Pro Thr Val Glu
                        180                 185                 190
        Tyr Pro Cys Gly Lys Ile Pro Ile Leu Glu Lys Arg Asn Ala Ser Lys
                        195                 200                 205
        Pro Gln Gly Arg Ile Val Gly Gly Lys Val Cys Pro Lys Gly Glu Cys
                        210                 215                 220
        Pro Trp Gln Val Leu Leu Leu Val Asn Gly Ala Gln Leu Cys Gly Gly
        225                 230                 235                 240
        Thr Leu Ile Asn Thr Ile Trp Val Val Ser Ala Ala His Cys Phe Asp
                        245                 250                 255
        Lys Ile Lys Asn Trp Arg Asn Leu Ile Ala Val Leu Gly Glu His Asp
                        260                 265                 270
        Leu Ser Glu His Asp Gly Asp Glu Gln Ser Arg Arg Val Ala Gln Val
                        275                 280                 285
        Ile Ile Pro Ser Thr Tyr Val Pro Gly Thr Thr Asn His Asp Ile Ala
                        290                 295                 300
        Leu Leu Arg Leu His Gln Pro Val Val Leu Thr Asp His Val Val Pro
        305                 310                 315                 320
        Leu Cys Leu Pro Glu Arg Thr Phe Ser Glu Arg Thr Leu Ala Phe Val
                        325                 330                 335
        Arg Phe Ser Leu Val Ser Gly Trp Gly Gln Leu Leu Asp Arg Gly Ala
                        340                 345                 350
        Thr Ala Leu Glu Leu Met Val Leu Asn Val Pro Arg Leu Met Thr Gln
                        355                 360                 365
        Asp Cys Leu Gln Gln Ser Arg Lys Val Gly Asp Ser Pro Asn Ile Thr
                        370                 375                 380
        Glu Tyr Met Phe Cys Ala Gly Tyr Ser Asp Gly Ser Lys Asp Ser Cys
        385                 390                 395                 400
        Lys Gly Asp Ser Gly Gly Pro His Ala Thr His Tyr Arg Gly Thr Trp
                        405                 410                 415
        Tyr Leu Thr Gly Ile Val Ser Trp Gly Gln Gly Cys Ala Thr Val Gly
                        420                 425                 430
        His Phe Gly Val Tyr Thr Arg Val Ser Gln Tyr Ile Glu Trp Leu Gln
                        435                 440                 445
        Lys Leu Met Arg Ser Glu Pro Arg Pro Gly Val Leu Leu Arg Ala Pro
                        450                 455                 460
        Phe Pro
        465

<210> SEQ ID NO 4

<211> LENGTH: 1516
<212> TYPE: PRT
<213> ORGANISM: Artificial Sequence
<220> FEATURE:
<223> OTHER INFORMATION: super FVa

<400> SEQUENCE: 4

```
Ala Gln Leu Arg Gln Phe Tyr Val Ala Gln Gly Ile Ser Trp Ser
1               5                   10                  15

Tyr Arg Pro Glu Pro Thr Asn Ser Ser Leu Asn Leu Ser Val Thr Ser
            20                  25                  30

Phe Lys Lys Ile Val Tyr Arg Glu Tyr Glu Pro Tyr Phe Lys Lys Glu
        35                  40                  45

Lys Pro Gln Ser Thr Ile Ser Gly Leu Leu Gly Pro Thr Leu Tyr Ala
    50                  55                  60

Glu Val Gly Asp Ile Ile Lys Val His Phe Lys Asn Lys Ala Asp Lys
65                  70                  75                  80

Pro Leu Ser Ile His Pro Gln Gly Ile Arg Tyr Ser Lys Leu Ser Glu
                85                  90                  95

Gly Ala Ser Tyr Leu Asp His Thr Phe Pro Ala Glu Lys Met Asp Asp
            100                 105                 110

Ala Val Ala Pro Gly Arg Glu Tyr Thr Tyr Glu Trp Ser Ile Ser Glu
        115                 120                 125

Asp Ser Gly Pro Thr His Asp Asp Pro Pro Cys Leu Thr His Ile Tyr
    130                 135                 140

Tyr Ser His Glu Asn Leu Ile Glu Asp Phe Asn Ser Gly Leu Ile Gly
145                 150                 155                 160

Pro Leu Leu Ile Cys Lys Lys Gly Thr Leu Thr Glu Gly Gly Thr Gln
                165                 170                 175

Lys Thr Phe Asp Lys Gln Ile Val Leu Leu Phe Ala Val Phe Asp Glu
            180                 185                 190

Ser Lys Ser Trp Ser Gln Ser Ser Ser Leu Met Tyr Thr Val Asn Gly
        195                 200                 205

Tyr Val Asn Gly Thr Met Pro Asp Ile Thr Val Cys Ala His Asp His
    210                 215                 220

Ile Ser Trp His Leu Leu Gly Met Ser Ser Gly Pro Glu Leu Phe Ser
225                 230                 235                 240

Ile His Phe Asn Gly Gln Val Leu Glu Gln Asn His His Lys Val Ser
                245                 250                 255

Ala Ile Thr Leu Val Ser Ala Thr Ser Thr Thr Ala Asn Met Thr Val
            260                 265                 270

Gly Pro Glu Gly Lys Trp Ile Ile Ser Ser Leu Thr Pro Lys His Leu
        275                 280                 285

Gln Ala Gly Met Gln Ala Tyr Ile Asp Ile Lys Asn Cys Pro Lys Lys
    290                 295                 300

Thr Gln Asn Leu Lys Lys Ile Thr Arg Glu Gln Arg Arg His Met Lys
305                 310                 315                 320

Arg Trp Glu Tyr Phe Ile Ala Ala Glu Glu Val Ile Trp Asp Tyr Ala
                325                 330                 335

Pro Val Ile Pro Ala Asn Met Asp Lys Lys Tyr Arg Ser Gln His Leu
            340                 345                 350

Asp Asn Phe Ser Asn Gln Ile Gly Lys His Tyr Lys Lys Val Met Tyr
        355                 360                 365

Thr Gln Tyr Glu Asp Glu Ser Phe Thr Lys His Thr Val Asn Pro Asn
    370                 375                 380
```

```
Met Lys Glu Asp Gly Ile Leu Gly Pro Ile Ile Arg Ala Gln Val Arg
385                 390                 395                 400

Asp Thr Leu Lys Ile Val Phe Lys Asn Met Ala Ser Arg Pro Tyr Ser
            405                 410                 415

Ile Tyr Pro His Gly Val Thr Phe Ser Pro Tyr Glu Asp Glu Val Asn
        420                 425                 430

Ser Ser Phe Thr Ser Gly Arg Asn Asn Thr Met Ile Arg Ala Val Gln
        435                 440                 445

Pro Gly Glu Thr Tyr Thr Tyr Lys Trp Asn Ile Leu Glu Phe Asp Glu
        450                 455                 460

Pro Thr Glu Asn Asp Ala Gln Cys Leu Thr Arg Pro Tyr Tyr Ser Asp
465                 470                 475                 480

Val Asp Ile Met Arg Asp Ile Ala Ser Gly Leu Ile Gly Leu Leu Leu
            485                 490                 495

Ile Cys Lys Ser Arg Ser Leu Asp Arg Gln Gly Ile Gln Arg Ala Ala
        500                 505                 510

Asp Ile Glu Gln Gln Ala Val Phe Ala Val Phe Asp Glu Asn Lys Ser
        515                 520                 525

Trp Tyr Leu Glu Asp Asn Ile Asn Lys Phe Cys Glu Asn Pro Asp Glu
        530                 535                 540

Val Lys Arg Asp Asp Pro Lys Phe Tyr Glu Ser Asn Ile Met Ser Thr
545                 550                 555                 560

Ile Asn Gly Tyr Val Pro Glu Ser Ile Thr Thr Leu Gly Phe Cys Phe
            565                 570                 575

Asp Asp Thr Val Gln Trp His Phe Cys Ser Val Gly Thr Gln Asn Glu
        580                 585                 590

Ile Leu Thr Ile His Phe Thr Gly His Ser Phe Ile Tyr Gly Lys Arg
        595                 600                 605

Cys Glu Asp Thr Leu Thr Leu Phe Pro Met Arg Gly Glu Ser Val Thr
        610                 615                 620

Val Thr Met Asp Asn Val Gly Thr Trp Met Leu Thr Ser Met Asn Ser
625                 630                 635                 640

Ser Pro Arg Ser Lys Lys Leu Arg Leu Lys Phe Arg Asp Val Lys Cys
            645                 650                 655

Ile Pro Asp Asp Asp Glu Asp Ser Tyr Glu Ile Phe Glu Pro Pro Glu
        660                 665                 670

Ser Thr Val Met Ala Thr Gln Lys Met His Asp Arg Leu Glu Pro Glu
        675                 680                 685

Asp Glu Glu Ser Asp Ala Asp Tyr Asp Tyr Gln Asn Arg Leu Ala Ala
        690                 695                 700

Ala Leu Gly Ile Arg Ser Phe Arg Asn Ser Ser Leu Asn Gln Glu Glu
705                 710                 715                 720

Glu Glu Phe Asn Leu Thr Ala Leu Ala Leu Glu Asn Gly Thr Glu Phe
            725                 730                 735

Val Ser Ser Asn Thr Asp Ile Ile Val Gly Ser Asn Tyr Ser Ser Pro
        740                 745                 750

Ser Asn Ile Ser Lys Phe Thr Val Asn Asn Leu Ala Glu Pro Gln Lys
        755                 760                 765

Ala Pro Ser His Gln Gln Ala Thr Thr Ala Gly Ser Pro Leu Arg His
        770                 775                 780

Leu Ile Gly Lys Asn Ser Val Leu Asn Ser Ser Thr Ala Glu His Ser
785                 790                 795                 800
```

-continued

Ser Pro Tyr Ser Glu Asp Pro Ile Glu Asp Pro Thr Asp Tyr Ile Glu
            805                 810                 815

Ile Ile Pro Lys Glu Glu Val Gln Ser Ser Glu Asp Tyr Ala Glu
        820                 825                 830

Ile Asp Tyr Val Pro Tyr Asp Pro Tyr Lys Thr Asp Val Arg Thr
        835                 840                 845

Asn Ile Asn Ser Ser Arg Asp Pro Asp Asn Ile Ala Ala Trp Tyr Leu
850                 855                 860

Arg Ser Asn Asn Gly Asn Arg Arg Asn Tyr Ile Ala Ala Glu Glu
865                 870                 875                 880

Ile Ser Trp Asp Tyr Ser Glu Phe Val Gln Arg Glu Thr Asp Ile Glu
            885                 890                 895

Asp Ser Asp Asp Ile Pro Glu Asp Thr Thr Tyr Lys Lys Val Val Phe
            900                 905                 910

Arg Lys Tyr Leu Asp Ser Thr Phe Thr Lys Arg Asp Pro Arg Gly Glu
            915                 920                 925

Tyr Glu Glu His Leu Gly Ile Leu Gly Pro Ile Ile Arg Ala Glu Val
930                 935                 940

Asp Asp Val Ile Gln Val Arg Phe Lys Asn Leu Ala Ser Arg Pro Tyr
945                 950                 955                 960

Ser Leu His Ala His Gly Leu Ser Tyr Glu Lys Ser Ser Glu Gly Lys
            965                 970                 975

Thr Tyr Glu Asp Asp Ser Pro Glu Trp Phe Lys Glu Asp Asn Ala Val
            980                 985                 990

Gln Pro Asn Ser Ser Tyr Thr Tyr Val Trp His Ala Thr Glu Arg Ser
            995                 1000                1005

Gly Pro Cys Ser Pro Gly Ser Ala Cys Arg Ala Trp Ala Tyr Tyr
        1010                1015                1020

Ser Ala Val Asn Pro Glu Lys Asp Ile His Ser Gly Leu Ile Gly
        1025                1030                1035

Pro Leu Leu Ile Cys Gln Lys Gly Ile Leu His Lys Asp Ser Asn
        1040                1045                1050

Met Pro Val Asp Met Arg Glu Phe Val Leu Leu Phe Met Thr Phe
        1055                1060                1065

Asp Glu Lys Lys Ser Trp Tyr Tyr Glu Lys Lys Ser Arg Ser Ser
        1070                1075                1080

Trp Arg Leu Thr Ser Ser Glu Met Lys Lys Ser His Glu Phe His
        1085                1090                1095

Ala Ile Asn Gly Met Ile Tyr Ser Leu Pro Gly Leu Lys Met Tyr
        1100                1105                1110

Glu Gln Glu Trp Val Arg Leu His Leu Leu Asn Ile Gly Gly Ser
        1115                1120                1125

Gln Asp Ile His Val Val His Phe His Gly Gln Thr Leu Leu Glu
        1130                1135                1140

Asn Gly Asn Lys Gln His Gln Leu Gly Val Trp Pro Leu Leu Pro
        1145                1150                1155

Gly Ser Phe Lys Thr Leu Glu Met Lys Ala Ser Lys Pro Gly Trp
        1160                1165                1170

Trp Leu Leu Asn Thr Glu Val Gly Glu Asn Gln Arg Ala Gly Met
        1175                1180                1185

Gln Thr Pro Phe Leu Ile Met Asp Arg Asp Cys Arg Met Pro Met
        1190                1195                1200

Gly Leu Ser Thr Gly Ile Ile Ser Asp Ser Gln Ile Lys Ala Ser

```
                   1205                1210                1215
Glu Phe Leu Gly Tyr Trp Glu Pro Arg Leu Ala Arg Leu Asn Asn
       1220                1225                1230
Gly Gly Ser Tyr Asn Ala Trp Ser Val Glu Lys Leu Ala Ala Glu
       1235                1240                1245
Phe Ala Ser Lys Pro Trp Ile Gln Val Asp Met Gln Lys Glu Val
       1250                1255                1260
Ile Ile Thr Gly Ile Gln Thr Gln Gly Ala Lys His Tyr Leu Lys
       1265                1270                1275
Ser Cys Tyr Thr Thr Glu Phe Tyr Val Ala Tyr Ser Ser Asn Gln
       1280                1285                1290
Ile Asn Trp Gln Ile Phe Lys Gly Asn Ser Thr Arg Asn Val Met
       1295                1300                1305
Tyr Phe Asn Gly Asn Ser Asp Ala Ser Thr Ile Lys Glu Asn Gln
       1310                1315                1320
Phe Asp Pro Pro Ile Val Ala Arg Tyr Ile Arg Ile Ser Pro Thr
       1325                1330                1335
Arg Ala Tyr Asn Arg Pro Thr Leu Arg Leu Glu Leu Gln Gly Cys
       1340                1345                1350
Glu Val Asn Gly Cys Ser Thr Pro Leu Gly Met Glu Asn Gly Lys
       1355                1360                1365
Ile Glu Asn Lys Gln Ile Thr Ala Ser Ser Phe Lys Lys Ser Trp
       1370                1375                1380
Trp Gly Asp Tyr Trp Glu Pro Phe Arg Ala Arg Leu Asn Ala Gln
       1385                1390                1395
Gly Arg Val Asn Ala Trp Gln Ala Lys Ala Asn Asn Asn Lys Gln
       1400                1405                1410
Trp Leu Glu Ile Asp Leu Leu Lys Ile Lys Lys Ile Thr Ala Ile
       1415                1420                1425
Ile Thr Gln Gly Cys Lys Ser Leu Ser Ser Glu Met Tyr Val Lys
       1430                1435                1440
Ser Tyr Thr Ile His Tyr Ser Glu Gln Gly Val Glu Trp Lys Pro
       1445                1450                1455
Tyr Arg Leu Lys Ser Ser Met Val Asp Lys Ile Phe Glu Gly Asn
       1460                1465                1470
Thr Asn Thr Lys Gly His Val Lys Asn Phe Phe Asn Pro Pro Ile
       1475                1480                1485
Ile Ser Arg Phe Ile Arg Val Ile Pro Lys Thr Trp Asn Gln Ala
       1490                1495                1500
Ile Ala Leu Arg Leu Glu Leu Phe Gly Cys Asp Ile Tyr
       1505                1510                1515
```